United States Patent
Laurie et al.

(10) Patent No.: US 12,233,108 B2
(45) Date of Patent: Feb. 25, 2025

(54) COMPOSITIONS AND METHODS FOR PROMOTING ISLET VIABILITY AND ENHANCING INSULIN SECRETION

(71) Applicant: University of Virginia Patent Foundation, Charlottesville, VA (US)

(72) Inventors: Gordon W. Laurie, Charlottesville, VA (US); Kenneth Brayman, Charlottesville, VA (US); Preeti Chhabra, Waynesboro, VA (US); Mingyang Ma, Charlottesville, VA (US); Karina Teixeira, Charlottesville, VA (US); Thomas R. Gadek, Park City, UT (US)

(73) Assignee: University of Virginia Patent Foundation, Charlottesville, VA (US)

( * ) Notice: Subject to any disclaimer, the term of this patent is extended or adjusted under 35 U.S.C. 154(b) by 496 days.

(21) Appl. No.: 17/438,760

(22) PCT Filed: Mar. 13, 2020

(86) PCT No.: PCT/US2020/022822
§ 371 (c)(1),
(2) Date: Sep. 13, 2021

(87) PCT Pub. No.: WO2020/186247
PCT Pub. Date: Sep. 17, 2020

(65) Prior Publication Data
US 2022/0160838 A1    May 26, 2022

Related U.S. Application Data

(60) Provisional application No. 62/817,790, filed on Mar. 13, 2019.

(51) Int. Cl.
*A61K 38/39* (2006.01)
*A61K 35/39* (2015.01)
*A61K 38/26* (2006.01)

(52) U.S. Cl.
CPC .............. *A61K 38/26* (2013.01); *A61K 35/39* (2013.01)

(58) Field of Classification Search
None
See application file for complete search history.

(56) References Cited

U.S. PATENT DOCUMENTS

| | | | |
|---|---|---|---|
| 2005/0208558 A1* | 9/2005 | Venter | C12Q 1/6888 435/6.16 |
| 2013/0196926 A1 | 8/2013 | Mackay et al. | |
| 2014/0030234 A1 | 1/2014 | Kim et al. | |

FOREIGN PATENT DOCUMENTS

| | | |
|---|---|---|
| WO | WO 2005/119899 A2 | 12/2005 |
| WO | WO 2015/138604 A1 | 9/2015 |
| WO | WO 2020/186247 A1 | 9/2020 |

OTHER PUBLICATIONS

Bansal et al, Indian J. Med. Res. (2013) 137 p. 695-703.*
International Search Report and Written Opinion corresponding to International Patent Application No. PCT/US2020/022822 dated Jul. 31, 2020.
McKown et al. (2009) "Lacritin and Other New Proteins of the Lacrimal Functional Unit," Experimental Eye Research, vol. 88, No. 5, pp. 848-858.
Extended European Search Report dated Oct. 13, 2022 for EP Patent Application No. 20769767.3 in 19 pages.
Office Action dated Nov. 21, 2023 for EP Patent Application No. 20769767.3 in 14 pages.
Deboer et al., "LaunchPad for Diabetes Funded Projects 2015-2019", Apr. 1, 2020. Retrieved from the Internet: URL:https://research.virginia.edu/site/ypr/files/2020.04/All.LaunchPad.for.DiabetesFundedProjects2015_2019.pdf [Retrieve on Oct. 4, 2024].
"LacripepTM-like Peptide N-104 Increases Insulin Secretion and Promotes Islet Transplantation Outcomes—ATC Abstracts", Jun. 1, 2021, Retrieved from the Internet: URL :https ://atcmeeti n g abstracts. co m/abstract/lacri peptm-l i ke-peptiden-104-increases-insulin-secretion-and-promotes-islet-transplantationoutcomes/ ([retrieved on Oct. 4, 2024].
"Laurie, Gordon W.—Ophthalmology", Aug. 9, 2020, Retrieved from the Internet: URL:https://web.archive.org/web/20200809060157/ https://med.virginia.edu/ophthalmology/research/vision-research-group/?facbio=1 &id=25809 [retrieved on Oct. 4, 2024].
Communication pursuant to Article 94(3) EPC dated Nov. 21, 2023 for EP Patent Application No. 20769767.3 in 14 pages.
Communication pursuant to Article 94(3) EPC dated May 27, 2024 for EP Patent Application No. 20769767.3 in 10 pages.

* cited by examiner

*Primary Examiner* — Fred H Reynolds
(74) *Attorney, Agent, or Firm* — Knobbe, Martens, Olson & Bear, LLP

(57) ABSTRACT

Compositions and methods for regenerating pancreatic islet viability and/or cell proliferation in vitro, ex vivo, and/or in vivo; and/or for regenerating glucose-stimulated insulin secretion; and/or for regenerating viability and/or cell proliferation of a transplanted pancreatic islets; and/or for preventing and/or inhibiting rejection of a transplanted islets; and/or for pancreatic islet transplantation; and/or for treating a symptom of a condition, disorder, or disease associated with abnormal insulin responsiveness to glucose are provided. In some embodiments, the compositions include a peptide and/or a pharmaceutically acceptable salt thereof, and/or a biologically active fragment, analog, or derivative thereof, wherein the peptide, the pharmaceutically acceptable salt thereof, and/or the biologically active fragment, analog, or derivative thereof has an amino acid sequence of any of SEQ ID NOs: 1-60, or any combination thereof.

28 Claims, 8 Drawing Sheets
Specification includes a Sequence Listing.

SEQUENCE LISTING

```
<160> NUMBER OF SEQ ID NOS: 63

<210> SEQ ID NO 1
<211> LENGTH: 19
<212> TYPE: PRT
<213> ORGANISM: Artificial Sequence
<220> FEATURE:
<223> OTHER INFORMATION: Artificially synthesized peptide

<400> SEQUENCE: 1

Lys Gln Phe Ile Glu Asn Gly Ser Glu Phe Ala Gln Lys Leu Leu Lys
1               5                   10                  15
```

Lys Phe Ser

```
<210> SEQ ID NO 2
<211> LENGTH: 20
<212> TYPE: PRT
<213> ORGANISM: Artificial Sequence
<220> FEATURE:
<223> OTHER INFORMATION: Artificially synthesized peptide

<400> SEQUENCE: 2
```

Cys Lys Gln Phe Ile Glu Asn Gly Ser Glu Phe Ala Gln Lys Leu Leu
1               5                   10                  15

Lys Lys Phe Ser
            20

```
<210> SEQ ID NO 3
<211> LENGTH: 20
<212> TYPE: PRT
<213> ORGANISM: Artificial Sequence
<220> FEATURE:
<223> OTHER INFORMATION: Artificially synthesized peptide

<400> SEQUENCE: 3
```

Lys Gln Phe Ile Glu Asn Gly Ser Glu Phe Ala Gln Lys Leu Leu Lys
1               5                   10                  15

Lys Phe Ser Cys
            20

```
<210> SEQ ID NO 4
<211> LENGTH: 21
<212> TYPE: PRT
<213> ORGANISM: Artificial Sequence
<220> FEATURE:
<223> OTHER INFORMATION: Artificially synthesized peptide

<400> SEQUENCE: 4
```

Cys Lys Gln Phe Ile Glu Asn Gly Ser Glu Phe Ala Gln Lys Leu Leu
1               5                   10                  15

Lys Lys Phe Ser Cys
            20

```
<210> SEQ ID NO 5
<211> LENGTH: 25
<212> TYPE: PRT
<213> ORGANISM: Artificial Sequence
<220> FEATURE:
<223> OTHER INFORMATION: Artificially synthesized peptide

<400> SEQUENCE: 5
```

Lys Asn Phe Ile Glu Asn Gly Ser Glu Phe Ala Gln Lys Leu Leu Lys
1               5                   10                  15

Lys Phe Ser Leu Leu Lys Pro Trp Ala
            20                  25

```
<210> SEQ ID NO 6
<211> LENGTH: 26
<212> TYPE: PRT
<213> ORGANISM: Artificial Sequence
<220> FEATURE:
<223> OTHER INFORMATION: Artificially synthesized peptide

<400> SEQUENCE: 6
```

Cys Lys Asn Phe Ile Glu Asn Gly Ser Glu Phe Ala Gln Lys Leu Leu
1               5                   10                  15

```
Lys Lys Phe Ser Leu Leu Lys Pro Trp Ala
            20                  25

<210> SEQ ID NO 7
<211> LENGTH: 26
<212> TYPE: PRT
<213> ORGANISM: Artificial Sequence
<220> FEATURE:
<223> OTHER INFORMATION: Artificially synthesized peptide

<400> SEQUENCE: 7

Lys Asn Phe Ile Glu Asn Gly Ser Glu Phe Ala Gln Lys Leu Leu Lys
1               5                   10                  15

Lys Phe Ser Leu Leu Lys Pro Trp Ala Cys
            20                  25

<210> SEQ ID NO 8
<211> LENGTH: 27
<212> TYPE: PRT
<213> ORGANISM: Artificial Sequence
<220> FEATURE:
<223> OTHER INFORMATION: Artificially synthesized peptide

<400> SEQUENCE: 8

Cys Lys Asn Phe Ile Glu Asn Gly Ser Glu Phe Ala Gln Lys Leu Leu
1               5                   10                  15

Lys Lys Phe Ser Leu Leu Lys Pro Trp Ala Cys
            20                  25

<210> SEQ ID NO 9
<211> LENGTH: 25
<212> TYPE: PRT
<213> ORGANISM: Artificial Sequence
<220> FEATURE:
<223> OTHER INFORMATION: Artificially synthesized peptide

<400> SEQUENCE: 9

Lys Gln Phe Ile Glu Asn Gly Ser Glu Phe Ala Asn Lys Leu Leu Lys
1               5                   10                  15

Lys Phe Ser Leu Leu Lys Pro Trp Ala
            20                  25

<210> SEQ ID NO 10
<211> LENGTH: 26
<212> TYPE: PRT
<213> ORGANISM: Artificial Sequence
<220> FEATURE:
<223> OTHER INFORMATION: Artificially synthesized peptide

<400> SEQUENCE: 10

Cys Lys Gln Phe Ile Glu Asn Gly Ser Glu Phe Ala Asn Lys Leu Leu
1               5                   10                  15

Lys Lys Phe Ser Leu Leu Lys Pro Trp Ala
            20                  25

<210> SEQ ID NO 11
<211> LENGTH: 26
<212> TYPE: PRT
<213> ORGANISM: Artificial Sequence
<220> FEATURE:
<223> OTHER INFORMATION: Artificially synthesized peptide

<400> SEQUENCE: 11

Lys Gln Phe Ile Glu Asn Gly Ser Glu Phe Ala Asn Lys Leu Leu Lys
```

```
                      1               5                  10                 15
Lys Phe Ser Leu Leu Lys Pro Trp Ala Cys
            20                  25

<210> SEQ ID NO 12
<211> LENGTH: 27
<212> TYPE: PRT
<213> ORGANISM: Artificial Sequence
<220> FEATURE:
<223> OTHER INFORMATION: Artificially synthesized peptide

<400> SEQUENCE: 12

Cys Lys Gln Phe Ile Glu Asn Gly Ser Glu Phe Ala Asn Lys Leu Leu
1               5                   10                  15

Lys Lys Phe Ser Leu Leu Lys Pro Trp Ala Cys
            20                  25

<210> SEQ ID NO 13
<211> LENGTH: 25
<212> TYPE: PRT
<213> ORGANISM: Artificial Sequence
<220> FEATURE:
<223> OTHER INFORMATION: Artificially synthesized peptide

<400> SEQUENCE: 13

Lys Lys Leu Phe Gly Gly Arg Asn Asp Val Leu Arg Gln Met Met Asp
1               5                   10                  15

Arg Leu Gly Pro Lys Phe Asn Leu Phe
            20                  25

<210> SEQ ID NO 14
<211> LENGTH: 26
<212> TYPE: PRT
<213> ORGANISM: Artificial Sequence
<220> FEATURE:
<223> OTHER INFORMATION: Artificially synthesized peptide

<400> SEQUENCE: 14

Cys Lys Lys Leu Phe Gly Gly Arg Asn Asp Val Leu Arg Gln Met Met
1               5                   10                  15

Asp Arg Leu Gly Pro Lys Phe Asn Leu Phe
            20                  25

<210> SEQ ID NO 15
<211> LENGTH: 26
<212> TYPE: PRT
<213> ORGANISM: Artificial Sequence
<220> FEATURE:
<223> OTHER INFORMATION: Artificially synthesized peptide

<400> SEQUENCE: 15

Lys Lys Leu Phe Gly Gly Arg Asn Asp Val Leu Arg Gln Met Met Asp
1               5                   10                  15

Arg Leu Gly Pro Lys Phe Asn Leu Phe Cys
            20                  25

<210> SEQ ID NO 16
<211> LENGTH: 27
<212> TYPE: PRT
<213> ORGANISM: Artificial Sequence
<220> FEATURE:
<223> OTHER INFORMATION: Artificially synthesized peptide

<400> SEQUENCE: 16
```

```
Cys Lys Lys Leu Phe Gly Gly Arg Asn Asp Val Leu Arg Gln Met Met
1               5                   10                  15

Asp Arg Leu Gly Pro Lys Phe Asn Leu Phe Cys
            20                  25
```

<210> SEQ ID NO 17
<211> LENGTH: 25
<212> TYPE: PRT
<213> ORGANISM: Artificial Sequence
<220> FEATURE:
<223> OTHER INFORMATION: Artificially synthesized peptide

<400> SEQUENCE: 17

```
Lys Lys Leu Phe Gly Gly Arg Asn Asp Val Leu Arg Asn Met Met Asp
1               5                   10                  15

Arg Leu Gly Pro Lys Phe Asn Leu Phe
            20                  25
```

<210> SEQ ID NO 18
<211> LENGTH: 26
<212> TYPE: PRT
<213> ORGANISM: Artificial Sequence
<220> FEATURE:
<223> OTHER INFORMATION: Artificially synthesized peptide

<400> SEQUENCE: 18

```
Cys Lys Lys Leu Phe Gly Gly Arg Asn Asp Val Leu Arg Asn Met Met
1               5                   10                  15

Asp Arg Leu Gly Pro Lys Phe Asn Leu Phe
            20                  25
```

<210> SEQ ID NO 19
<211> LENGTH: 26
<212> TYPE: PRT
<213> ORGANISM: Artificial Sequence
<220> FEATURE:
<223> OTHER INFORMATION: Artificially synthesized peptide

<400> SEQUENCE: 19

```
Lys Lys Leu Phe Gly Gly Arg Asn Asp Val Leu Arg Asn Met Met Asp
1               5                   10                  15

Arg Leu Gly Pro Lys Phe Asn Leu Phe Cys
            20                  25
```

<210> SEQ ID NO 20
<211> LENGTH: 27
<212> TYPE: PRT
<213> ORGANISM: Artificial Sequence
<220> FEATURE:
<223> OTHER INFORMATION: Artificially synthesized peptide

<400> SEQUENCE: 20

```
Cys Lys Lys Leu Phe Gly Gly Arg Asn Asp Val Leu Arg Asn Met Met
1               5                   10                  15

Asp Arg Leu Gly Pro Lys Phe Asn Leu Phe Cys
            20                  25
```

<210> SEQ ID NO 21
<211> LENGTH: 25
<212> TYPE: PRT
<213> ORGANISM: Artificial Sequence
<220> FEATURE:
<223> OTHER INFORMATION: Artificially synthesized peptide

<400> SEQUENCE: 21

Lys Arg Phe Tyr Lys Arg Gly Ala Glu Leu Gly Lys Asn Arg Arg Lys
1               5                   10                  15

Asn Trp His Ala Gln Leu Phe Val Leu
            20                  25

<210> SEQ ID NO 22
<211> LENGTH: 26
<212> TYPE: PRT
<213> ORGANISM: Artificial Sequence
<220> FEATURE:
<223> OTHER INFORMATION: Artificially synthesized peptide

<400> SEQUENCE: 22

Cys Lys Arg Phe Tyr Lys Arg Gly Ala Glu Leu Gly Lys Asn Arg Arg
1               5                   10                  15

Lys Asn Trp His Ala Gln Leu Phe Val Leu
            20                  25

<210> SEQ ID NO 23
<211> LENGTH: 26
<212> TYPE: PRT
<213> ORGANISM: Artificial Sequence
<220> FEATURE:
<223> OTHER INFORMATION: Artificially synthesized peptide

<400> SEQUENCE: 23

Lys Arg Phe Tyr Lys Arg Gly Ala Glu Leu Gly Lys Asn Arg Arg Lys
1               5                   10                  15

Asn Trp His Ala Gln Leu Phe Val Leu Cys
            20                  25

<210> SEQ ID NO 24
<211> LENGTH: 27
<212> TYPE: PRT
<213> ORGANISM: Artificial Sequence
<220> FEATURE:
<223> OTHER INFORMATION: Artificially synthesized peptide

<400> SEQUENCE: 24

Cys Lys Arg Phe Tyr Lys Arg Gly Ala Glu Leu Gly Lys Asn Arg Arg
1               5                   10                  15

Lys Asn Trp His Ala Gln Leu Phe Val Leu Cys
            20                  25

<210> SEQ ID NO 25
<211> LENGTH: 11
<212> TYPE: PRT
<213> ORGANISM: Artificial Sequence
<220> FEATURE:
<223> OTHER INFORMATION: Artificially synthesized peptide

<400> SEQUENCE: 25

Lys Arg Phe Tyr Lys Arg Gly Ala Glu Leu Gly
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Artificially synthesized peptide

<400> SEQUENCE: 26

Cys Lys Arg Phe Tyr Lys Arg Gly Ala Glu Leu Gly

```
1               5                   10
```

<210> SEQ ID NO 27
<211> LENGTH: 12
<212> TYPE: PRT
<213> ORGANISM: Artificial Sequence
<220> FEATURE:
<223> OTHER INFORMATION: Artificially synthesized peptide

<400> SEQUENCE: 27

```
Lys Arg Phe Tyr Lys Arg Gly Ala Glu Leu Gly Cys
1               5                   10
```

<210> SEQ ID NO 28
<211> LENGTH: 13
<212> TYPE: PRT
<213> ORGANISM: Artificial Sequence
<220> FEATURE:
<223> OTHER INFORMATION: Artificially synthesized peptide

<400> SEQUENCE: 28

```
Cys Lys Arg Phe Tyr Lys Arg Gly Ala Glu Leu Gly Cys
1               5                   10
```

<210> SEQ ID NO 29
<211> LENGTH: 15
<212> TYPE: PRT
<213> ORGANISM: Artificial Sequence
<220> FEATURE:
<223> OTHER INFORMATION: Artificially synthesized peptide

<400> SEQUENCE: 29

```
Lys Arg Phe Tyr Lys Arg Gly Ala Glu Leu Gly Lys Asn Arg Arg
1               5                   10                  15
```

<210> SEQ ID NO 30
<211> LENGTH: 16
<212> TYPE: PRT
<213> ORGANISM: Artificial Sequence
<220> FEATURE:
<223> OTHER INFORMATION: Artificially synthesized peptide

<400> SEQUENCE: 30

```
Cys Lys Arg Phe Tyr Lys Arg Gly Ala Glu Leu Gly Lys Asn Arg Arg
1               5                   10                  15
```

<210> SEQ ID NO 31
<211> LENGTH: 16
<212> TYPE: PRT
<213> ORGANISM: Artificial Sequence
<220> FEATURE:
<223> OTHER INFORMATION: Artificially synthesized peptide

<400> SEQUENCE: 31

```
Lys Arg Phe Tyr Lys Arg Gly Ala Glu Leu Gly Lys Asn Arg Arg Cys
1               5                   10                  15
```

<210> SEQ ID NO 32
<211> LENGTH: 17
<212> TYPE: PRT
<213> ORGANISM: Artificial Sequence
<220> FEATURE:
<223> OTHER INFORMATION: Artificially synthesized peptide

<400> SEQUENCE: 32

```
Cys Lys Arg Phe Tyr Lys Arg Gly Ala Glu Leu Gly Lys Asn Arg Arg
1               5                   10                  15
```

Cys

<210> SEQ ID NO 33
<211> LENGTH: 19
<212> TYPE: PRT
<213> ORGANISM: Artificial Sequence
<220> FEATURE:
<223> OTHER INFORMATION: Artificially synthesized peptide

<400> SEQUENCE: 33

Lys Arg Phe Tyr Lys Arg Gly Ala Glu Leu Gly Lys Asn Arg Lys
1               5                   10                  15

Asn Trp His

<210> SEQ ID NO 34
<211> LENGTH: 20
<212> TYPE: PRT
<213> ORGANISM: Artificial Sequence
<220> FEATURE:
<223> OTHER INFORMATION: Artificially synthesized peptide

<400> SEQUENCE: 34

Cys Lys Arg Phe Tyr Lys Arg Gly Ala Glu Leu Gly Lys Asn Arg Arg
1               5                   10                  15

Lys Asn Trp His
            20

<210> SEQ ID NO 35
<211> LENGTH: 20
<212> TYPE: PRT
<213> ORGANISM: Artificial Sequence
<220> FEATURE:
<223> OTHER INFORMATION: Artificially synthesized peptide

<400> SEQUENCE: 35

Lys Arg Phe Tyr Lys Arg Gly Ala Glu Leu Gly Lys Asn Arg Arg Lys
1               5                   10                  15

Asn Trp His Cys
            20

<210> SEQ ID NO 36
<211> LENGTH: 21
<212> TYPE: PRT
<213> ORGANISM: Artificial Sequence
<220> FEATURE:
<223> OTHER INFORMATION: Artificially synthesized peptide

<400> SEQUENCE: 36

Cys Lys Arg Phe Tyr Lys Arg Gly Ala Glu Leu Gly Lys Asn Arg Arg
1               5                   10                  15

Lys Asn Trp His Cys
            20

<210> SEQ ID NO 37
<211> LENGTH: 15
<212> TYPE: PRT
<213> ORGANISM: Artificial Sequence
<220> FEATURE:
<223> OTHER INFORMATION: Artificially synthesized peptide

<400> SEQUENCE: 37

Gly Lys Asn Arg Arg Lys Asn Trp His Ala Gln Leu Phe Val Leu
1               5                   10                  15

```
<210> SEQ ID NO 38
<211> LENGTH: 16
<212> TYPE: PRT
<213> ORGANISM: Artificial Sequence
<220> FEATURE:
<223> OTHER INFORMATION: Artificially synthesized peptide

<400> SEQUENCE: 38

Cys Gly Lys Asn Arg Arg Lys Asn Trp His Ala Gln Leu Phe Val Leu
1               5                   10                  15

<210> SEQ ID NO 39
<211> LENGTH: 16
<212> TYPE: PRT
<213> ORGANISM: Artificial Sequence
<220> FEATURE:
<223> OTHER INFORMATION: Artificially synthesized peptide

<400> SEQUENCE: 39

Gly Lys Asn Arg Arg Lys Asn Trp His Ala Gln Leu Phe Val Leu Cys
1               5                   10                  15

<210> SEQ ID NO 40
<211> LENGTH: 17
<212> TYPE: PRT
<213> ORGANISM: Artificial Sequence
<220> FEATURE:
<223> OTHER INFORMATION: Artificially synthesized peptide

<400> SEQUENCE: 40

Cys Gly Lys Asn Arg Arg Lys Asn Trp His Ala Gln Leu Phe Val Leu
1               5                   10                  15

Cys

<210> SEQ ID NO 41
<211> LENGTH: 25
<212> TYPE: PRT
<213> ORGANISM: Artificial Sequence
<220> FEATURE:
<223> OTHER INFORMATION: Artificially synthesized peptide

<400> SEQUENCE: 41

Lys Arg Phe Tyr Lys Arg Gly Ala Glu Leu Gly Lys Asn Arg Arg Lys
1               5                   10                  15

Asn Trp His Ala Asn Leu Phe Val Leu
            20                  25

<210> SEQ ID NO 42
<211> LENGTH: 26
<212> TYPE: PRT
<213> ORGANISM: Artificial Sequence
<220> FEATURE:
<223> OTHER INFORMATION: Artificially synthesized peptide

<400> SEQUENCE: 42

Cys Lys Arg Phe Tyr Lys Arg Gly Ala Glu Leu Gly Lys Asn Arg Arg
1               5                   10                  15

Lys Asn Trp His Ala Asn Leu Phe Val Leu
            20                  25

<210> SEQ ID NO 43
<211> LENGTH: 26
<212> TYPE: PRT
<213> ORGANISM: Artificial Sequence
<220> FEATURE:
```

<223> OTHER INFORMATION: Artificially synthesized peptide

<400> SEQUENCE: 43

Lys Arg Phe Tyr Lys Arg Gly Ala Glu Leu Gly Lys Asn Arg Arg Lys
1               5                   10                  15
Asn Trp His Ala Asn Leu Phe Val Leu Cys
            20                  25

<210> SEQ ID NO 44
<211> LENGTH: 27
<212> TYPE: PRT
<213> ORGANISM: Artificial Sequence
<220> FEATURE:
<223> OTHER INFORMATION: Artificially synthesized peptide

<400> SEQUENCE: 44

Cys Lys Arg Phe Tyr Lys Arg Gly Ala Glu Leu Gly Lys Asn Arg Arg
1               5                   10                  15
Lys Asn Trp His Ala Asn Leu Phe Val Leu Cys
            20                  25

<210> SEQ ID NO 45
<211> LENGTH: 15
<212> TYPE: PRT
<213> ORGANISM: Artificial Sequence
<220> FEATURE:
<223> OTHER INFORMATION: Artificially synthesized peptide

<400> SEQUENCE: 45

Gly Lys Asn Arg Arg Lys Asn Trp His Ala Gln Leu Phe Val Leu
1               5                   10                  15

<210> SEQ ID NO 46
<211> LENGTH: 16
<212> TYPE: PRT
<213> ORGANISM: Artificial Sequence
<220> FEATURE:
<223> OTHER INFORMATION: Artificially synthesized peptide

<400> SEQUENCE: 46

Cys Gly Lys Asn Arg Arg Lys Asn Trp His Ala Gln Leu Phe Val Leu
1               5                   10                  15

<210> SEQ ID NO 47
<211> LENGTH: 16
<212> TYPE: PRT
<213> ORGANISM: Artificial Sequence
<220> FEATURE:
<223> OTHER INFORMATION: Artificially synthesized peptide

<400> SEQUENCE: 47

Gly Lys Asn Arg Arg Lys Asn Trp His Ala Gln Leu Phe Val Leu Cys
1               5                   10                  15

<210> SEQ ID NO 48
<211> LENGTH: 17
<212> TYPE: PRT
<213> ORGANISM: Artificial Sequence
<220> FEATURE:
<223> OTHER INFORMATION: Artificially synthesized peptide

<400> SEQUENCE: 48

Cys Gly Lys Asn Arg Arg Lys Asn Trp His Ala Gln Leu Phe Val Leu
1               5                   10                  15
Cys

<210> SEQ ID NO 49
<211> LENGTH: 15
<212> TYPE: PRT
<213> ORGANISM: Artificial Sequence
<220> FEATURE:
<223> OTHER INFORMATION: Artificially synthesized peptide

<400> SEQUENCE: 49

Ala Gln Lys Leu Leu Lys Lys Phe Ser Leu Leu Lys Pro Trp Ala
1               5                   10                  15

<210> SEQ ID NO 50
<211> LENGTH: 16
<212> TYPE: PRT
<213> ORGANISM: Artificial Sequence
<220> FEATURE:
<223> OTHER INFORMATION: Artificially synthesized peptide

<400> SEQUENCE: 50

Cys Ala Gln Lys Leu Leu Lys Lys Phe Ser Leu Leu Lys Pro Trp Ala
1               5                   10                  15

<210> SEQ ID NO 51
<211> LENGTH: 16
<212> TYPE: PRT
<213> ORGANISM: Artificial Sequence
<220> FEATURE:
<223> OTHER INFORMATION: Artificially synthesized peptide

<400> SEQUENCE: 51

Ala Gln Lys Leu Leu Lys Lys Phe Ser Leu Leu Lys Pro Trp Ala Cys
1               5                   10                  15

<210> SEQ ID NO 52
<211> LENGTH: 17
<212> TYPE: PRT
<213> ORGANISM: Artificial Sequence
<220> FEATURE:
<223> OTHER INFORMATION: Artificially synthesized peptide

<400> SEQUENCE: 52

Cys Ala Gln Lys Leu Leu Lys Lys Phe Ser Leu Leu Lys Pro Trp Ala
1               5                   10                  15

Cys

<210> SEQ ID NO 53
<211> LENGTH: 15
<212> TYPE: PRT
<213> ORGANISM: Artificial Sequence
<220> FEATURE:
<223> OTHER INFORMATION: Artificially synthesized peptide

<400> SEQUENCE: 53

Ala Asn Lys Leu Leu Lys Lys Phe Ser Leu Leu Lys Pro Trp Ala
1               5                   10                  15

<210> SEQ ID NO 54
<211> LENGTH: 16
<212> TYPE: PRT
<213> ORGANISM: Artificial Sequence
<220> FEATURE:
<223> OTHER INFORMATION: Artificially synthesized peptide

<400> SEQUENCE: 54

Cys Ala Asn Lys Leu Leu Lys Lys Phe Ser Leu Leu Lys Pro Trp Ala

<210> SEQ ID NO 55
<211> LENGTH: 16
<212> TYPE: PRT
<213> ORGANISM: Artificial Sequence
<220> FEATURE:
<223> OTHER INFORMATION: Artificially synthesized peptide

<400> SEQUENCE: 55

Ala Asn Lys Leu Leu Lys Lys Phe Ser Leu Leu Lys Pro Trp Ala Cys
1               5                   10                  15

<210> SEQ ID NO 56
<211> LENGTH: 17
<212> TYPE: PRT
<213> ORGANISM: Artificial Sequence
<220> FEATURE:
<223> OTHER INFORMATION: Artificially synthesized peptide

<400> SEQUENCE: 56

Cys Ala Asn Lys Leu Leu Lys Lys Phe Ser Leu Leu Lys Pro Trp Ala
1               5                   10                  15

Cys

<210> SEQ ID NO 57
<211> LENGTH: 9
<212> TYPE: PRT
<213> ORGANISM: Artificial Sequence
<220> FEATURE:
<223> OTHER INFORMATION: Artificially synthesized peptide

<400> SEQUENCE: 57

Ala Gln Lys Leu Leu Lys Lys Phe Ser
1               5

<210> SEQ ID NO 58
<211> LENGTH: 10
<212> TYPE: PRT
<213> ORGANISM: Artificial Sequence
<220> FEATURE:
<223> OTHER INFORMATION: Artificially synthesized peptide

<400> SEQUENCE: 58

Cys Ala Gln Lys Leu Leu Lys Lys Phe Ser
1               5                   10

<210> SEQ ID NO 59
<211> LENGTH: 10
<212> TYPE: PRT
<213> ORGANISM: Artificial Sequence
<220> FEATURE:
<223> OTHER INFORMATION: Artificially synthesized peptide

<400> SEQUENCE: 59

Ala Gln Lys Leu Leu Lys Lys Phe Ser Cys
1               5                   10

<210> SEQ ID NO 60
<211> LENGTH: 11
<212> TYPE: PRT
<213> ORGANISM: Artificial Sequence
<220> FEATURE:
<223> OTHER INFORMATION: Artificially synthesized peptide

<400> SEQUENCE: 60

```
Cys Ala Gln Lys Leu Leu Lys Lys Phe Ser Cys
1               5                   10
```

<210> SEQ ID NO 61
<211> LENGTH: 138
<212> TYPE: PRT
<213> ORGANISM: Homo sapiens

<400> SEQUENCE: 61

```
Met Lys Phe Thr Thr Leu Leu Phe Leu Ala Ala Val Ala Gly Ala Leu
1               5                   10                  15

Val Tyr Ala Glu Asp Ala Ser Ser Asp Ser Thr Gly Ala Asp Pro Ala
            20                  25                  30

Gln Glu Ala Gly Thr Ser Lys Pro Asn Glu Glu Ile Ser Gly Pro Ala
        35                  40                  45

Glu Pro Ala Ser Pro Pro Glu Thr Thr Thr Ala Gln Glu Thr Ser
    50                  55                  60

Ala Ala Ala Val Gln Gly Thr Ala Lys Val Thr Ser Ser Arg Gln Glu
65              70                  75                  80

Leu Asn Pro Leu Lys Ser Ile Val Glu Lys Ser Ile Leu Leu Thr Glu
                85                  90                  95

Gln Ala Leu Ala Lys Ala Gly Lys Gly Met His Gly Val Pro Gly
            100                 105                 110

Gly Lys Gln Phe Ile Glu Asn Gly Ser Glu Phe Ala Gln Lys Leu Leu
        115                 120                 125

Lys Lys Phe Ser Leu Leu Lys Pro Trp Ala
    130                 135
```

<210> SEQ ID NO 62
<211> LENGTH: 19
<212> TYPE: PRT
<213> ORGANISM: Artificial Sequence
<220> FEATURE:
<223> OTHER INFORMATION: Artificially synthesized peptide

<400> SEQUENCE: 62

```
Lys Gln Phe Ile Glu Asn Gly Ser Glu Phe Ala Gln Lys Leu Leu Lys
1               5                   10                  15

Lys Phe Ser
```

<210> SEQ ID NO 63
<211> LENGTH: 39
<212> TYPE: PRT
<213> ORGANISM: Artificial Sequence
<220> FEATURE:
<223> OTHER INFORMATION: Artificially synthesized peptide

<400> SEQUENCE: 63

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35
```

COMPOSITIONS AND METHODS FOR PROMOTING ISLET VIABILITY AND ENHANCING INSULIN SECRETION

CROSS-REFERENCE TO RELATED APPLICATIONS

This application is a U.S. National Phase Application of PCT International Patent Application No. PCT/US2020/022822, filed Mar. 13, 2020, incorporated herein by reference in its entirety and which claims the benefit of U.S. Provisional Patent Application Ser. No. 62/817,790, filed Mar. 13, 2019, the disclosure of which incorporated herein by reference in its entirety.

GOVERNMENT INTEREST

This invention was made with government support under Grant Nos. EY024327 and EY026171 awarded by The National Institutes of Health. The government has certain rights in the invention.

BACKGROUND

At least 8.5% of the world's population suffers from diabetes, with prevalence rising (Tatum et al., 2017). Types 1 and 2 diabetes feeds global drug sales totaling $31 billion in 2016, with an expected increase to $45 billion by 2021. Most are injectable forms of insulin or are designed to increase incretins to counter elevated blood or inhibit sodium-glucose cotransporter 2 via oral tablets or injectables. Global sales of the equally large device market such as for insulin pumps and continuous glucose monitors are expected to exceed $35 billion by 2024. Although both approaches can be helpful, diabetics continue to suffer from a markedly elevated risk of stroke, heart attack, kidney failure, limb amputation, and blindness associated with diabetic peripheral neuropathies, nephropathy, and blood vessel damage.

Attempts to reverse the root cause biological deficiencies experienced by diabetics are ongoing, but have met with limited success. For example, regeneration of diabetic islets would be transformative, but research in this area is at a very early stage, and do not address neural innervation. Molecules that may modulate beta cell replication, for example, have been identified, but have yet to be successfully deployed in the clinic. Such molecules include certain DYRK1A kinase inhibitors that facilitate calcineurin-dependent NFAT dephosphorylation, a prerequisite for NFAT nuclear translocation to serve as a transcription factor for beta cell replication (Wang et al., 2015a). Also, the molecules PIAA and amlexanox that suppress TBK1/IKKε to activate mTOR and in turn beta cell replication have been identified in zebrafish (Xu et al., 2018). Genetic restoration of mTOR in the Akita model of neonatal diabetes also triggers beta cell replication (Riahi et al., 2018).

SUMMARY

This Summary lists several embodiments of the presently disclosed subject matter, and in many cases lists variations and permutations of these embodiments of the presently disclosed subject matter. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

In some embodiments, the presently disclosed subject matter relates to methods for regenerating glucose-stimulated insulin secretion. In some embodiments, the methods comprise contacting pancreatic islets in vitro, ex vivo, and/or in vivo with an effective amount of a composition comprising a peptide and/or a pharmaceutically acceptable salt thereof, and/or a biologically active fragment, analog, or derivative thereof, wherein the peptide, the pharmaceutically acceptable salt thereof, and/or the biologically active fragment, analog, or derivative thereof comprises, consists essentially of, or consists of an amino acid sequence comprising, consisting essentially of, or consisting of any of SEQ ID NOs: 1-60, or any combination thereof.

In some embodiments, the presently disclosed subject matter also relates to methods for regenerating viability and/or cell proliferation of transplanted or endogenous pancreatic islets. In some embodiments, the methods comprise contacting pancreatic islets prior to, concurrently with, and/or subsequent to transplantation or without transplantation in diabetics, with an effective amount of a composition comprising a peptide and/or a pharmaceutically acceptable salt thereof, and/or a biologically active fragment, analog, or derivative thereof, wherein the peptide, the pharmaceutically acceptable salt thereof, and/or the biologically active fragment, analog, or derivative thereof comprises, consists essentially of, or consists of an amino acid sequence comprising, consisting essentially of, or consisting of any of SEQ ID NOs: 1-60, or any combination thereof, wherein the viability and/or proliferation of transplanted pancreatic islets, or endogenous islets, is regenerated relative to that of an islet cell that had not been contacted with the effective amount of the composition.

In some embodiments, the presently disclosed subject matter also relates to methods for preventing and/or inhibiting rejection of a transplanted pancreatic islets, or preventing further degeneration of endogenous pancreatic islets. In some embodiments, the methods comprise contacting isolated pancreatic islets prior to, concurrently with, and/or subsequent to transplantation, or contacting endogenous diabetic islets, with an effective amount of a composition comprising a peptide and/or a pharmaceutically acceptable salt thereof, and/or a biologically active fragment, analog, or derivative thereof, wherein the peptide, the pharmaceutically acceptable salt thereof, and/or the biologically active fragment, analog, or derivative thereof comprises, consists essentially of, or consists of an amino acid sequence comprising, consisting essentially of, or consisting of any of SEQ ID NOs: 1-60, or any combination thereof, wherein rejection of the transplanted islet cell is prevented and/or inhibited relative to that of an islet cell that had not been contacted with the effective amount of the composition.

In some embodiments, the presently disclosed subject matter also relates to methods for pancreatic islet transplantation. In some embodiments, the methods comprise transplanting pancreatic islets into a transplant recipient, wherein islets have been contacted prior to, concurrently with, and/or subsequent to the transplanting step with an effective amount of a composition comprising a peptide and/or a pharmaceutically acceptable salt thereof, and/or a biologically active fragment, analog, or derivative thereof, wherein the peptide, the pharmaceutically acceptable salt thereof, and/or the biologically active fragment, analog, or derivative thereof comprises, consists essentially of, or consists of an amino acid sequence comprising, consisting essentially of, or consisting of any of SEQ ID NOs: 1-60, or any combination thereof, wherein rejection of the transplanted pancreatic islet cell is prevented and/or inhibited relative to that of an pancreatic islet cell that had not been contacted with the effective amount of the composition.

In some embodiments, the presently disclosed subject matter relates to methods for restoring health to nerves supplying pancreatic islets. In some embodiments, the methods comprise contacting nerves of pancreatic islets in vitro, ex vivo, and/or in vivo with an effective amount of a composition comprising a peptide and/or a pharmaceutically acceptable salt thereof, and/or a biologically active fragment, analog, or derivative thereof, wherein the peptide, the pharmaceutically acceptable salt thereof, and/or the biologically active fragment, analog, or derivative thereof comprises, consists essentially of, or consists of an amino acid sequence comprising, consisting essentially of, or consisting of any of SEQ ID NOs: 1-60, or any combination thereof.

In some embodiments, the presently disclosed subject matter also relates to methods for treating a symptom of a condition, disorder, or disease associated with abnormal insulin responsiveness to glucose in a subject, optionally wherein the condition, disorder, or disease is type 1 or 2 diabetes. In some embodiments, the methods comprise administering to the subject an effective amount of a composition comprising a peptide and/or a pharmaceutically acceptable salt thereof, and/or a biologically active fragment, analog, or derivative thereof, wherein the peptide, the pharmaceutically acceptable salt thereof, and/or the biologically active fragment, analog, or derivative thereof comprises, consists essentially of, or consists of an amino acid sequence comprising, consisting essentially of, or consisting of any of SEQ ID NOs: 1-60, or any combination thereof, wherein rejection of the transplanted pancreatic islets is prevented and/or inhibited relative to that of an islets that had not been contacted with the effective amount of the composition.

In some embodiments of the presently disclosed methods, the composition is formulated for administration to a subject, optionally a human subject, by intravenous, intramuscular, oral, intranasal, and/or transdermal delivery. In some embodiments, the composition is formulated as nanoparticle, a nanovesicle, a microparticle, a microvesicle, a liposome, packaged in PEG, lyophilized in pill form, or any combination thereof.

In some embodiments of the presently disclosed methods, the peptide, the pharmaceutically acceptable salt thereof, and/or the biologically active fragment, analog, or derivative thereof is comprises at least one modification selected from the group consisting of N- and/or C-terminal amidation, N- and/or C-terminal acylation, N- and/or C-terminal acetylation, addition of an N- and/or a C-terminal cysteine, pegylation, and combinations thereof. In some embodiments, the pegylation comprises addition of a PEG group to an N-terminal cysteine, a C-terminal cysteine, or both. In some embodiments, the PEG group has a molecular weight of about 1 kiloDalton (kDa) to about 40 kDa. In some embodiments, the N-terminal amidation, the C-terminal amidation, or both comprises with a substituted amide and/or the N-terminal acylation, the C-terminal acylation, or both comprises a substituted acyl group.

In some embodiments of the presently disclosed methods, the composition is free of any type of enzymatic, chemical, or biochemical molecule capable of breakdown of the peptide at its termini that is sequential degradation of the peptide, the pharmaceutically acceptable salt thereof, and/or the biologically active fragment, analog, or derivative thereof at a terminal end thereof in the absence of the N- and/or C-terminal amidation, the N- and/or C-terminal acylation, the N- and/or C-terminal acetylation, the addition of an N- and/or a C-terminal cysteine, the pegylation, or the combination thereof.

In some embodiments of the presently disclosed methods, the composition is stabilized against any type of enzymatic, chemical, or biochemical breakdown of the peptide at its termini that is sequential degradation of the wherein the peptide, the pharmaceutically acceptable salt thereof, and/or the biologically active fragment, analog, or derivative thereof at a terminal end thereof in the absence of the N- and/or C-terminal amidation, the N- and/or C-terminal acylation, the N- and/or C-terminal acetylation, the addition of an N- and/or a C-terminal cysteine, the pegylation, or the combination thereof.

In some embodiments of the presently disclosed methods, the composition is stabilized against any type of enzymatic, chemical, or biochemical breakdown of the peptide at its component amino acid side chains wherein the peptide, the pharmaceutically acceptable salt thereof, and/or the biologically active fragment, analog, or derivative thereof is stabilized in a helical structure by the N- and/or C-terminal amidation, the N- and/or C-terminal acylation, the N- and/or C-terminal acetylation, the addition of an N- and/or a C-terminal cysteine, the pegylation, or the combination thereof.

In some embodiments of the presently disclosed methods, the composition further comprises a pharmaceutically acceptable carrier, excipient, diluent, tonicity agents, viscosity building agents, and/or encapsulation, and further wherein the composition is formulated for administration to subject in need thereof by systemic, oral, or transdermal delivery, optionally wherein the subject in need thereof is a human.

In some embodiments of the presently disclosed methods, the peptide, the pharmaceutically acceptable salt thereof, and/or the biologically active fragment, analog, or derivative thereof is present in the composition at a concentration of 1.0 nM to 100 µM.

In some embodiments of the presently disclosed methods, the composition further comprises one or more stabilizing agents, wherein the one or more stabilizing agents stabilizes the peptide, the pharmaceutically acceptable salt thereof, the biologically active fragment, the analog, and/or the derivative thereof against degradation and/or stabilizes the peptide, the pharmaceutically acceptable salt thereof, the biologically active fragment, the analog, and/or the derivative thereof in a particular conformation to enhance its chemical stability. In some embodiments, the stabilizing agent comprises Tyloxapol.

In some embodiments of the presently disclosed methods, the subject has a disease, disorder, or condition associated with abnormal responsiveness to glucose. In some embodiments, the disease, disorder, or condition associated with abnormal responsiveness to glucose is type 1 or type 2 diabetes. In some embodiments, the presently disclosed methods further comprise administering to the subject one or more additional anti-diabetes therapies. In some embodiments, the one or more additional anti-diabetes therapies are selected from the group consisting of an immune therapy, optionally an immune therapy comprising administering IgM; administration of a calcineurin inhibitor, optionally Tacrolimus; administration of a glucagon-like peptide-1 (GLP-1) analog, optionally exendin-4; and any combination thereof.

In some embodiments of the presently disclosed methods, the composition is formulated for use in a human and/or wherein the pancreatic islet cell is a human islet cell, and/or wherein the pancreatic islet cell is present within a subject In some embodiments, the presently disclosed subject matter also relates to compositions for use in regenerating pancreatic islet viability and/or cell proliferation in vitro, ex vivo, and/or in vivo. In some embodiments, the composition comprises, consists essentially of, or consists of a peptide and/or a pharmaceutically acceptable salt thereof, and/or a biologically active fragment, analog, or derivative thereof, wherein the peptide, the pharmaceutically acceptable salt thereof, and/or the biologically active fragment, analog, or derivative thereof comprises, consists essentially of, or consists of an amino acid sequence comprising, consisting essentially of, or consisting of any of SEQ ID NOs: 1-60, or any combination thereof.

In some embodiments, the presently disclosed subject matter also relates to compositions for use in regenerating pancreatic islet viability and/or cell proliferation in vitro, ex vivo, and/or in vivo; and/or for regenerating glucose-stimulated insulin secretion; and/or for regenerating viability and/or cell proliferation of transplanted islets; and/or for preventing and/or inhibiting rejection of a transplanted islets; and/or for islet transplantation; and/or for treating a symptom of a condition, disorder, or disease associated with abnormal insulin responsiveness to glucose in subjects. In some embodiments, the composition comprises, consists essentially of, or consists of a peptide and/or a pharmaceutically acceptable salt thereof, and/or a biologically active fragment, analog, or derivative thereof, wherein the peptide, the pharmaceutically acceptable salt thereof, and/or the biologically active fragment, analog, or derivative thereof comprises, consists essentially of, or consists of an amino acid sequence comprising, consisting essentially of, or consisting of any of SEQ ID NOs: 1-60, or any combination thereof.

In some embodiments, the presently disclosed subject matter also relates to compositions for preparation of a medicament for regenerating pancreatic islet viability and/or cell proliferation in vitro, ex vivo, and/or in vivo; and/or for regenerating glucose-stimulated insulin secretion; and/or for regenerating viability and/or cell proliferation of a transplanted pancreatic islets; and/or for preventing and/or inhibiting rejection of a transplanted islets; and/or for pancreatic islet transplantation; and/or for treating a symptom of a condition, disorder, or disease associated with abnormal insulin responsiveness to glucose in a subject. In some embodiments, the composition comprises, consists essentially of, or consists of a peptide and/or a pharmaceutically acceptable salt thereof, and/or a biologically active fragment, analog, or derivative thereof, wherein the peptide, the pharmaceutically acceptable salt thereof, and/or the biologically active fragment, analog, or derivative thereof comprises, consists essentially of, or consists of an amino acid sequence comprising, consisting essentially of, or consisting of any of SEQ ID NOs: 1-60, or any combination thereof.

In some embodiments of the presently disclosed subject matter, the compositions are formulated for administration to a subject, optionally a human subject, by intravenous, intramuscular, oral, intranasal, and/or transdermal delivery.

In some embodiments of the presently disclosed subject matter, the compositions are formulated as nanoparticle, a nanovesicle, a microparticle, a microvesicle, a liposome, packaged in PEG, lyophilized in pill form, or any combination thereof.

In some embodiments of the presently disclosed subject matter, the peptide, the pharmaceutically acceptable salt thereof, and/or the biologically active fragment, analog, or derivative thereof is comprises at least one modification selected from the group consisting of N- and/or C-terminal amidation, N- and/or C-terminal acylation, N- and/or C-terminal acetylation, addition of an N- and/or a C-terminal cysteine, pegylation, and combinations thereof. In some embodiments, the pegylation comprises addition of a PEG group to an N-terminal cysteine, a C-terminal cysteine, or both. In some embodiments, the PEG group has a molecular weight of about 1 kiloDalton (kDa) to about 40 kDa. In some embodiments, the N-terminal amidation, the C-terminal amidation, or both comprises with a substituted amide and/or the N-terminal acylation, the C-terminal acylation, or both comprises a substituted acyl group.

In some embodiments of the presently disclosed subject matter, wherein the compositions are is free of any type of enzymatic, chemical, or biochemical molecule capable of breakdown of the peptide at its termini that is sequential degradation of the peptide, the pharmaceutically acceptable salt thereof, and/or the biologically active fragment, analog, or derivative thereof at a terminal end thereof in the absence of the N- and/or C-terminal amidation, the N- and/or C-terminal acylation, the N- and/or C-terminal acetylation, or the combination thereof.

In some embodiments of the presently disclosed subject matter, wherein the compositions further comprise a pharmaceutically acceptable carrier, excipient, diluent or encapsulation, and further wherein the composition is formulated for administration to subject in need thereof by systemic, oral, or transdermal delivery, optionally wherein the subject in need thereof is a human.

In some embodiments of the presently disclosed subject matter, wherein the peptide, the pharmaceutically acceptable salt thereof, and/or the biologically active fragment, analog, or derivative thereof is present in the composition at a concentration of 1.0 nM to 100 µM.

In some embodiments of the presently disclosed subject matter, the composition further comprises one or more pharmaceutically acceptable carriers, diluents, excipients, tonicity agents, and/or viscosity building agents. In some embodiments, the composition further comprises one or more stabilizing agents, wherein the one or more stabilizing agents stabilizes the peptide, the pharmaceutically acceptable salt thereof, the biologically active fragment, the analog, and/or the derivative thereof against degradation and/or stabilizes the peptide, the pharmaceutically acceptable salt thereof, the biologically active fragment, the analog, and/or the derivative thereof in a particular conformation to enhance its chemical stability. In some embodiments, the stabilizing agent comprises Tyloxapol.

In some embodiments of the presently disclosed subject matter, the compositions are formulated for use in a human and/or wherein the pancreatic islet cell is a human islet cell, and/or wherein the pancreatic islet cell is present within a subject.

Accordingly, it is an object of the presently disclosed subject matter to provide compositions and methods for regenerating pancreatic islet viability and/or cell proliferation in vitro, ex vivo, and/or in vivo; and/or for regenerating glucose-stimulated insulin secretion; and/or for regenerating viability and/or cell proliferation of a transplanted pancreatic islets; and/or for preventing and/or inhibiting rejection of a transplanted islets; and/or for pancreatic islet transplantation; and/or for treating a symptom of a condition, disorder, or disease associated with abnormal insulin responsiveness to glucose. This and other objects are achieved in whole or in part by the presently disclosed subject matter. Further, objects of the presently disclosed subject matter having been stated above, other objects and advantages of the presently disclosed subject matter will become apparent to those skilled in the art after a study of the following description, Figures, and EXAMPLES. Additionally, various aspects and embodiments of the presently disclosed subject matter are described in further detail below.

BRIEF DESCRIPTION OF THE FIGURES

FIG. 9A is a series of immunofluorescence micrographs to analyze markers for sensory neurons on cells at day 0, day 10 and day 21. FIG. 9B is a series of bar graphs presenting the results of analyzing mRNA levels of TRPM8, TUJ1, and PMCA genes on day 0, day 10 and day 18 and analyzed by qRT-PCR. FIG. 9C is a bar graph of percent cell viability at day 21 of sensory neurons incubated with IFN-γ (1000 U/mL)+TNF-α (100 ng/mL) with or without 1 mM of the N-94/C-6 peptide or the negative control C-95 peptide for 72 hours in a 96-well plate. Data are expressed as bars of mean±standard deviation (SD) from pools of 3 independent experiments with **p<0.001.

BRIEF DESCRIPTION OF THE SEQUENCE LISTING

Figure 1A:
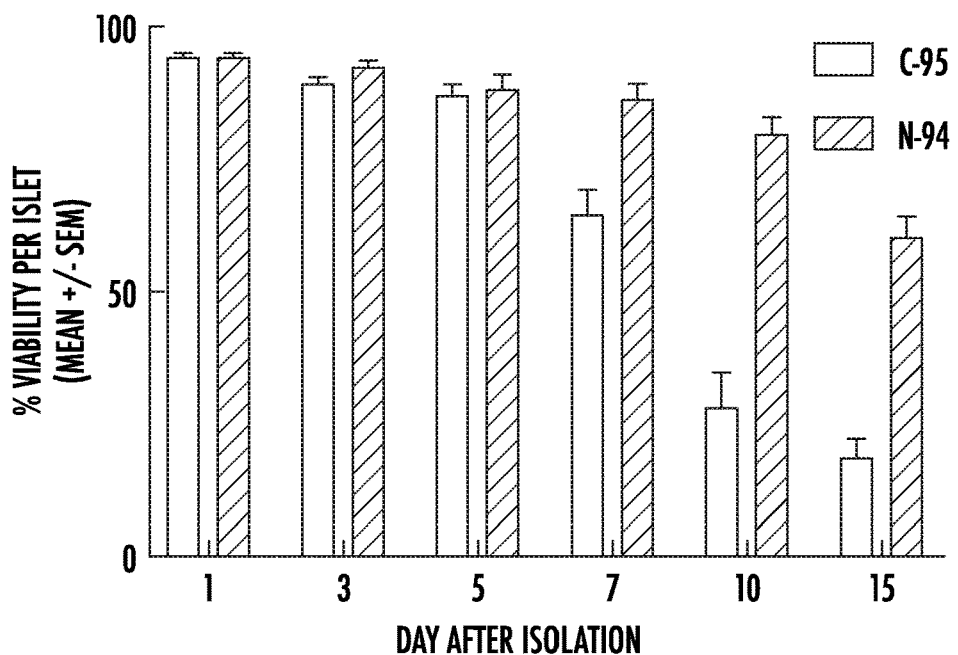
FIGS. 1A and 1B are bar graphs of isolated mouse pancreatic islets showing that 4 μM of N-94 peptide, but not 4 μM control peptide C-95 promotes mouse islet viability (FIG. 1A; N-94 peptide left bar of each pair; C-95 peptide the right bar of each pair) and glucose-dependent insulin secretion (FIG. 1B; basal level left bar of each triad; N-94 peptide center bar of each triad; C-95 peptide right bar of each triad) in vitro. Treatment for the latter was 24 hours after islet isolation. Low: 2.8 mM glucose; High: 28 mM glucose.

SEQ ID NOs: 1-60 and 62 are the amino acid sequences of exemplary peptides of the presently disclosed subject matter.

SEQ ID NO: 61 is the amino acid sequence of a human lacritin gene product.

SEQ ID NO: 63 is the amino acid sequence of exendin-4.

DETAILED DESCRIPTION

I. General Considerations

There are currently no approved therapies available that address the causes, drivers, or underlying pathology of diabetes, including in particular Type 1 Diabetes (T1D). The only therapies currently approved for T1D address insulin replacement, blood glucose monitoring, insulin action, and organ transplant. T1D is characterized as the progression towards and state of insulin deficiency caused by an immune-mediated loss of functional insulin producing beta cells. During this process, various factors (genetic, environmental, and immune), either alone or in combination, induce a state of stress in the beta cell that results in loss of beta cell function and cell death, both leading to insulin deficiency and a life-long dependence on insulin replacement therapy.

Therapies that directly modify beta cell biology can stop the loss of function and number of insulin producing cells that occurs in T1D and increase their number when they have been lost. Recent studies suggest that impairment of beta cell function is an early feature of disease pathogenesis while a decrease in beta cell mass occurs more closely to clinical manifestation. Beta cells are not merely passive victims in the development of T1D, but pathological beta cell stress occurs very early in the course of T1D and plays a role in the loss of beta cell function and mass in T1D, conceivably by triggering or potentiating the beta cell-specific autoimmune response. The dynamic nature of the beta cell population continues to be revealed. In the healthy pancreas, this population is heterogeneous in both function and phenotype: exhibiting fluctuations in levels of insulin secretion and endoplasmic reticulum stress, for example.

Beta cell survival therapies can delay and halt the progression of T1D in all stages of the disease: preserving insulin independence for individuals with no beta cell loss, preventing insulin dependence in those with asymptomatic loss of beta cell mass, and maintaining residual beta cell mass in those already insulin dependent. Survival therapies also have utility in protecting regenerated or replaced beta cell mass in order to achieve insulin independence. Beta cell survival therapies nurture and protect the cells' number and function as they experience the stressors unique to T1D.

Recent clinical findings have bolstered the validity of approaches to enhance beta cell survival. Separately, both Gleevec and Verapamil were shown to delay or slow the loss of insulin production in stage 3 adults, improve their glucose control, and reduce the incidence of diabetic ketoacidosis Loss of beta cell function occurs early in the T1D disease process and precedes the loss of beta cell mass. In addition, dysfunctional beta cells can be found in many people with longstanding T1D. Inappropriate hormone processing, cellular senescence, and other indicators of diminished beta cell function have all been recently described to occur in the T1D prodrome. Strategies to improve beta cell function can be incorporated into approaches tailored towards increasing beta cell mass. Functional and dysfunctional beta cells can be detected prior to diagnosis and decades after the initial T1D diagnosis, indicating a need for therapies directed at increasing residual mass and function at all stages of disease. Strategies to increase beta cell mass can be approached with respect to proliferation, differentiation from other cell types, and/or new growth.

Beta cell survival and beta cell regeneration therapies, in some embodiments combined with appropriate immune therapies, can alter the course of T1D to prevent, halt, and in some embodiments cure T1D. Beta Cell Regeneration therapies can also provide a non-invasive curative option for people living with T1D by providing therapeutics that increase the number and function of a person's own remaining beta cells.

There are two basic strategies to cure the beta cell deficiency in T1D: (1) implant insulin producing cells into the individual (Beta Cell Replacement); and (2) treat the individual with agents that increase the number and function of insulin producing cells in their body (Beta Cell Regeneration). Beta Cell Replacement strategies are characterized by various benefits, but also have their shortcomings. Regenerative therapies, on the other hand, can result in stage 3 individuals achieving improved glucose control and eventually insulin independence. Such therapies are designed to replenish beta cell mass and/or improve residual cell function in stage 2 individuals preventing onset of insulin dependence. Both Beta Cell Regeneration and Replacement strategies can also be combined with a strategy to combat the auto- or transplant directed-immune response against the beta cell.

Testing of beta cell directed (and other curative) therapies in T1D has been reliant on a single clinical trial design and a single clinical outcome: preservation of meal stimulated insulin secretion 1 year after the start of an intervention. This makes testing of candidate therapies expensive and prolonged, and highlights a need to better enable clinical development of therapies. Recent application of "platform" trial designs, combination treatment regimens, particular patient subpopulations (e.g., testing of agents in the most clinically relevant patient population (stage 2 versus stage 3)), and innovative therapeutic readouts aim to address this gap. Similarly, the application of continuous glucose monitoring devices in T1D trials might provide a useful and early measure of drug efficacy for those agents that, by maintaining or increasing beta cell mass, result in an improvement in glucose control.

As disclosed herein, the N-94 synthetic peptide restores beta cell capability in islets to thereby reverse disease in streptozotocin diabetic mice, in keeping with the conservation of lacritin signaling machinery in islets. Such machinery includes NFAT and mTOR. Like harmine and INDY, lacritin promotes nuclear translocation of NFAT, and like PIAA and amlexanox it activates mTOR—both to promote HSG/HeLa proliferation (Wang et al., 2006) and healing of wounded NOD mouse eyes (Wang et al., 2015b). It does so via its C-terminal N-94 domain. Lacritin C-terminal N-94 is also responsible for restoring health to inflamed eyes in two different models of autoimmune dry eye disease via: (1) rapid stimulation of autophagy to capture inflammation damaged proteins and organelles, and 2) restoration of oxidative phosphorylation (Wang et al., 2013). This is primarily through FOXO1 and FOXO3 signaling. That N-94-like peptides are constituent residents of plasma suggest that islets are continuously bathed in them, and per dry eye (Karnati et al., 2013) may be selectively deficient in diabetes.

Transplantation of N-94-treated islets requires surgical intervention. In some embodiments, regeneration of endogenous islets is provided by via systemic [self-] treatment.

I. Definitions

In describing and claiming the presently disclosed subject matter, the following terminology will be used in accordance with the definitions set forth below.

The articles "a" and "an" are used herein to refer to one or to more than one (i.e., to at least one) of the grammatical object of the article. By way of example, "an element" means one element or more than one element.

The term "about", as used herein, means approximately, in the region of, roughly, or around. When the term "about" is used in conjunction with a numerical range, it modifies that range by extending the boundaries above and below the numerical values set forth. For example, in some embodiments, the term "about" is used herein to modify a numerical value above and below the stated value by a variance of 10%. Therefore, about 50% means in the range of 45%-55%. Numerical ranges recited herein by endpoints include all numbers and fractions subsumed within that range (e.g., 1 to 5 includes 1, 1.5, 2, 2.75, 3, 3.90, 4, and 5). It is also to be understood that all numbers and fractions thereof are presumed to be modified by the term "about".

As used herein, the phrase "biological sample" refers to a sample isolated from a subject (e.g., a biopsy, blood, serum, etc.) or from a cell or tissue from a subject (e.g., RNA and/or DNA and/or a protein or polypeptide isolated therefrom). Biological samples can be of any biological tissue or fluid or cells from any organism as well as cells cultured in vitro, such as cell lines and tissue culture cells. Frequently the sample will be a "clinical sample" which is a sample derived from a subject (i.e., a subject undergoing a diagnostic procedure and/or a treatment). Typical clinical samples include, but are not limited to cerebrospinal fluid, serum, plasma, blood, saliva, skin, muscle, olfactory tissue, lacrimal fluid, synovial fluid, nail tissue, hair, feces, urine, a tissue or cell type, and combinations thereof, tissue or fine needle biopsy samples, and cells therefrom. Biological samples can also include sections of tissues, such as frozen sections or formalin fixed sections taken for histological purposes.

As used herein, term "comprising", which is synonymous with "including," "containing", or "characterized by", is inclusive or open-ended and does not exclude additional, unrecited elements and/or method steps. "Comprising" is a term of art used in claim language which means that the named elements are present, but other elements can be added and still form a composition or method within the scope of the presently disclosed subject matter. By way of example and not limitation, a pharmaceutical composition comprising a particular active agent and a pharmaceutically acceptable carrier can also contain other components including, but not limited to other active agents, other carriers and excipients, and any other molecule that might be appropriate for inclusion in the pharmaceutical composition without any limitation.

As used herein, the phrase "consisting of" excludes any element, step, or ingredient that is not particularly recited in the claim. When the phrase "consists of" appears in a clause of the body of a claim, rather than immediately following the preamble, it limits only the element set forth in that clause; other elements are not excluded from the claim as a whole. By way of example and not limitation, a pharmaceutical composition consisting of an active agent and a pharmaceutically acceptable carrier contains no other components besides the particular active agent and the pharmaceutically acceptable carrier. It is understood that any molecule that is below a reasonable level of detection is considered to be absent.

As used herein, the phrase "consisting essentially of" limits the scope of a claim to the specified materials or steps, plus those that do not materially affect the basic and novel characteristic(s) of the claimed subject matter. By way of example and not limitation, a pharmaceutical composition consisting essentially of an active agent and a pharmaceutically acceptable carrier contains active agent and the pharmaceutically acceptable carrier, but can also include any additional elements that might be present but that do not materially affect the biological functions of the composition in vitro or in vivo.

With respect to the terms "comprising", "consisting essentially of", and "consisting of", where one of these three terms is used herein, the presently disclosed and claimed subject matter encompasses the use of either of the other two terms. For example, "comprising" is a transitional term that is broader than both "consisting essentially of" and "consisting of", and thus the term "comprising" implicitly encompasses both "consisting essentially of" and "consisting of". Likewise, the transitional phrase "consisting essentially of" is broader than "consisting of", and thus the phrase "consisting essentially of" implicitly encompasses "consisting of".

As used herein, the term "biologically active fragments" or "bioactive fragment" of the polypeptides encompasses natural or synthetic portions of the full-length protein that are capable of specific binding to their natural ligand or of performing the function of the protein.

As used herein, the term "lacritin polypeptide" and the like terms is defined as any peptide comprising the amino acid sequence SEQ ID NO: 1 and or a biologically active fragment, homolog, or derivative thereof. As used herein, the term "biologically active fragments" or "bioactive fragment" of a lacritin polypeptide encompasses natural or synthetic portions of the amino acid sequence MKFTTLLFLAAVAGALVYAEDASSDSTGADPAQEAGTSKPNEEISGPAEPASPPET TTTAQETSAAAVQGTAKVTSSRQELNPLKSIVEKSILLTEQALAKAGKGMHGGVP GGKQFIENGSEFAQKLLKKFSLLKPWA (SEQ ID NO: 61). Fragments of lacritin (SEQ ID NO: 61) include, for example: KQFIENGSEFAQKLLKKFS (SEQ ID NO: 62; 'N-94/C-6'; Wang et al., 2006) and KQFIENGSEFAQKLLKKFSLLKPWA (SEQ ID NO: 1; 'N-94'; see Zhang et al., 2013.

As used herein an "acylated" amino acid is an amino acid comprising an acyl group which is non-native to a naturally occurring amino acid, regardless by the means by which it is produced. Exemplary methods of producing acylated amino acids and acylated peptides are known in the art and include acylating an amino acid before inclusion in the peptide or peptide synthesis followed by chemical acylation of the peptide. In some embodiments, the acyl group causes the peptide to have one or more of (i) a prolonged half-life in circulation, (ii) a delayed onset of action, (iii) an extended duration of action, and (iv) an improved resistance to proteases.

As used herein, an "alkylated" amino acid is an amino acid comprising an alkyl group which is non-native to a naturally occurring amino acid, regardless of the means by which it is produced. Exemplary methods of producing alkylated amino acids and alkylated peptides are known in the art and including alkylating an amino acid before inclusion in the peptide or peptide synthesis followed by chemical alkylation of the peptide. Without being held to any particular theory, it is believed that alkylation of peptides will achieve similar, if not the same, effects as acylation of the peptides, e.g., a prolonged half-life in circulation, a delayed onset of action, an extended duration of action, and an improved resistance to proteases.

As used herein, the phrase "enhancing survival" refers to decreasing the amount of death, or the rate of death, in a cell population (e.g., an islet cell population). Enhancing survival can be due to preventing cell death alone (e.g., cell death in conjunction with apoptosis), or decreasing the rate of cell death. The decrease in cell death can also result from indirect effects such as inducing proliferation of some cells, such indirect effect effectively replenishing at least some or all of a population of cells as they die Enhancing survival of cells can also be accomplished by a combination of inducing proliferation and decreasing cell death, or the rate of cell death. "Promoting survival" and "enhancing survivability" are used interchangeably with "enhancing survival" herein.

The term "identity" as used herein relates to the similarity between two or more sequences. Identity is measured by dividing the number of identical residues by the total number of residues and multiplying the product by 100 to achieve a percentage. Thus, two copies of exactly the same sequence have 100% identity, whereas two sequences that have amino acid/nucleic acid deletions, additions, or substitutions relative to one another have a lower degree of identity. Those skilled in the art will recognize that several computer programs, such as those that employ algorithms such as BLAST (Basic Local Alignment Search Tool, Altschul et al., 1993) are available for determining sequence identity.

As used herein an amino acid "modification" refers to a substitution of an amino acid, or the derivation of an amino acid by the addition and/or removal of chemical groups to/from the amino acid, and includes substitution with any of the 20 amino acids commonly found in human proteins, as well as atypical or non-naturally occurring amino acids. Commercial sources of atypical amino acids include Sigma-Aldrich (Milwaukee, Wisconsin, United States of America), ChemPep Inc. (Miami, Florida, United States of America), and Genzyme Pharmaceuticals (Cambridge, Massachusetts, United States of America). Atypical amino acids may be purchased from commercial suppliers, synthesized de novo, or chemically modified or derivatized from naturally occurring amino acids.

As used herein an amino acid "substitution" refers to the replacement of one amino acid residue by a different amino acid residue.

As used herein, the term "conservative amino acid substitution" is defined herein as exchanges within one of the following five groups:

Small aliphatic, nonpolar or slightly polar residues: Ala, Ser, Thr, Pro, Gly;

Polar, negatively charged residues and their amides: Asp, Asn, Glu, Gln, cysteic acid and homocysteic acid;

Polar, positively charged residues: His, Arg, Lys; Ornithine (Orn)

Large, aliphatic, nonpolar residues: Met, Leu, Ile, Val, Cys, Norleucine (Nle), homocysteine Large, aromatic residues: Phe, Tyr, Trp, acetyl phenylalanine A "peptidomimetic" refers to a chemical compound having a structure that is different from the general structure of an existing peptide, but that functions in a manner similar to the existing peptide, e.g., by mimicking the biological activity of that peptide. Peptidomimetics typically comprise naturally-occurring amino acids and/or unnatural amino acids, but can also comprise modifications to the peptide backbone. For example a peptidomimetic may include a sequence of naturally-occurring amino acids with the insertion or substitution of a non-peptide moiety, e.g. a retroinverso fragment, or incorporation of non-peptide bonds such as an azapeptide bond (CO substituted by NH) or pseudo-peptide bond (e.g. NH substituted with $CH_2$), or an ester bond (e.g., depsipeptides, wherein one or more of the amide (—CONHR—) bonds are replaced by ester (COOR) bonds). Alternatively the peptidomimetic may be devoid of any naturally-occurring amino acids.

As used herein the term "amino acid" encompasses any molecule containing both amino and carboxyl functional groups, wherein the amino and carboxylate groups are attached to the same carbon (the alpha carbon). The alpha carbon optionally may have one or two further organic substituents. For the purposes of the present disclosure designation of an amino acid without specifying its stereochemistry is intended to encompass either the L or D form of the amino acid, or a racemic mixture. However, in the instance where an amino acid is designated by its three letter code and includes a superscript number, the D form of the amino acid is specified by inclusion of a lower case d before the three letter code and superscript number (e.g., dLys1), wherein the designation lacking the lower case d (e.g., Lys1) is intended to specify the native L form of the amino acid. In this nomenclature, the inclusion of the superscript number designates the position of the amino acid in the peptide sequence numbered consecutively from the N-terminus. The expression "amino acid" as used herein is meant to include both natural and synthetic amino acids, and both D and L amino acids. "Standard amino acid" means any of the twenty L-amino acids commonly found in naturally occurring peptides.

The term "subject" as used herein refers to a member of any invertebrate or vertebrate species. Accordingly, the term "subject" is intended to encompass any member of the Kingdom Animalia including, but not limited to the phylum Chordata (i.e., members of Classes Osteichythyes (bony fish), Amphibia (amphibians), Reptilia (reptiles), Aves (birds), and Mammalia (mammals)), and all Orders and Families encompassed therein. In some embodiments, a subject is a human.

It is noted that all genes, gene names, gene products, and other products disclosed herein are intended to correspond to orthologs or other similar products from any species for which the compositions and methods disclosed herein are applicable. Thus, the terms include, but are not limited to genes and gene products from humans and mice. It is understood that when a gene or gene product from a particular species is disclosed, this disclosure is intended to be exemplary only, and is not to be interpreted as a limitation unless the context in which it appears clearly indicates. Thus, for example, any genes specifically mentioned herein and for which Accession Nos. for various exemplary gene products disclosed in the GENBANK® biosequence database, are intended to encompass homologous and variant genes and gene products from humans and other animals including, but not limited to other mammals.

The methods of the presently disclosed subject matter are particularly useful for warm-blooded vertebrates. Thus, the presently disclosed subject matter concerns mammals and birds. More particularly contemplated is the isolation, manipulation, and use of stem cells from mammals such as humans and other primates, as well as those mammals of importance due to being endangered (such as Siberian tigers), of economic importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), rodents (such as mice, rats, and rabbits), marsupials, and horses. Also provided is the use of the disclosed methods and compositions on birds, including those kinds of birds that are endangered, kept in zoos, as well as fowl, and more particularly domesticated fowl, e.g., poultry, such as turkeys, chickens, ducks, geese, guinea fowl, and the like, as they are also of economic importance to humans. Thus, also contemplated is the isolation, manipulation, and use of stem cells from livestock, including but not limited to domesticated swine (pigs and hogs), ruminants, horses, poultry, and the like.

As used herein, the phrase "substantially" refers to a condition wherein in some embodiments no more than 50%, in some embodiments no more than 40%, in some embodiments no more than 30%, in some embodiments no more than 25%, in some embodiments no more than 20%, in some embodiments no more than 15%, in some embodiments no more than 10%, in some embodiments no more than 9%, in some embodiments no more than 8%, in some embodiments no more than 7%, in some embodiments no more than 6%, in some embodiments no more than 5%, in some embodiments no more than 4%, in some embodiments no more than 3%, in some embodiments no more than 2%, in some embodiments no more than 1%, and in some embodiments no more than 0% of the components of a collection of entities does not have a given characteristic.

The terms "additional therapeutically active compound" or "additional therapeutic agent", as used in the context of the presently disclosed subject matter, refer to the use or administration of a compound for an additional therapeutic use for a particular injury, disease, or disorder being treated. Such a compound, for example, could include one being used to treat an unrelated disease or disorder, or a disease or disorder which is not responsive to the primary treatment for the injury, disease or disorder being treated. Diseases and disorders being treated by the additional therapeutically active agent include, for example, hypertension and diabetes. The additional compounds can also be used to treat symptoms associated with the injury, disease, or disorder, including, but not limited to, pain and inflammation.

The term "adult" as used herein, is meant to refer to any non-embryonic or non-juvenile subject.

As used herein, an "agonist" is a composition of matter which, when administered to a mammal such as a human, enhances or extends a biological activity attributable to the level or presence of a target compound or molecule of interest in the subject.

A disease or disorder is "alleviated" if the severity of a symptom of the disease, condition, or disorder, or the frequency with which such a symptom is experienced by a subject, or both, are reduced.

As used herein, amino acids are represented by the full name thereof, by the three letter code corresponding thereto, or by the one-letter code corresponding thereto, as indicated in Table 1:

TABLE 1

Amino Acid Codes and Functionally Equivalent Codons

| Full Name | 3-Letter Code | 1-Letter Code | Functionally Equivalent Codons |
|---|---|---|---|
| Aspartic Acid | Asp | D | GAC; GAU |
| Glutamic Acid | Glu | E | GAA; GAG |
| Lysine | Lys | K | AAA; AAG |
| Arginine | Arg | R | AGA; AGG; CGA; CGC; CGG; CGU |
| Histidine | His | H | CAC; CAU |
| Tyrosine | Tyr | Y | UAC; UAU |
| Cysteine | Cys | C | UGC; UGU |
| Asparagine | Asn | N | AAC; AAU |
| Glutamine | Gln | Q | CAA; CAG |
| Serine | Ser | S | ACG; AGU; UCA; UCC; UCG; UCU |
| Threonine | Thr | T | ACA; ACC; ACG; ACU |
| Glycine | Gly | G | GGA; GGC; GGG; GGU |
| Alanine | Ala | A | GCA; GCC; GCG; GCU |
| Valine | Val | V | GUA; GUC; GUG; GUU |
| Leucine | Leu | L | UUA; UUG; CUA; CUC; CUG; CUU |
| Isoleucine | Ile | I | AUA; AUC; AUU |
| Methionine | Met | M | AUG |
| Proline | Pro | P | CCA; CCC; CCG; CCU |
| Phenylalanine | Phe | F | UUC; UUU |
| Tryptophan | Trp | W | UGG |

The expression "amino acid" as used herein is meant to include both natural and synthetic amino acids, and both D and L amino acids. "Standard amino acid" means any of the twenty standard L-amino acids commonly found in naturally occurring peptides. "Nonstandard amino acid residue" means any amino acid, other than the standard amino acids, regardless of whether it is prepared synthetically or derived from a natural source. As used herein, "synthetic amino acid" also encompasses chemically modified amino acids, including but not limited to, salts, amino acid derivatives (such as amides), and substitutions. Amino acids contained within the peptides of the presently disclosed subject matter, and particularly at the carboxy- or amino-terminus, can be modified by methylation, amidation, acetylation or substitution with other chemical groups which can change the peptide's circulating half-life without adversely affecting their activity. Additionally, a disulfide linkage may be present or absent in the peptides of the presently disclosed subject matter.

The term "amino acid" is used interchangeably with "amino acid residue," and can refer to a free amino acid or to an amino acid residue of a peptide. It will be apparent from the context in which the term is used whether it refers to a free amino acid or a residue of a peptide.

Amino acids can be classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group.

The term "basic" or "positively charged" amino acid, as used herein, refers to amino acids in which the R groups have a net positive charge at pH 7.0, and include, but are not limited to, the standard amino acids lysine, arginine, and histidine.

As used herein, an "analog" of a chemical compound is a compound that, by way of example, resembles another in structure but is not necessarily an isomer (e.g., 5-fluorouracil is an analog of thymine). With respect to an amino acid, an "analog" of an amino acid can in some embodiments be a different amino acid that structurally resembles the amino acid or a compound other than an amino acid that structurally resembles the amino acid. A large number of art-recognized analogs of the 20 amino acids commonly found in proteins (the "standard" amino acids) are known. With respect to a peptide, the term "analog" thus relates to peptides which differ from a reference peptide (in some embodiments a naturally-occurring peptide) by the identity or location of one or more amino acid residues, (e.g., by deletion, substitution, and/or insertion) and which share some or all of the properties of the reference peptide so long as they have a desirable characteristic of the reference peptide (e.g., a biological activity of a lacritin peptide or derivative thereof of the presently disclosed subject matter).

An "antagonist" is a composition of matter which when administered to a mammal such as a human, inhibits a biological activity attributable to the level or presence of a compound or molecule of interest in the subject.

The term "antibody", as used herein, refers to an immunoglobulin molecule which is able to specifically or selectively bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the presently disclosed subject matter can exist in a variety of forms. The term "antibody" refers to polyclonal and monoclonal antibodies and derivatives thereof (including chimeric, synthesized, humanized and human antibodies), including an entire immunoglobulin or antibody or any functional fragment of an immunoglobulin molecule which binds to the target antigen and or combinations thereof. Examples of such functional entities include complete antibody molecules, antibody fragments, such as $F_v$, single chain $F_v$, complementarity determining regions (CDRs), $V_L$ (light chain variable region), $V_H$ (heavy chain variable region), Fab, F(ab')$_2$ and any combination of those or any other functional portion of an immunoglobulin peptide capable of binding to target antigen.

Antibodies exist, e.g., as intact immunoglobulins or as a number of well characterized fragments produced by digestion with various peptidases. Thus, for example, pepsin digests an antibody below the disulfide linkages in the hinge region to produce F(ab')$_2$ a dimer of Fab which itself is a light chain joined to $V_H$-$C_{H1}$ by a disulfide bond. The F(ab')$_2$ can be reduced under mild conditions to break the disulfide linkage in the hinge region, thereby converting the F(ab')$_2$ dimer into an Fab$_1$ monomer. The Fab$_1$ monomer is essentially a Fab with part of the hinge region. While various antibody fragments are defined in terms of the digestion of an intact antibody, one of skill will appreciate that such fragments can be synthesized de novo either chemically or by utilizing recombinant DNA methodology. Thus, the term antibody, as used herein, also includes antibody fragments either produced by the modification of whole antibodies or those synthesized de novo using recombinant DNA methodologies.

An "antibody heavy chain", as used herein, refers to the larger of the two types of polypeptide chains present in all intact antibody molecules.

An "antibody light chain", as used herein, refers to the smaller of the two types of polypeptide chains present in all intact antibody molecules.

The term "single chain antibody" refers to an antibody wherein the genetic information encoding the functional fragments of the antibody are located in a single contiguous length of DNA. For a thorough description of single chain antibodies, see Bird et al., 1988; Huston et al., 1993).

The term "humanized" refers to an antibody wherein the constant regions have at least about 80% or greater homology to human immunoglobulin. Additionally, some of the nonhuman, such as murine, variable region amino acid residues can be modified to contain amino acid residues of human origin. Humanized antibodies have been referred to as "reshaped" antibodies. Manipulation of the complementarity-determining regions (CDR) is a way of achieving humanized antibodies. See for example, U.S. Pat. Nos. 4,816,567; 5,482,856; 6,479,284; 6,677,436; 7,060,808; 7,906,625; 8,398,980; 8,436,150; 8,796,439; and 10,253,111; and U.S. Patent Application Publication Nos. 2003/0017534, 2018/0298087, 2018/0312588, 2018/0346564, and 2019/0151448, each of which is incorporated by reference in its entirety.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" as used herein is defined as a molecule that provokes an immune response. This immune response can involve either antibody production, or the activation of specific immunologically-competent cells, or both. An antigen can be derived from organisms, subunits of proteins/antigens, killed or inactivated whole cells or lysates.

The term "antimicrobial agents" as used herein refers to any naturally-occurring, synthetic, or semi-synthetic compound or composition or mixture thereof, which is safe for human or animal use as practiced in the methods of the presently disclosed subject matter, and is effective in killing or substantially inhibiting the growth of microbes. "Antimicrobial" as used herein, includes antibacterial, antifungal, and antiviral agents.

As used herein, the term "antisense oligonucleotide" or antisense nucleic acid means a nucleic acid polymer, at least a portion of which is complementary to a nucleic acid which is present in a normal cell or in an affected cell. "Anti sense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence can be complementary to regulatory sequences specified on the coding strand of a DNA molecule encoding a protein, which regulatory sequences control expression of the coding sequences. The antisense oligonucleotides of the presently disclosed subject matter include, but are not limited to, phosphorothioate oligonucleotides and other modifications of oligonucleotides.

The term "autologous", as used herein, refers to something that occurs naturally and normally in a certain type of tissue or in a specific structure of the body. In transplantation, it refers to a graft in which the donor and recipient areas are in the same individual, or to blood that the donor has previously donated and then receives back, usually during surgery.

The term "basal medium", as used herein, refers to a minimum essential type of medium, such as Dulbecco's Modified Eagle's Medium, Ham's F12, Eagle's Medium, RPMI, ARB, etc., to which other ingredients can be added. The term does not exclude media which have been prepared or are intended for specific uses, but which upon modification can be used for other cell types, etc.

The term "biocompatible", as used herein, refers to a material that does not elicit a substantial detrimental response in the host.

The term "biodegradable", as used herein, means capable of being biologically decomposed. A biodegradable material differs from a non-biodegradable material in that a biodegradable material can be biologically decomposed into units which can be either removed from the biological system and/or chemically incorporated into the biological system.

The term "biological sample", as used herein, refers to samples obtained from a living organism, including skin, hair, tissue, blood, plasma, cells, sweat, and urine.

The term "bioresorbable", as used herein, refers to the ability of a material to be resorbed in vivo. "Full" resorption means that no significant extracellular fragments remain. The resorption process involves elimination of the original implant materials through the action of body fluids, enzymes, or cells. Resorbed calcium carbonate can, for example, be redeposited as bone mineral, or by being otherwise re-utilized within the body, or excreted. "Strongly bioresorbable", as the term is used herein, means that at least 80% of the total mass of material implanted is resorbed within one year.

The phrases "cell culture medium", "culture medium" (plural "media" in each case), and "medium formulation" refer to a nutritive solution for cultivating cells and may be used interchangeably.

A "conditioned medium" is one prepared by culturing a first population of cells or tissue in a medium, and then harvesting the medium. The conditioned medium (along with anything secreted into the medium by the cells) can then be used in any desired way, such as to treat a disease or disorder in a subject, or to support the growth or differentiation of a second population of cells.

A "control" cell, tissue, sample, or subject is a cell, tissue, sample, or subject of the same type as a test cell, tissue, sample, or subject. The control can, for example, be examined at precisely or nearly the same time the test cell, tissue, sample, or subject is examined. The control can also, for example, be examined at a time distant from the time at which the test cell, tissue, sample, or subject is examined, and the results of the examination of the control can be recorded so that the recorded results can be compared with results obtained by examination of a test cell, tissue, sample, or subject. The control can also be obtained from another source or similar source other than the test group or a test subject, where the test sample is obtained from a subject suspected of having a disease or disorder for which the test is being performed.

A "test" cell, tissue, sample, or subject is one being examined or treated.

A "pathoindicative" cell, tissue, or sample is one which, when present, is an indication that the animal in which the cell, tissue, or sample is located (or from which the tissue was obtained) is afflicted with a disease or disorder. By way of example, the presence of one or more breast cells in a lung tissue of an animal is an indication that the animal is afflicted with metastatic breast cancer.

A tissue "normally comprises" a cell if one or more of the cells are present in the tissue in an animal not afflicted with a disease or disorder.

A "compound", as used herein, refers to any type of substance or agent that is commonly considered a drug, or a candidate for use as a drug, combinations, and mixtures of the above, as well as polypeptides and antibodies of the presently disclosed subject matter.

"Cytokine", as used herein, refers to intercellular signaling molecules, the best known of which are involved in the regulation of mammalian somatic cells. A number of families of cytokines, both growth promoting and growth inhibitory in their effects, have been characterized including, for example, interleukins, interferons, and transforming growth factors. A number of other cytokines are known to those of skill in the art. The sources, characteristics, targets, and effector activities of these cytokines have been described.

"Chemokine", as used herein, refers to an intercellular signaling molecule involved in the chemotaxis of white blood cells, such as T cells.

The term "delivery vehicle" refers to any kind of device or material, which can be used to deliver cells in vivo or can be added to a composition comprising cells administered to an animal. This includes, but is not limited to, implantable devices, aggregates of cells, matrix materials, gels, etc.

As used herein, a "derivative" of a compound refers to a chemical compound that can be produced from another compound of similar structure in one or more steps, as in replacement of H by an alkyl, acyl, or amino group. In the context of a peptide or polypeptide sequence, a "derivative" is a peptide or polypeptide that has one or more modifications to its amino acid sequence such that it differs in at least one respect from a reference sequence (e.g., a naturally occurring peptide or polypeptide) either with respect to amino acid sequence (e.g., resulting from one or more additions, deletions, and/or amino acid substitutions) or with respect to some modification thereof. Exemplary non-limiting modifications include N- and/or C-terminal additions of one or more amino acids, in some embodiments functional amino acids (e.g., cysteine), N- and/or C-terminal amidation, N- and/or C-terminal acylation, N- and/or C-terminal acetylation, and N- and/or C-terminal pegylation.

In some embodiments, a derivative of a peptide of the presently disclosed subject matter is a stapled peptide. Stapled peptides are stabilized peptides in which one or more intramolecular crosslinkers are used to maintain the peptide in a desired configuration, for example using disulfide bonds, amide bonds, and/or carbon-carbon bonds to link amino acid side chains. The crosslinkers connect at least two amino acids of the peptide. The crosslinkers can comprise at least 5, 6, 7, 8, 9, 10, 11, or 12 consecutive carbon-carbon bonds. The crosslinkers can comprise at least 5, 6, 7, 8, 9, 10, 11, or 12 carbon atoms.

The use of the word "detect" and its grammatical variants is meant to refer to measurement of the species without quantification, whereas use of the word "determine" or "measure" with their grammatical variants are meant to refer to measurement of the species with quantification. The terms "detect" and "identify" are used interchangeably herein.

As used herein, a "detectable marker" or a "reporter molecule" is an atom or a molecule that permits the specific detection of a compound comprising the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, an "effective amount" means an amount sufficient to produce a selected effect. A "therapeutically effective amount" means an effective amount of an agent being used in treating or preventing a disease or disorder.

The term "epitope" as used herein is defined as small chemical groups on the antigen molecule that can elicit and react with an antibody. An antigen can have one or more epitopes. Most antigens have many epitopes; i.e., they are multivalent. In general, an epitope is roughly five amino acids or sugars in size. One skilled in the art understands that generally the overall three-dimensional structure, rather than the specific linear sequence of the molecule, is the main criterion of antigenic specificity.

A "fragment" or "segment" is a portion of an amino acid sequence, comprising at least one amino acid, or a portion of a nucleic acid sequence comprising at least one nucleotide. The terms "fragment" and "segment" are used interchangeably herein.

As used herein, the term "fragment", as applied to a protein or peptide, can ordinarily be at least about 3-15 amino acids in length, at least about 15-25 amino acids, at least about 25-50 amino acids in length, at least about 50-75 amino acids in length, at least about 75-100 amino acids in length, and greater than 100 amino acids in length.

As used herein, the term "fragment" as applied to a nucleic acid, may ordinarily be at least about 20 nucleotides in length, typically, at least about 50 nucleotides, more typically, from about 50 to about 100 nucleotides, in some embodiments, at least about 100 to about 200 nucleotides, in some embodiments, at least about 200 nucleotides to about 300 nucleotides, yet in some embodiments, at least about 300 to about 350, in some embodiments, at least about 350 nucleotides to about 500 nucleotides, yet in some embodiments, at least about 500 to about 600, in some embodiments, at least about 600 nucleotides to about 620 nucleotides, yet in some embodiments, at least about 620 to about 650, and most in some embodiments, the nucleic acid fragment will be greater than about 650 nucleotides in length.

As used herein, a "functional" molecule is a molecule in a form in which it exhibits a property or activity by which it is characterized.

As used herein, a "functional biological molecule" is a biological molecule in a form in which it exhibits a property by which it is characterized. A functional enzyme, for example, is one which exhibits the characteristic catalytic activity by which the enzyme is characterized.

The term "ingredient" refers to any compound, whether of chemical or biological origin, that can be used in cell culture media to maintain or promote the proliferation, survival, or differentiation of cells. The terms "component", "nutrient", "supplement", and ingredient" can be used interchangeably and are all meant to refer to such compounds. Typical non-limiting ingredients that are used in cell culture media include amino acids, salts, metals, sugars, lipids, nucleic acids, hormones, vitamins, fatty acids, proteins, and the like. Other ingredients that promote or maintain cultivation of cells ex vivo can be selected by those of skill in the art, in accordance with the particular need.

The term "inhibit", as used herein, refers to the ability of a compound, agent, or method to reduce or impede a described function, level, activity, rate, etc., based on the context in which the term "inhibit" is used. In some embodiments, inhibition is by at least 10%, in some embodiments by at least 25%, in some embodiments by at least 50%, and in some embodiments, the function is inhibited by at least 75%. The term "inhibit" is used interchangeably with "reduce" and "block".

The term "inhibitor" as used herein, refers to any compound or agent, the application of which results in the inhibition of a process or function of interest, including, but not limited to, differentiation and activity. Inhibition can be inferred if there is a reduction in the activity or function of interest.

As used herein "injecting or applying" includes administration of a compound or composition of the presently disclosed subject matter by any number of routes and approaches including, but not limited to, topical, oral, buccal, intravenous, intratumoral, intramuscular, intra-arterial, intramedullary, intrathecal, intraventricular, transdermal, subcutaneous, intraperitoneal, intranasal, enteral, topical, sublingual, vaginal, ophthalmic, pulmonary, or rectal means.

As used herein, "injury" generally refers to damage, harm, or hurt; usually applied to damage inflicted on the body by an external force.

As used herein, an "instructional material" includes a publication, a recording, a diagram, or any other medium of expression, which can be used to communicate the usefulness of the composition of the presently disclosed subject matter in the kit for effecting alleviation of the various diseases or disorders recited herein. Optionally, or alternately, the instructional material may describe one or more methods of alleviating the diseases or disorders in a cell or a tissue of a mammal. The instructional material of the kit of the presently disclosed subject matter may, for example, be affixed to a container, which contains the identified compound presently disclosed subject matter, or be shipped together with a container, which contains the identified compound. Alternatively, the instructional material can be shipped separately from the container with the intention that the instructional material and the compound be used cooperatively by the recipient.

Used interchangeably herein are the terms "isolate" and "select".

The terms "isolate", "isolated", "isolating", and grammatical variations thereof when used in reference to cells, refers to a single cell of interest, or a population of cells of interest, at least partially isolated from other cell types or other cellular material with which it occurs in a culture or a tissue of origin. A sample is "substantially pure" when it is in some embodiments at least 60%, in some embodiments at least 75%, in some embodiments at least 90%, and, in certain cases, in some embodiments at least 99% free of cells or other cellular material other than the cells of interest.

An "isolated nucleic acid" refers to a nucleic acid segment or fragment, which has been separated from sequences, which flank it in a naturally occurring state, e.g., a DNA fragment that has been removed from the sequences, which are normally adjacent to the fragment, e.g., the sequences adjacent to the fragment in a genome in which it naturally occurs. The term also applies to nucleic acids, which have been substantially purified, from other components, which naturally accompany the nucleic acid, e.g., RNA or DNA, or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA, which is part of a hybrid gene encoding additional polypeptide sequence.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

As used herein, a "ligand" is a compound that specifically binds to a target compound. A ligand (e.g., an antibody) "specifically binds to" or "is specifically immunoreactive with" a compound when the ligand functions in a binding reaction which is determinative of the presence of the compound in a sample of heterogeneous compounds. Thus, under designated assay (e.g., immunoassay) conditions, the ligand binds preferentially to a particular compound and does not bind to a significant extent to other compounds present in the sample. For example, an antibody specifically binds under immunoassay conditions to an antigen bearing an epitope against which the antibody was raised. A variety of immunoassay formats may be used to select antibodies specifically immunoreactive with a particular antigen. For example, solid-phase ELISA immunoassays are routinely used to select monoclonal antibodies specifically immunoreactive with an antigen. See Harlow & Lane, 1988 for a description of immunoassay formats and conditions that can be used to determine specific immunoreactivity.

A "receptor" is a compound that specifically or selectively binds to a ligand.

As used herein, the term "linkage" refers to a connection between two groups. The connection can be either covalent or non-covalent, including but not limited to ionic bonds, hydrogen bonding, and hydrophobic/hydrophilic interactions.

As used herein, the term "linker" refers to a molecule or bivalent group derived therefrom that joins two other molecules covalently or noncovalently, e.g., through ionic or hydrogen bonds or van der Waals interactions.

The term "measuring the level of expression" or "determining the level of expression" as used herein refers to any measure or assay which can be used to correlate the results of the assay with the level of expression of a gene or protein of interest. Such assays include measuring the level of mRNA, protein levels, etc. and can be performed by assays such as northern and western blot analyses, binding assays, immunoblots, etc. The level of expression can include rates of expression and can be measured in terms of the actual amount of an mRNA or protein present. Such assays are coupled with processes or systems to store and process information and to help quantify levels, signals, etc. and to digitize the information for use in comparing levels.

Micro-RNAs are generally about 16-25 nucleotides in length. In some embodiments, miRNAs are RNA molecules of 22 nucleotides or less in length. These molecules have been found to be highly involved in the pathology of several types of cancer. Although the miRNA molecules are generally found to be stable when associated with blood serum and its components after EDTA treatment, introduction of locked nucleic acids (LNAs) to the miRNAs via PCR further increases stability of the miRNAs. LNAs are a class of nucleic acid analogs in which the ribose ring is "locked" by a methylene bridge connecting the 2'-O atom and the 4'-C atom of the ribose ring, which increases the molecule's affinity for other molecules. miRNAs are species of small non-coding single-stranded regulatory RNAs that interact with the 3'-untranslated region (3'-UTR) of target mRNA molecules through partial sequence homology. They participate in regulatory networks as controlling elements that direct comprehensive gene expression. Bioinformatics analysis has predicted that a single miRNA can regulate hundreds of target genes, contributing to the combinational and subtle regulation of numerous genetic pathways.

The term "modulate", as used herein, refers to changing the level of an activity, function, or process. The term "modulate" encompasses both inhibiting and stimulating an activity, function, or process. The term "modulate" is used interchangeably with the term "regulate" herein.

The term "nucleic acid" typically refers to large polynucleotides. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine, and uracil).

As used herein, the term "nucleic acid" encompasses RNA as well as single and double stranded DNA and cDNA. Furthermore, the terms, "nucleic acid", "DNA", "RNA" and similar terms also include nucleic acid analogs, i.e. analogs having other than a phosphodiester backbone. For example, the so called "peptide nucleic acids", which are known in the art and have peptide bonds instead of phosphodiester bonds in the backbone, are considered within the scope of the presently disclosed subject matter. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine, and uracil). Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences".

The term "nucleic acid construct", as used herein, encompasses DNA and RNA sequences encoding the particular gene or gene fragment desired, whether obtained by genomic or synthetic methods.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) in which "U" replaces "T".

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, intratumoral, and kidney dialytic infusion techniques.

"Permeation enhancement" and "permeation enhancers" as used herein relate to the process and added materials which bring about an increase in the permeability of skin to a poorly skin permeating pharmacologically active agent, i.e., so as to increase the rate at which the drug permeates through the skin and enters the bloodstream. "Permeation enhancer" is used interchangeably with "penetration enhancer".

The term "pharmaceutical composition" shall mean a composition comprising at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

As used herein, the term "pharmaceutically-acceptable carrier" means a chemical composition with which an appropriate compound or derivative can be combined and which, following the combination, can be used to administer the appropriate compound to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

As used herein the term "pharmaceutically acceptable salt" refers to salts of compounds that retain the biological activity of the parent compound, and which are not biologically or otherwise undesirable. Many of the compounds disclosed herein are capable of forming acid and/or base salts by virtue of the presence of amino and/or carboxyl groups or groups similar thereto.

As used herein, the term "hydrophilic moiety" refers to any compound that is readily water-soluble or readily absorbs water, and which are tolerated in vivo by mammalian species without toxic effects (i.e. are biocompatible). Examples of hydrophilic moieties include polyethylene glycol (PEG), polylactic acid, polyglycolic acid, a polylactic-polyglycolic acid copolymer, polyvinyl alcohol, polyvinylpyrrolidone, polymethoxazoline, polyethyloxazoline, polyhydroxyethyl methacrylate, polyhydroxypropyl methacrylamide, polymethacrylamide, polydimethylacrylamide, and derivatised celluloses such as hydroxymethylcellulose or hydroxyethylcellulose and co-polymers thereof, as well as natural polymers including, for example, albumin, heparin and dextran.

"Plurality" means at least two.

A "polynucleotide" means a single strand or parallel and anti-parallel strands of a nucleic acid. Thus, a polynucleotide may be either a single-stranded or a double-stranded nucleic acid.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof.

"Synthetic peptides or polypeptides" means a non-naturally occurring peptide or polypeptide. Synthetic peptides or polypeptides can be synthesized, for example, using an automated polypeptide synthesizer. Various solid phase peptide synthesis methods are known to those of skill in the art.

The term "prevent", as used herein, means to stop something from happening, or taking advance measures against something possible or probable from happening. In the context of medicine, "prevention" generally refers to action taken to decrease the chance of getting a disease or condition.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

A "prophylactic" treatment is a treatment administered to a subject who does not exhibit signs of a disease or injury or exhibits only early signs of the disease or injury for the purpose of decreasing the risk of developing pathology associated with the disease or injury.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a promoter which drives expression of a gene to which it is operably linked, in a constant manner in a cell. By way of example, promoters which drive expression of cellular housekeeping genes are considered to be constitutive promoters.

An "inducible" promoter is a nucleotide sequence which, when operably linked with a polynucleotide which encodes or specifies a gene product, causes the gene product to be produced in a living cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living cell substantially only if the cell is a cell of the tissue type corresponding to the promoter.

As used herein, "protecting group" with respect to a terminal amino group refers to a terminal amino group of a peptide, which terminal amino group is coupled with any of various amino-terminal protecting groups traditionally employed in peptide synthesis. Such protecting groups include, for example, acyl protecting groups such as formyl, acetyl, benzoyl, trifluoroacetyl, succinyl, and methoxysuccinyl; aromatic urethane protecting groups such as benzyloxycarbonyl; and aliphatic urethane protecting groups, for example, tert-butoxycarbonyl or adamantyloxycarbonyl. See Gross & Mienhofer, 1981 for suitable protecting groups.

As used herein, "protecting group" with respect to a terminal carboxy group refers to a terminal carboxyl group of a peptide, which terminal carboxyl group is coupled with any of various carboxyl-terminal protecting groups. Such protecting groups include, for example, tert-butyl, benzyl, or other acceptable groups linked to the terminal carboxyl group through an ester or ether bond.

The term "protein" typically refers to large polypeptides. Conventional notation is used herein to portray polypeptide sequences: the left-hand end of a polypeptide sequence is the amino-terminus; the right-hand end of a polypeptide sequence is the carboxyl-terminus.

The term "protein regulatory pathway", as used herein, refers to both the upstream regulatory pathway which regulates a protein, as well as the downstream events which that protein regulates. Such regulation includes, but is not limited to, transcription, translation, levels, activity, posttranslational modification, and function of the protein of interest, as well as the downstream events which the protein regulates.

The terms "protein pathway" and "protein regulatory pathway" are used interchangeably herein.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide can serve a non-coding function (e.g., promoter, origin of replication, ribosome-binding site, etc.), as well.

A host cell that comprises a recombinant polynucleotide is referred to as a "recombinant host cell". A gene which is expressed in a recombinant host cell wherein the gene comprises a recombinant polynucleotide, produces a "recombinant polypeptide".

A "recombinant polypeptide" is one which is produced upon expression of a recombinant polynucleotide.

The term "regulate" refers to either stimulating or inhibiting a function or activity of interest.

As used herein, term "regulatory elements" is used interchangeably with "regulatory sequences" and refers to promoters, enhancers, and other expression control elements, or any combination of such elements.

A "reversibly implantable" device is one which can be inserted (e.g., surgically or by insertion into a natural orifice of the animal) into the body of an animal and thereafter removed without great harm to the health of the animal.

A "sample", as used herein, refers in some embodiments to a biological sample from a subject, including, but not limited to, normal tissue samples, diseased tissue samples, biopsies, blood, saliva, feces, semen, tears, and urine. A sample can also be any other source of material obtained from a subject which contains cells, tissues, or fluid of interest. A sample can also be obtained from cell or tissue culture.

A "significant detectable level" is an amount of contaminate that would be visible in the presented data and would need to be addressed/explained during analysis of the forensic evidence.

By the term "signal sequence" is meant a polynucleotide sequence which encodes a peptide that directs the path a polypeptide takes within a cell, i.e., it directs the cellular processing of a polypeptide in a cell, including, but not limited to, eventual secretion of a polypeptide from a cell. A signal sequence is a sequence of amino acids which are typically, but not exclusively, found at the amino terminus of a polypeptide which targets the synthesis of the polypeptide to the endoplasmic reticulum. In some instances, the signal peptide is proteolytically removed from the polypeptide and is thus absent from the mature protein.

By "small interfering RNAs (siRNAs)" is meant, inter alia, an isolated dsRNA molecule comprised of both a sense and an anti-sense strand. In some embodiments, it is greater than 10 nucleotides in length. siRNA also refers to a single transcript which has both the sense and complementary antisense sequences from the target gene, e.g., a hairpin. siRNA further includes any form of dsRNA (proteolytically cleaved products of larger dsRNA, partially purified RNA, essentially pure RNA, synthetic RNA, recombinantly produced RNA) as well as altered RNA that differs from naturally occurring RNA by the addition, deletion, substitution, and/or alteration of one or more nucleotides.

As used herein, the term "secondary antibody" refers to an antibody that binds to the constant region of another antibody (the primary antibody).

As used herein, the term "single chain variable fragment" (scFv) refers to a single chain antibody fragment comprised of a heavy and light chain linked by a peptide linker. In some cases, scFv are expressed on the surface of an engineered cell, for the purpose of selecting particular scFv that bind to an antigen of interest.

The terms "solid support", "surface" and "substrate" are used interchangeably and refer to a structural unit of any size, where said structural unit or substrate has a surface suitable for immobilization of molecular structure or modification of said structure and said substrate is made of a material such as, but not limited to, metal, metal films, glass, fused silica, synthetic polymers, and membranes.

By the term "specifically binds", as used herein, is meant a molecule which recognizes and binds a specific molecule, but does not substantially recognize or bind other molecules in a sample, or it means binding between two or more molecules as in part of a cellular regulatory process, where said molecules do not substantially recognize or bind other molecules in a sample.

The term "standard", as used herein, refers to something used for comparison. For example, it can be a known standard agent or compound which is administered and used for comparing results when administering a test compound, or it can be a standard parameter or function which is measured to obtain a control value when measuring an effect of an agent or compound on a parameter or function. "Standard" can also refer to an "internal standard", such as an agent or compound which is added at known amounts to a sample and which is useful in determining such things as purification or recovery rates when a sample is processed or subjected to purification or extraction procedures before a marker of interest is measured. Internal standards are often but are not always limited to, a purified marker of interest which has been labeled, such as with a radioactive isotope, allowing it to be distinguished from an endogenous substance in a sample.

The term "stimulate" as used herein, means to induce or increase an activity or function level such that it is higher relative to a control value. The stimulation can be via direct or indirect mechanisms. In some embodiments, the activity or function is stimulated by at least 10% compared to a control value, in some embodiments by at least 25%, and in some embodiments by at least 50%. The term "stimulator" as used herein, refers to any composition, compound or agent, the application of which results in the stimulation of a process or function of interest.

A "subject" of diagnosis or treatment is an animal, including a human. It also includes pets and livestock.

As used herein, a "subject in need thereof" is a patient, animal, mammal, or human, who will benefit from a method or compositions of the presently disclosed subject matter.

The term "substantially pure" describes a compound, molecule, or the like, which has been separated from components which naturally accompany it. Typically, a compound is substantially pure when at least 10%, more in some embodiments at least 20%, more in some embodiments at least 50%, more in some embodiments at least 60%, more in some embodiments at least 75%, more in some embodiments at least 90%, and most in some embodiments at least 99% of the total material (by volume, by wet or dry weight, or by mole percent or mole fraction) in a sample is the compound of interest. Purity can be measured by any appropriate method, such as but not limited to in the case of polypeptides by column chromatography, gel electrophoresis, or HPLC analysis. A compound, e.g., a protein, is also substantially purified when it is essentially free of naturally associated components or when it is separated from the native contaminants which accompany it in its natural state.

A "surface active agent" or "surfactant" is a substance that has the ability to reduce the surface tension of materials and enable penetration into and through materials.

The term "symptom", as used herein, refers to any morbid phenomenon or departure from the normal in structure, function, or sensation, experienced by the patient and indicative of disease. In contrast, a "sign" is objective evidence of disease. For example, a bloody nose is a sign. It is evident to the patient, doctor, nurse, and other observers.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

"Tissue" means (1) a group of similar cell united perform a specific function; (2) a part of an organism consisting of an aggregate of cells having a similar structure and function; or (3) a grouping of cells that are similarly characterized by their structure and function, such as muscle or nerve tissue.

The term "topical application", as used herein, refers to administration to a surface, such as the skin. This term is used interchangeably with "cutaneous application" in the case of skin. A "topical application" is a "direct application".

By "transdermal" delivery is meant delivery by passage of a drug through the skin or mucosal tissue and into the bloodstream. Transdermal also refers to the skin as a portal for the administration of drugs or compounds by topical application of the drug or compound thereto. "Transdermal" is used interchangeably with "percutaneous".

The term "transfection" is used interchangeably with the terms "gene transfer", "transformation", and "transduction", and means the intracellular introduction of a polynucleotide. "Transfection efficiency" refers to the relative amount of the transgene taken up by the cells subjected to transfection. In practice, transfection efficiency is estimated by the amount of the reporter gene product expressed following the transfection procedure.

As used herein, the term "transgene" means an exogenous nucleic acid sequence comprising a nucleic acid which encodes a promoter/regulatory sequence operably linked to nucleic acid which encodes an amino acid sequence, which exogenous nucleic acid is encoded by a transgenic mammal.

As used herein, the term "treating" may include prophylaxis of the specific injury, disease, disorder, or condition, or alleviation of the symptoms associated with a specific injury, disease, disorder, or condition and/or preventing or eliminating said symptoms. A "prophylactic" treatment is a treatment administered to a subject who does not exhibit signs of a disease or exhibits only early signs of the disease for the purpose of decreasing the risk of developing pathology associated with the disease. "Treating" is used interchangeably with "treatment" herein.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer or delivery of nucleic acid to cells, such as, for example, polylysine compounds, liposomes, and the like. Examples of viral vectors include, but are not limited to, adenoviral vectors, adeno-associated virus vectors, retroviral vectors, recombinant viral vectors, and the like. Examples of non-viral vectors include, but are not limited to, liposomes, polyamine derivatives of DNA and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

The term "peptide" encompasses a sequence of 3 or more amino acids wherein the amino acids are naturally occurring or synthetic (non-naturally occurring) amino acids. Peptide mimetics include peptides having one or more of the following modifications:

1. peptides wherein one or more of the peptidyl —C(O)NR— linkages (bonds) have been replaced by a non-peptidyl linkage such as a —CH$_2$-carbamate linkage (—CH$_2$OC(O)NR—), a phosphonate linkage, a —CH$_2$-sulfonamide (—CH$_2$—S(O)$_2$NR—) linkage, a urea (—NHC(O)NH—) linkage, a —CH$_2$— secondary amine linkage, or with an alkylated peptidyl linkage (—C(O)NR—) wherein R is C$_1$-C$_4$ alkyl;
2. peptides wherein the N-terminus is derivatized to a —NRR$_1$ group, to a —NRC(O)R group, to a —NRC(O)OR group, to a —NRS(O)$_2$R group, to a —NHC (O)NHR group where R and $R_1$ are hydrogen or $C_1$-$C_4$ alkyl with the proviso that R and R are not both hydrogen;

3. peptides wherein the C terminus is derivatized to —C(O)$R_2$ where $R_2$ is selected from the group consisting of $C_1$-$C_4$ alkoxy, and —$NR_3R_4$ where $R_3$ and $R_4$ are independently selected from the group consisting of hydrogen and $C_1$-$C_4$ alkyl.

Synthetic or non-naturally occurring amino acids refer to amino acids which do not naturally occur in vivo but which, nevertheless, can be incorporated into the peptide structures described herein. The resulting "synthetic peptide" contain amino acids other than the 20 naturally occurring, genetically encoded amino acids at one, two, or more positions of the peptides. For instance, naphthylalanine can be substituted for tryptophan to facilitate synthesis. Other synthetic amino acids that can be substituted into peptides include L-hydroxypropyl, L-3,4-dihydroxyphenylalanyl, alpha-amino acids such as L-alpha-hydroxylysyl and D-alpha-methylalanyl, L-alpha.-methylalanyl, beta-amino acids, and isoquinolyl. D amino acids and non-naturally occurring synthetic amino acids can also be incorporated into the peptides. Other derivatives include replacement of the naturally occurring side chains of the 20 genetically encoded amino acids (or any L or D amino acid) with other side chains.

The term "fusion polypeptide" or "fusion protein" refers to a chimeric protein containing a reference protein (e.g., a protein or peptide of the presently disclosed subject matter) joined at the N- and/or C-terminus to one or more heterologous sequences (e.g., a non-lacritin polypeptide). Polypeptide molecules are said to have an "amino terminus" (N terminus) and a "carboxy terminus" (C terminus) because peptide linkages occur between the backbone amino group of a first amino acid residue and the backbone carboxyl group of a second amino acid residue. The terms "N terminal" and "C terminal" in reference to polypeptide sequences refer to regions of polypeptides including portions of the N terminal and C terminal regions of the polypeptide, respectively. A sequence that includes a portion of the N terminal region of polypeptide includes amino acids predominantly from the N terminal half of the polypeptide chain, but is not limited to such sequences. For example, an N terminal sequence may include an interior portion of the polypeptide sequence including bases from both the N terminal and C terminal halves of the polypeptide. The same applies to C terminal regions. N terminal and C terminal regions may, but need not, include the amino acid defining the ultimate N terminus and C terminus of the polypeptide, respectively.

Fusion proteins may be prepared by recombinant methods or by solid phase chemical peptide synthesis methods. Such methods have been known in the art since the early 1960's (Merrifield, 1963; see also Stewart et al., 1984) and have recently been employed in commercially available laboratory peptide design and synthesis kits (Cambridge Research Biochemicals). In addition, a number of available FMOC peptide synthesis systems are available. For example, assembly of a polypeptide or fragment can be carried out on a solid support using an Applied Biosystems, Inc. Model 431A automated peptide synthesizer. Such equipment provides ready access to the peptides of the invention, either by direct synthesis or by synthesis of a series of fragments that can be coupled using other known techniques.

Peptide Modification and Preparation. Peptide preparation is described herein above and in the EXAMPLES. It will be appreciated, of course, that the proteins or peptides of the presently disclosed subject matter may incorporate amino acid residues which are modified without affecting activity. For example, the termini may be derivatized to include blocking groups, i.e. chemical substituents suitable to protect and/or stabilize the N- and C-termini from "undesirable degradation," a term meant to encompass any type of enzymatic, chemical or biochemical breakdown of the compound at its termini which is likely to affect the function of the compound, i.e. sequential degradation of the compound at a terminal end thereof.

Blocking groups include protecting groups conventionally used in the art of peptide chemistry which will not adversely affect the in vivo activities of the peptide. For example, suitable N-terminal blocking groups can be introduced by alkylation or acylation of the N-terminus. Examples of suitable N-terminal blocking groups include C1-C5 branched or unbranched alkyl groups, acyl groups such as formyl and acetyl groups, as well as substituted forms thereof, such as the acetamidomethyl (Acm) group. Desamino analogs of amino acids are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines (—$NH_2$), and mono- and di-alkylamino groups such as methylamino, ethylamino, dimethylamino, diethylamino, methylethylamino and the like are examples of C-terminal blocking groups. Descarboxylated amino acid analogues such as agmatine are also useful C-terminal blocking groups and can be either coupled to the peptide's C-terminal residue or used in place of it. Further, it will be appreciated that the free amino and carboxyl groups at the termini can be removed altogether from the peptide to yield desamino and descarboxylated forms thereof without affect on peptide activity.

Acid addition salts of the presently disclosed subject matter are also contemplated as functional equivalents. Thus, a peptide in accordance with the presently disclosed subject matter treated with an inorganic acid such as hydrochloric, hydrobromic, sulfuric, nitric, phosphoric, and the like, or an organic acid such as an acetic, propionic, glycolic, pyruvic, oxalic, malic, malonic, succinic, maleic, fumaric, tataric, citric, benzoic, cinnamie, mandelic, methanesulfonic, ethanesulfonic, p-toluenesulfonic, salicyclic and the like, to provide a water soluble salt of the peptide is suitable for use in the presently disclosed subject matter.

The presently disclosed subject matter also provides for analogs of proteins. Analogs can differ from naturally occurring proteins or peptides by conservative amino acid sequence differences or by modifications which do not affect sequence, or by both. For example, conservative amino acid changes may be made, which although they alter the primary sequence of the protein or peptide, do not normally alter its function. To that end, 10 or more conservative amino acid changes typically have no effect on peptide function.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring or non-standard synthetic amino acids. The peptides of the presently disclosed subject matter are not limited to products of any of the specific exemplary processes listed herein.

The presently disclosed subject matter includes the use of beta-alanine (also referred to as β-alanine, β-Ala, bA, and βA, having the structure:

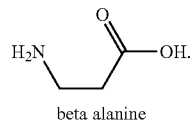

beta alanine

Sequences are provided herein which use the symbol "βA," but in the Sequence Listing submitted herewith "βA" is provided as "Xaa" and reference in the text of the Sequence Listing indicates that Xaa is beta alanine.

It will be appreciated, of course, that the polypeptides, derivatives, or fragments thereof may incorporate amino acid residues which are modified without affecting activity. For example, the termini may be derivatized to include blocking groups, i.e. chemical substituents suitable to protect and/or stabilize the N- and C-termini from "undesirable degradation," a term meant to encompass any type of enzymatic, chemical or biochemical breakdown of the compound at its termini which is likely to affect the function of the compound, i.e. sequential degradation of the compound at a terminal end thereof.

Other modifications can also be incorporated without adversely affecting the activity and these include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the presently disclosed subject matter are also contemplated, for example, inverted peptides in which all amino acids are substituted with D-amino acid forms.

Substantially pure protein obtained as described herein may be purified by following known procedures for protein purification, wherein an immunological, enzymatic or other assay is used to monitor purification at each stage in the procedure. Protein purification methods are well known in the art, and are described, for example in Deutscher et al., 1990.

As discussed, modifications or optimizations of peptide ligands of the presently disclosed subject matter are within the scope of the application. Modified or optimized peptides are included within the definition of peptide binding ligand. Specifically, a peptide sequence identified can be modified to optimize its potency, pharmacokinetic behavior, stability and/or other biological, physical and chemical properties.

Amino Acid Substitutions. In certain embodiments, the disclosed methods and compositions may involve preparing polypeptides with one or more substituted amino acid residues.

In various embodiments, the structural, physical and/or therapeutic characteristics of peptide sequences may be optimized by replacing one or more amino acid residues.

Other modifications can also be incorporated without adversely affecting the activity and these include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the presently disclosed subject matter are also contemplated, for example, inverted peptides in which all amino acids are substituted with D-amino acid forms.

The skilled artisan will be aware that, in general, amino acid substitutions in a peptide typically involve the replacement of an amino acid with another amino acid of relatively similar properties (i.e., conservative amino acid substitutions). The properties of the various amino acids and effect of amino acid substitution on protein structure and function have been the subject of extensive study and knowledge in the art.

For example, one can make the following isosteric and/or conservative amino acid changes in the parent polypeptide sequence with the expectation that the resulting polypeptides would have a similar or improved profile of the properties described above:

Substitution of alkyl-substituted hydrophobic amino acids: including alanine, leucine, isoleucine, valine, norleucine, S-2-aminobutyric acid, S-cyclohexylalanine or other simple alpha-amino acids substituted by an aliphatic side chain from C1-10 carbons including branched, cyclic and straight chain alkyl, alkenyl or alkynyl substitutions.

Substitution of aromatic-substituted hydrophobic amino acids: including phenylalanine, tryptophan, tyrosine, biphenylalanine, 1-naphthylalanine, 2-naphthylalanine, 2-benzothienylalanine, 3-benzothienylalanine, histidine, amino, alkylamino, dialkylamino, aza, halogenated (fluoro, chloro, bromo, or iodo) or alkoxy-substituted forms of the previous listed aromatic amino acids, illustrative examples of which are: 2-,3- or 4-aminophenylalanine, 2-,3- or 4-chlorophenylalanine, 2-,3- or 4-methylphenylalanine, 2-,3- or 4-methoxyphenylalanine, 5-amino-, 5-chloro-, 5-methyl- or 5-methoxytryptophan, 2'-, 3'-, or 4'-amino-, 2'-, 3'-, or 4'-chloro-, 2,3, or 4-biphenylalanine, 2',-3',- or 4'-methyl-2, 3 or 4-biphenylalanine, and 2- or 3-pyridylalanine.

Substitution of amino acids containing basic functions: including arginine, lysine, histidine, ornithine, 2,3-diaminopropionic acid, homoarginine, alkyl, alkenyl, or aryl-substituted (from C1-C10 branched, linear, or cyclic) derivatives of the previous amino acids, whether the substituent is on the heteroatoms (such as the alpha nitrogen, or the distal nitrogen or nitrogens, or on the alpha carbon, in the pro-R position for example. Compounds that serve as illustrative examples include: N-epsilon-isopropyl-lysine, 3-(4-tetrahydropyridyl)-glycine, 3-(4-tetrahydropyridyl)-alanine, N,N-gamma, gamma'-diethyl-homoarginine. Included also are compounds such as alpha methyl arginine, alpha methyl 2,3-diaminopropionic acid, alpha methyl histidine, alpha methyl ornithine where alkyl group occupies the pro-R position of the alpha carbon. Also included are the amides formed from alkyl, aromatic, heteroaromatic (where the heteroaromatic group has one or more nitrogens, oxygens, or sulfur atoms singly or in combination) carboxylic acids or any of the many well-known activated derivatives such as acid chlorides, active esters, active azolides and related derivatives) and lysine, ornithine, or 2,3-diaminopropionic acid.

Substitution of acidic amino acids: including aspartic acid, glutamic acid, homoglutamic acid, tyrosine, alkyl, aryl, arylalkyl, and heteroaryl sulfonamides of 2,4-diaminopropionic acid, ornithine or lysine and tetrazole-substituted alkyl amino acids.

Substitution of side chain amide residues: including asparagine, glutamine, and alkyl or aromatic substituted derivatives of asparagine or glutamine.

Substitution of hydroxyl containing amino acids: including serine, threonine, homoserine, 2,3-diaminopropionic acid, and alkyl or aromatic substituted derivatives of serine or threonine. It is also understood that the amino acids within each of the categories listed above can be substituted for another of the same group.

For example, the hydropathic index of amino acids may be considered (Kyte & Doolittle, 1982, J. Mol. Biol., 157: 105-132). The relative hydropathic character of the amino acid contributes to the secondary structure of the resultant protein, which in turn defines the interaction of the protein with other molecules. Each amino acid has been assigned a hydropathic index on the basis of its hydrophobicity and charge characteristics (Kyte & Doolittle, 1982), these are: isoleucine (+4.5); valine (+4.2); leucine (+3.8); phenylalanine (+2.8); cysteine/cystine (+2.5); methionine (+1.9); alanine (+1.8); glycine (-0.4); threonine (-0.7); serine (-0.8); tryptophan (-0.9); tyrosine (-1.3); proline (-1.6); histidine (-3.2); glutamate (-3.5); glutamine (-3.5); aspartate (-3.5); asparagine (-3.5); lysine (-3.9); and arginine (-4.5). In making conservative substitutions, the use of amino acids whose hydropathic indices are within +/-2 is preferred, within +/-1 are more preferred, and within +/-0.5 are even more preferred.

Amino acid substitution may also take into account the hydrophilicity of the amino acid residue (e.g., U.S. Pat. No. 4,554,101). Hydrophilicity values have been assigned to amino acid residues: arginine (+3.0); lysine (+3.0); aspartate (+3.0); glutamate (+3.0); serine (+0.3); asparagine (+0.2); glutamine (+0.2); glycine (0); threonine (-0.4); proline (-0.5.+-0.1); alanine (-0.5); histidine (-0.5); cysteine (-1.0); methionine (-1.3); valine (-1.5); leucine (-1.8); isoleucine (-1.8); tyrosine (-2.3); phenylalanine (-2.5); tryptophan (-3.4). Replacement of amino acids with others of similar hydrophilicity is preferred.

Other considerations include the size of the amino acid side chain. For example, it would generally not be preferred to replace an amino acid with a compact side chain, such as glycine or serine, with an amino acid with a bulky side chain, e.g., tryptophan or tyrosine. The effect of various amino acid residues on protein secondary structure is also a consideration. Through empirical study, the effect of different amino acid residues on the tendency of protein domains to adopt an alpha-helical, beta-sheet or reverse turn secondary structure has been determined and is known in the art (see e.g., Chou & Fasman, 1974, Biochemistry, 13:222-245; 1978, Ann. Rev. Biochem., 47: 251-276; 1979, Biophys. J., 26:367-384).

Based on such considerations and extensive empirical study, tables of conservative amino acid substitutions have been constructed and are known in the art. For example: arginine and lysine; glutamate and aspartate; serine and threonine; glutamine and asparagine; and valine, leucine and isoleucine. Alternatively: Ala (A) leu, ile, val; Arg (R) gln, asn, lys; Asn (N) his, asp, lys, arg, gln; Asp (D) asn, glu; Cys (C) ala, ser; Gln (Q) glu, asn; Glu (E) gln, asp; Gly (G) ala; His (H) asn, gln, lys, arg; Ile (I) val, met, ala, phe, leu; Leu (L) val, met, ala, phe, ile; Lys (K) gln, asn, arg; Met (M) phe, ile, leu; Phe (F) leu, val, ile, ala, tyr; Pro (P) ala; Ser (S), thr; Thr (T) ser; Trp (W) phe, tyr; Tyr (Y) trp, phe, thr, ser; Val (V) ile, leu, met, phe, ala.

Other considerations for amino acid substitutions include whether or not the residue is located in the interior of a protein or is solvent exposed. For interior residues, conservative substitutions would include: Asp and Asn; Ser and Thr; Ser and Ala; Thr and Ala; Ala and Gly; Ile and Val; Val and Leu; Leu and Ile; Leu and Met; Phe and Tyr; Tyr and Trp. (See e.g., PROWL Rockefeller University website). For solvent exposed residues, conservative substitutions would include: Asp and Asn; Asp and Glu; Glu and Gln; Glu and Ala; Gly and Asn; Ala and Pro; Ala and Gly; Ala and Ser; Ala and Lys; Ser and Thr; Lys and Arg; Val and Leu; Leu and Ile; Ile and Val; Phe and Tyr. Various matrices have been constructed to assist in selection of amino acid substitutions, such as the PAM250 scoring matrix, Dayhoff matrix, Grantham matrix, McLachlan matrix, Doolittle matrix, Henikoff matrix, Miyata matrix, Fitch matrix, Jones matrix, Rao matrix, Levin matrix and Risler matrix (Idem.)

In determining amino acid substitutions, one may also consider the existence of intermolecular or intramolecular bonds, such as formation of ionic bonds (salt bridges) between positively charged residues (e.g., His, Arg, Lys) and negatively charged residues (e.g., Asp, Glu) or disulfide bonds between nearby cysteine residues.

Methods of substituting any amino acid for any other amino acid in an encoded peptide sequence are well known and a matter of routine experimentation for the skilled artisan, for example by the technique of site-directed mutagenesis or by synthesis and assembly of oligonucleotides encoding an amino acid substitution and splicing into an expression vector construct.

The terminology used herein is for the purpose of describing the particular versions or embodiments only, and is not intended to limit the scope of the presently disclosed subject matter. All publications mentioned herein are incorporated by reference in their entirety.

II. Exemplary Compositions of the Presently Disclosed Subject Matter

As disclosed herein, compositions having lacritin-based activity are disclosed for use in the presently disclosed methods. In some embodiments, a composition is provided comprising a lacritin polypeptide, a bioactive fragment of lacritin, a non-native lacritin peptide, or peptidomimetic derivative of lacritin. In some embodiments, the composition comprises, consists essentially of, or consists of a sequence selected from the group consisting of SEQ ID NOs: 1-60, or a sequence that differs from SEQ ID NOs: 1-60 by 1, 2, 3, 4 or 5 amino acid modifications. In some embodiments, the amino acid modifications are amino acid substitutions, and in some embodiments the 1, 2, 3, 4 or 5 amino acid substitutions are conservative amino acid substitutions. In some embodiments, the composition comprises, consists essentially of, or consists of a sequence selected from the group consisting of SEQ ID NO: 62, or a sequence that differs from SEQ ID NO: 62 by 1, 2, 3, 4 or 5 amino acid modifications In some embodiments, a composition is provided comprising, consisting essentially, of consisting of a bioactive fragment of lacritin, wherein the bioactive fragment comprises, consists essentially of, or consists of a sequence selected from the group consisting of SEQ ID NOs: 1-60 or a derivative that differs therefrom by one or more amino acid substitutions. In some embodiments, the composition comprises a N-94 peptide, which is a synthetic lactrin protein fragment that has prosecretory, prosurvival, and mitogenic properties, is currently in a phase II clinical trial for autoimmune dry eye disease, and has been detected in plasma as C-terminal peptides inclusive of the N-94 sequence. As disclosed herein, islet cells are Lacritin/N-94 responsive and prominently express known elements of the N-94 receptor complex and signaling pathways. Lactrin-based peptides are disclosed in U.S. Pat. No. 10,393,755, which is incorporated by reference herein in its entirety.

II.A. Formulations

Thus, in some embodiments the presently disclosed subject matter relates to compositions, in some embodiments pharmaceutical compositions, for use in the presently disclosed methods. In some embodiments, the pharmaceutical composition comprises an effective amount of a composition as set forth herein. In some embodiments, the pharmaceutical composition comprises a peptide and/or a pharmaceutically acceptable salt thereof, and/or a biologically active fragment, analog, or derivative thereof, wherein the peptide, the pharmaceutically acceptable salt thereof, and/or the biologically active fragment, analog, or derivative thereof comprises, consists essentially of, or consists of an amino acid sequence comprising, consisting essentially of, or consisting of KQFIENGSEFAQKLLKKFSLLKPWA (SEQ ID NO: 1), KRFYKRGAELG (SEQ ID NO: 25), KRFYKRGAELGKNRR (SEQ ID NO: 29), KRFYKRGAELGKNRRKNWH (SEQ ID NO: 33), KRFYKRGAELGKNRRKNWHAQLFVL (SEQ ID NO: 21), KKLFGGRNDVLRQMMDRLGPKFNLF (SEQ ID NO: 13) or any combination thereof. In some embodiments, the derivative thereof of SEQ ID NOs: 1, 25, 29, 33, and 21 comprises, consists essentially of, or consists of an amino acid sequence comprising, consisting essentially of, or consisting of any of SEQ ID NOs: 2-4, 26-28, 30-32, 34-36, and 22-24, respectively. More particularly, the peptides of the presently disclosed subject matter are based on the N-94 peptide of SEQ ID NO: 1 and derivatives thereof, as set forth in Table 2.

TABLE 2

Exemplary Peptides of the Presently Disclosed Subject Matter

| Description* | Peptide Sequence | SEQ ID NO: |
|---|---|---|
| N-94 | KQFIENGSEFAQKLLKKFS | 1 |
| N-94[5C] | CKQFIENGSEFAQKLLKKFS | 2 |
| N-94[3C] | KQFIENGSEFAQKLLKKFSC | 3 |
| N-94[53C] | CKQFIENGSEFAQKLLKKFSC | 4 |
| N-94/Q96N | KNFIENGSEFAQKLLKKFSLLKPWA | 5 |
| N-94/Q96N[5C] | CKNFIENGSEFAQKLLKKFSLLKPWA | 6 |
| N-94/Q96N[3C] | KNFIENGSEFAQKLLKKFSLLKPWAC | 7 |
| N-94/Q96N[53C] | CKNFIENGSEFAQKLLKKFSLLKPWAC | 8 |
| N-94/Q106N | KQFIENGSEFANKLLKKFSLLKPWA | 9 |
| N-94/Q106N[5C] | CKQFIENGSEFANKLLKKFSLLKPWA | 10 |

TABLE 2-continued

Exemplary Peptides of the Presently Disclosed Subject Matter

| Description* | Peptide Sequence | SEQ ID NO: |
|---|---|---|
| N-94/Q106N[3C] | KQFIENGSEFANKLLKKFSLLKPWAC | 11 |
| N-94/Q106N[53C] | CKQFIENGSEFANKLLKKFSLLKPWAC | 12 |
| TearPep2 | KKLFGGRNDVLRQMMDRLGPKFNLF | 13 |
| TearPep2[5C] | CKKLFGGRNDVLRQMMDRLGPKFNLF | 14 |
| TearPep2[3C] | KKLFGGRNDVLRQMMDRLGPKFNLFC | 15 |
| TearPep2[53C] | CKKLFGGRNDVLRQMMDRLGPKFNLFC | 16 |
| TearPep2/Q107N | KKLFGGRNDVLRNMMDRLGPKFNLF | 17 |
| TearPep2/Q107N[5C] | CKKLFGGRNDVLRNMMDRLGPKFNLF | 18 |
| TearPep2/Q107N[3C] | KKLFGGRNDVLRNMMDRLGPKFNLFC | 19 |
| TearPep2/Q107N[53C] | CKKLFGGRNDVLRNMMDRLGPKFNLFC | 20 |
| TearPep3 | KRFYKRGAELGKNRRKNWHAQLFVL | 21 |
| TearPep3[5C] | CKRFYKRGAELGKNRRKNWHAQLFVL | 22 |
| TearPep3[3C] | KRFYKRGAELGKNRRKNWHAQLFVLC | 23 |
| TearPep3[53C] | CKRFYKRGAELGKNRRKNWHAQLFVLC | 24 |
| TearPep3/C-14 | KRFYKRGAELG | 25 |
| TearPep3/C-14[5C] | CKRFYKRGAELG | 26 |
| TearPep3/C-14[3C] | KRFYKRGAELGC | 27 |
| TearPep3/C-14[53C] | CKRFYKRGAELGC | 28 |
| TearPep3/C-10 | KRFYKRGAELGKNRR | 29 |
| TearPep3/C-10[5C] | CKRFYKRGAELGKNRR | 30 |
| TearPep3/C-10[3C] | KRFYKRGAELGKNRRC | 31 |
| TearPep3/C-10[53C] | CKRFYKRGAELGKNRRC | 32 |
| TearPep3/C-6 | KRFYKRGAELGKNRRKNWH | 33 |
| TearPep3/C-6[5C] | CKRFYKRGAELGKNRRKNWH | 34 |
| TearPep3/C-6[3C] | KRFYKRGAELGKNRRKNWHC | 35 |
| TearPep3/C-6[53C] | CKRFYKRGAELGKNRRKNWHC | 36 |
| TearPep3/N-104 | GKNRRKNWHAQLFVL | 37 |
| TearPep3/N-104[5C] | CGKNRRKNWHAQLFVL | 38 |
| TearPep3/N-104[3C] | GKNRRKNWHAQLFVLC | 39 |
| TearPep3/N-104[53C] | CGKNRRKNWHAQLFVLC | 40 |
| TearPep3/Q115N | KRFYKRGAELGKNRRKNWHANLFVL | 41 |
| TearPep3/Q115N[5C] | CKRFYKRGAELGKNRRKNWHANLFVL | 42 |
| TearPep3/Q115N[3C] | KRFYKRGAELGKNRRKNWHANLFVLC | 43 |
| TearPep3/Q115N[53C] | CKRFYKRGAELGKNRRKNWHANLFVLC | 44 |
| TearPep3/N-104/Q115N | GKNRRKNWHAQLFVL | 45 |
| TearPep3/N-104/Q115N[5C] | CGKNRRKNWHAQLFVL | 46 |

TABLE 2-continued

Exemplary Peptides of the Presently Disclosed Subject Matter

| Description* | Peptide Sequence | SEQ ID NO: |
|---|---|---|
| TearPep3/N-104/Q115N[3C] | GKNRRKNWHAQLFVLC | 47 |
| TearPep3/N-104/Q115N[53C] | CGKNRRKNWHAQLFVLC | 48 |
| N-104 | AQKLLKKFSLLKPWA | 49 |
| N-104[5C] | CAQKLLKKFSLLKPWA | 50 |
| N-104[3C] | AQKLLKKFSLLKPWAC | 51 |
| N-104[53C] | CAQKLLKKFSLLKPWAC | 52 |
| N-104/Q106N | ANKLLKKFSLLKPWA | 53 |
| N-104/Q106N[5C] | CANKLLKKFSLLKPWA | 54 |
| N-104/Q106N[3C] | ANKLLKKFSLLKPWAC | 55 |
| N-104/Q106N[53C] | CANKLLKKFSLLKPWAC | 56 |
| N-104/C-6 | AQKLLKKFS | 57 |
| N-104/C-6[5C] | CAQKLLKKFS | 58 |
| N-104/C-6[3C] | AQKLLKKFSC | 59 |
| N-104/C-6[53C] | CAQKLLKKFSC | 60 |
| N-94/+6 | KQFIENGSEFAQKLLKKFSLLKPWA | 62 |

*[5C]: peptide with an N-terminal Cys added; [3C]: peptide with a C-terminal Cys added; [53C]: peptide with an N-terminal Cys and a C-terminal Cys added.

In some embodiments, a peptide and/or a pharmaceutically acceptable salt thereof, and/or a biologically active fragment, analog, or derivative thereof of the presently disclosed subject matter can be provided in a composition that includes a carrier, particularly a pharmaceutically acceptable carrier, such as but not limited to a carrier pharmaceutically acceptable in humans. Any suitable pharmaceutical formulation can be used to prepare the compositions for administration to a subject.

For example, suitable formulations can include aqueous and non-aqueous sterile injection solutions that can contain anti-oxidants, buffers, bacteriostatics, bactericidal antibiotics, and solutes that render the formulation isotonic with the bodily fluids of the intended recipient.

It should be understood that in addition to the ingredients particularly mentioned above the formulations of the presently disclosed subject matter can include other agents conventional in the art with regard to the type of formulation in question. For example, sterile pyrogen-free aqueous and non-aqueous solutions can be used.

The methods and compositions of the presently disclosed subject matter can be used with additional adjuvants or biological response modifiers including, but not limited to, cytokines and other immunomodulating compounds.

In some embodiments, therapeutic agents, including, but not limited to, cytotoxic agents, anti-angiogenic agents, pro-apoptotic agents, antibiotics, hormones, hormone antagonists, chemokines, drugs, prodrugs, toxins, enzymes or other agents may be used as adjunct therapies when using the compositions described herein. Drugs useful in the presently disclosed subject matter may, for example, possess a pharmaceutical property selected from the group consisting of antimitotic, antikinase, alkylating, antimetabolite, antibiotic, alkaloid, anti-angiogenic, pro-apoptotic agents, and combinations thereof.

In some embodiments, the presently disclosed compositions and methods can further comprise administering to the subject at least one additional active agent (in some embodiments an immunosuppressive agent) to a subject. In some embodiments, the at least one additional immunosuppressive agent is selected from the group consisting of methotrexate, cyclophosphamide, cyclosporine, cyclosporin A, chloroquine, hydroxychloroquine, sulfasalazine (sulphasalazopyrine), a gold salt, D-penicillamine, leflunomide, azathioprine, anakinra, infliximab (REMICADE®), etanercept, a TNFα blocker, a non-steroidal anti-inflammatory drug (NSAID), or any combination thereof. In some embodiments, the NSAID is selected from the group consisting of acetyl salicylic acid, choline magnesium salicylate, diflunisal, magnesium salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, a cyclooxygenase-2 (Cox-2) inhibitor, tramadol, rapamycin (sirolimus), an analog thereof, or any combination thereof.

II.B. Administration

Suitable methods for administration of the compositions of the presently disclosed subject matter include, but are not limited to intravenous administration and delivery directly to the target tissue or organ (e.g., the abdomen and/or the pancreas). In some embodiments, the method of administration encompasses features for regionalized delivery or accumulation of the compositions of the presently disclosed subject matter at the site in need of treatment. In some embodiments, the compositions of the presently disclosed subject matter are delivered directly into the pancreas. In some embodiments, selective delivery of the compositions of the presently disclosed subject matter is accomplished by intravenous injection of compositions of the presently disclosed subject matter, where they accumulate in and/or act in the pancreas, optionally on islet cells. Other modes of administration that can be employed include topical, oral, buccal, intramuscular, intra arterial, intramedullary, intrathecal, intraventricular, transdermal, subcutaneous, intraperitoneal, intranasal, enteral, topical, sublingual, vaginal, ophthalmic, pulmonary, or rectal means. Compounds or agents of the presently disclosed subject matter can be administered to a subject by one or more of these routes when appropriate. In some embodiments, intratracheal installation, insufflation, nebulization, dry powder inhalation, aerosol inhalation, and combinations thereof are employed as a route or routes of administration of the compositions of the presently disclosed subject matter. In some embodiments, a pharmaceutical composition useful in the methods of the presently disclosed subject matter may be prepared, packaged, or sold in formulations suitable for oral, rectal, vaginal, parenteral, intravenous, topical, pulmonary, intranasal, buccal, ophthalmic, intrathecal or another route of administration. Other contemplated formulations include projected nanoparticles, liposomal preparations, resealed erythrocytes containing the active ingredient, and immunologically-based formulations. In some embodiments, an oral formulation of the presently disclosed subject matter can be packaged in PEG, or in some embodiments lyophilized in a pill form.

Where the administration of the compositions of the presently disclosed subject matter is by injection or direct application, the injection or direct application may be in a single dose or in multiple doses. Where the administration of the compositions of the presently disclosed subject matter is by infusion, the infusion may be a single sustained dose over a prolonged period of time or multiple infusions.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

A pharmaceutical composition of the presently disclosed subject matter may be prepared, packaged, or sold in bulk, as a single unit dose, or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient(s), the pharmaceutically acceptable carrier, and any additional ingredients in a pharmaceutical composition of the presently disclosed subject matter will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the presently disclosed subject matter may further comprise one or more additional pharmaceutically active agents. Particularly contemplated additional agents include anti-emetics and scavengers such as cyanide and cyanate scavengers.

Controlled- or sustained-release formulations of a pharmaceutical composition of the presently disclosed subject matter may be made using conventional technology.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the presently disclosed subject matter are known in the art and described, for example in Genaro, ed., 1985, *Remington's Pharmaceutical Sciences*, Mack Publishing Co., Easton, Pennsylvania, which is incorporated herein by reference.

In some embodiments, the composition further comprises one or more stabilizing agents, wherein the one or more stabilizing agents stabilizes the peptide, the pharmaceutically acceptable salt thereof, the biologically active fragment, the analog, and/or the derivative thereof against degradation and/or stabilizes the peptide, the pharmaceutically acceptable salt thereof, the biologically active fragment, the analog, and/or the derivative thereof in a particular conformation to enhance its chemical stability. In some embodiments, the stabilizing agent comprises Tyloxapol (see e.g., U.S. Patent Application Publication No. 2019/0381136, which is incorporated herein by reference in its entirety).

II.C. Doses

An effective dose of a composition of the presently disclosed subject matter is administered to a subject in need thereof. A "treatment effective amount" or a "therapeutic amount" is an amount of a therapeutic composition sufficient to produce a measurable response (e.g., a biologically or clinically relevant response in a subject being treated). In some embodiments, an activity that inhibits an anti-transplant immune response (e.g., transplant rejection) is measured. Actual dosage levels of active ingredients in the compositions of the presently disclosed subject matter can be varied so as to administer an amount of the active compound(s) that is effective to achieve the desired therapeutic response for a particular subject. The selected dosage level will depend upon the activity of the therapeutic composition, the route of administration, combination with other drugs or treatments, the severity of the condition being treated, and the condition and prior medical history of the subject being treated. However, it is within the skill of the art to start doses of the compound at levels lower than required to achieve the desired therapeutic effect and to gradually increase the dosage until the desired effect is achieved. The potency of a composition can vary, and therefore a "treatment effective amount" can vary. However, using generally applicable assay methods, one skilled in the art can readily assess the potency and efficacy of a candidate compound of the presently disclosed subject matter and adjust the therapeutic regimen accordingly. After review of the disclosure of the presently disclosed subject matter presented herein, one of ordinary skill in the art can tailor the dosages to an individual subject, taking into account the particular formulation, method of administration to be used with the composition, and particular disease treated. Further calculations of dose can consider subject height and weight, severity and stage of symptoms, and the presence of additional deleterious physical conditions. Such adjustments or variations, as well as evaluation of when and how to make such adjustments or variations, are well known to those of ordinary skill in the art of medicine.

As such, in some embodiments the compositions of the presently disclosed subject matter are present in a pharmaceutically acceptable carrier, which in some embodiments can be a pharmaceutically acceptable for use in humans.

Typically, dosages of the compound of the presently disclosed subject matter which may be administered to an animal, preferably a human, range in amount from 1 µg to about 100 g per kilogram of body weight of the animal. While the precise dosage administered will vary depending upon any number of factors, including but not limited to, the type of animal and type of disease state being treated, the age of the animal and the route of administration. In some embodiments, the dosage of the compound will vary from about 1 mg to about 10 g per kilogram of body weight of the animal. In some embodiments, the dosage will vary from about 10 mg to about 1 g per kilogram of body weight of the animal. In some embodiments, the peptide, the pharmaceutically acceptable salt thereof, and/or the biologically active fragment, analog, or derivative thereof is present in the composition at a concentration of 1.0 nM to 100 µM.

The compound may be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type of cancer being diagnosed, the type and severity of the condition or disease being treated, the type and age of the animal, etc.

Suitable preparations include injectables, either as liquid solutions or suspensions, however, solid forms suitable for solution in, suspension in, liquid prior to injection, may also be prepared. The preparation may also be emulsified, or the polypeptides encapsulated in liposomes. The active ingredients are often mixed with excipients which are pharmaceutically acceptable and compatible with the active ingredient. Suitable excipients are, for example, water saline, dextrose, glycerol, ethanol, or the like and combinations thereof. In addition, if desired, the vaccine preparation may also include minor amounts of auxiliary substances such as wetting or emulsifying agents, pH buffering agents, and/or adjuvants.

Thus, the presently disclosed subject matter relates to compositions for use in some embodiments for regenerating pancreatic islet viability and/or cell proliferation in vitro, ex vivo, and/or in vivo; for use in some embodiments for regenerating pancreatic islet viability and/or proliferation in vitro, ex vivo, and/or in vivo; for use in some embodiments for regenerating glucose-stimulated insulin secretion; for use in some embodiments for regenerating viability and/or cell proliferation of transplanted islets; for use in some embodiments for preventing and/or inhibiting rejection of a transplanted islets; for use in some embodiments for islet transplantation; for use in some embodiments for treating a symptom of a condition, disorder, or disease associated with abnormal insulin responsiveness to glucose in subjects.

Additionally, the compositions of the presently disclosed subject matter can also be used in some embodiments for preparation of medicaments. By way of example and not limitation, the compositions of the presently disclosed subject matter can be used for preparation of a medicament in some embodiments for regenerating pancreatic islet viability and/or cell proliferation in vitro, ex vivo, and/or in vivo; in some embodiments for regenerating glucose-stimulated insulin secretion; in some embodiments for regenerating viability and/or cell proliferation of a transplanted pancreatic islets; in some embodiments for preventing and/or inhibiting rejection of a transplanted islets; in some embodiments for pancreatic islet transplantation; and/or in some embodiments for treating a symptom of a condition, disorder, or disease associated with abnormal insulin responsiveness to glucose in a subject.

In any of the above referenced embodiments, the compositions of the presently disclosed subject matter comprise, consist essentially of, or consist of a peptide and/or a pharmaceutically acceptable salt thereof, and/or a biologically active fragment, analog, or derivative thereof, wherein the peptide, the pharmaceutically acceptable salt thereof, and/or the biologically active fragment, analog, or derivative thereof comprises, consists essentially of, or consists of an amino acid sequence comprising, consisting essentially of, or consisting of any of SEQ ID NOs: 1-60, or any combination thereof. In some embodiments, the composition is formulated for administration to a subject, optionally a human subject, by intravenous, intramuscular, oral, intranasal, and/or transdermal delivery.

In some embodiments, the composition is formulated as nanoparticle, a nanovesicle, a microparticle, a microvesicle, a liposome, packaged in PEG, lyophilized in pill form, or any combination thereof.

In some embodiments, the peptide, the pharmaceutically acceptable salt thereof, and/or the biologically active fragment, analog, or derivative thereof is comprises at least one modification selected from the group consisting of N- and/or C-terminal amidation, N- and/or C-terminal acylation, N- and/or C-terminal acetylation, addition of an N- and/or a C-terminal cysteine, pegylation, and combinations thereof. In some embodiments, the pegylation comprises addition of a PEG group to an N-terminal cysteine, a C-terminal cysteine, or both.

Methods for pegylating peptides and proteins are known in the art, and include pegylation at a reactive cysteines (see e.g., U.S. Pat. Nos. 8,329,866 and 9,050,371; each of which is incorporated by reference herein in its entirety). With respect to the PEGylated compounds of the presently disclosed subject matter, the PEG covalently attached to a peptide, a pharmaceutically acceptable salt thereof, and/or a biologically active fragment, analog, or derivative thereof has a molecular weight in the range from in some embodiments about 1 kDa to about 40 kDa, in some embodiments about 10 kDa to about 40 kDa, and in some embodiments about 40 kDa.

In some embodiments, the N-terminal amidation, the C-terminal amidation, or both comprises a modification with a substituted amide. In some embodiments, the N-terminal acylation, the C-terminal acylation, or both comprises a substituted acyl group.

In some embodiments, the composition is free of any type of enzymatic, chemical, or biochemical molecule capable of breakdown of the peptide at its termini that is sequential degradation of the peptide, the pharmaceutically acceptable salt thereof, and/or the biologically active fragment, analog, or derivative thereof at a terminal end thereof in the absence of the N- and/or C-terminal amidation, the N- and/or C-terminal acylation, the N- and/or C-terminal acetylation, or the combination thereof.

III. Exemplary Methods and Uses of the Presently Disclosed Subject Matter

The presently disclosed subject matter also relates in some embodiments to using the presently disclosed compositions in various treatment and/or therapeutic methods.

In some embodiments, the presently disclosed subject matter relates to methods for regenerating glucose-stimulated insulin secretion by contacting pancreatic islet cells in vitro, ex vivo, and/or in vivo with an effective amount of a composition comprising a peptide and/or a pharmaceutically acceptable salt thereof, and/or a biologically active fragment, analog, or derivative thereof, wherein the peptide, the pharmaceutically acceptable salt thereof, and/or the biologically active fragment, analog, or derivative thereof comprises, consists essentially of, or consists of an amino acid sequence comprising, consisting essentially of, or consisting of any of SEQ ID NOs: 1-60, or any combination thereof. As used herein, the phrase "regenerating glucose-stimulated insulin secretion" refers to inducing pancreatic islet cells that have ceased normal secretion of insulin in response glucose levels to re-initiate responding to environmental glucose levels by secreting insulin. Thus, in some embodiments the term "regenerate" and grammatical variants thereof refer to inducing non-responsive pancreatic islet cells to respond to environmental glucose levels that they would not or did not previously secret insulin in response to as a result of being contacted by a peptide and/or a pharmaceutically acceptable salt thereof, and/or a biologically active fragment, analog, or derivative thereof of the presently disclosed subject matter. In some embodiments, the contacting occurs in vitro, in some embodiments the contacting occurs ex vivo, in some embodiments the contacting occurs in vivo, and in some embodiments the contacting occurs on multiple occasions in vitro, ex vivo, and/or in vivo.

In some embodiments, the presently disclosed subject matter also relates to methods for regenerating viability and/or cell proliferation of transplanted and/or endogenous pancreatic islets by contacting pancreatic islets prior to, concurrently with, and/or subsequent to transplantation or without transplantation in diabetics, with an effective amount of a composition comprising a peptide and/or a pharmaceutically acceptable salt thereof, and/or a biologically active fragment, analog, or derivative thereof, wherein the peptide, the pharmaceutically acceptable salt thereof, and/or the biologically active fragment, analog, or derivative thereof comprises, consists essentially of, or consists of an amino acid sequence comprising, consisting essentially of, or consisting of any of SEQ ID NOs: 1-60, or any combination thereof, wherein the viability and/or proliferation of transplanted pancreatic islets, or endogenous islets, is regenerated relative to that of an islet cell that had not been contacted with the effective amount of the composition. As used herein, the phrase "regenerating viability and/or cell proliferation of transplanted and/or endogenous pancreatic islets" refers to any manipulation that occurs in vitro, ex vivo, or in vivo in which as a result of being contacted with a composition comprising a peptide and/or a pharmaceutically acceptable salt thereof, and/or a biologically active fragment, analog, or derivative thereof of the presently disclosed subject matter, a pancreatic islet's viability and/or proliferation is increased relative to that of the same pancreatic islet cell had it not been contacted with the peptide and/or a pharmaceutically acceptable salt thereof, and/or a biologically active fragment, analog, or derivative thereof of the presently disclosed subject matter.

In some embodiments, the presently disclosed subject matter relates to methods for preventing and/or inhibiting rejection of a transplanted pancreatic islets, or preventing further degeneration of endogenous pancreatic islets by contacting isolated pancreatic islets prior to, concurrently with, and/or subsequent to transplantation, and/or contacting endogenous diabetic islets, with an effective amount of a composition comprising a peptide and/or a pharmaceutically acceptable salt thereof, and/or a biologically active fragment, analog, or derivative thereof, wherein the peptide, the pharmaceutically acceptable salt thereof, and/or the biologically active fragment, analog, or derivative thereof comprises, consists essentially of, or consists of an amino acid sequence comprising, consisting essentially of, or consisting of any of SEQ ID NOs: 1-60, or any combination thereof, wherein rejection of the transplanted islet cell is prevented and/or inhibited relative to that of an islet cell that had not been contacted with the effective amount of the composition.

In some embodiments, the presently disclosed subject matter relates to methods for pancreatic islet transplantation by transplanting pancreatic islets into a transplant recipient, wherein islets have been contacted prior to, concurrently with, and/or subsequent to the transplanting step with an effective amount of a composition comprising a peptide and/or a pharmaceutically acceptable salt thereof, and/or a biologically active fragment, analog, or derivative thereof, wherein the peptide, the pharmaceutically acceptable salt thereof, and/or the biologically active fragment, analog, or derivative thereof comprises, consists essentially of, or consists of an amino acid sequence comprising, consisting essentially of, or consisting of any of SEQ ID NOs: 1-60, or any combination thereof, wherein rejection of the transplanted pancreatic islet cell is prevented and/or inhibited relative to that of an pancreatic islet cell that had not been contacted with the effective amount of the composition.

In some embodiments, the presently disclosed subject matter relates to methods for restoring health to nerves supplying pancreatic islets. As used herein, the phrase "restoring health to nerves supplying pancreatic islets" refers to enhancing any biological activity of a nerve innervating a pancreatic islet, which in some embodiments can be a biological activity that is abnormal as compared to a biological activity of a nerve supplying pancreatic islets in a healthy subject. Thus, in some embodiments "restoring health to nerves supplying pancreatic islets" refers to enhancing a biological activity of a nerve supplying pancreatic islets to about what it would be in a healthy subject In some embodiments, the methods comprise contacting nerves of pancreatic islets in vitro, ex vivo, and/or in vivo with an effective amount of a composition comprising a peptide and/or a pharmaceutically acceptable salt thereof, and/or a biologically active fragment, analog, or derivative thereof, wherein the peptide, the pharmaceutically acceptable salt thereof, and/or the biologically active fragment, analog, or derivative thereof comprises, consists essentially of, or consists of an amino acid sequence comprising, consisting essentially of, or consisting of any of SEQ ID NOs: 1-60, or any combination thereof.

In some embodiments, the presently disclosed subject matter relates to methods for treating a symptom of a condition, disorder, or disease associated with abnormal insulin responsiveness to glucose in a subject, optionally wherein the condition, disorder, or disease is type 1 or 2 diabetes by administering to the subject an effective amount of a composition comprising a peptide and/or a pharmaceutically acceptable salt thereof, and/or a biologically active fragment, analog, or derivative thereof, wherein the peptide, the pharmaceutically acceptable salt thereof, and/or the biologically active fragment, analog, or derivative thereof comprises, consists essentially of, or consists of an amino acid sequence comprising, consisting essentially of, or consisting of any of SEQ ID NOs: 1-60, or any combination thereof, wherein rejection of the transplanted pancreatic islets is prevented and/or inhibited relative to that of an islets that had not been contacted with the effective amount of the composition. As used herein, the phrase "a condition, disorder, or disease associated with abnormal insulin responsiveness to glucose" refers to any a condition, disorder, or disease at least one symptom and/or consequence of which results from aberrant responsiveness of a cell, tissue, or organ to the local glucose concentration. In some embodiments, the cell is a pancreatic islet cell and the aberrant responsiveness comprises an inability to secrete insulin in response to glucose. A particular exemplary condition, disorder, or disease associated with abnormal insulin responsiveness to glucose is diabetes, including but type 1 and type 2 diabetes.

In some embodiments, the subject to whom the presently disclosed methods are applicable is thus a subject with a condition, disorder, or disease associated with abnormal insulin responsiveness to glucose, who in some embodiments is a subject with type 1 or type 2 diabetes. In some embodiments, such a subject can be treated with a composition of the presently disclosed subject matter in combination with one or more additional anti-diabetes therapies. As used herein, the phrase "anti-diabetes therapy" refers to any medically accepted intervention designed to ameliorate at least one symptom or consequence of diabetes. Exemplary such anti-diabetes therapies include, but are not limited to immune therapies such as but not limited to administering IgM (see U.S. Patent Application Publication No. 2015/0265704); administration of one or more calcineurin inhibitors such as but not limited to Tacrolimus (IUPAC name (1R,9S,12S,13R,14S,17R,18E,21S,23S,24R,25S,27R)-1,14-dihydroxy-12-[(1E)-1-[(1R,3R,4R)-4-hydroxy-3-methoxycyclohexyl]prop-1-en-2-yl]-23,25-dimethoxy-13,19,21,27-tetramethyl-17-(prop-2-en-1-yl)-11,28-dioxa-4-azatricyclo[22.3.1.0$^{4,9}$]octacos-18-ene-2,3,10,16-tetrone; see e.g., U.S. Pat. Nos. 6,884,433; 8,623,410; 8,911,777; and 9,011,922); administration of a glucagon-like peptide-1 (GLP-1) analog such as but not limited to exendin-4 (amino acid sequence HGEGTFTSDLSKQMEEEAVRLFIEWLKNGGPSSGAPPPS; SEQ ID NO: 63; see e.g., U.S. Pat. Nos. 6,902,744; 8,057,822; and 9,133,260); or any combination thereof. Each of these U.S. patent application publications and patents is incorporated by reference in its entirety.

In some embodiments of the presently disclosed methods, the composition employed is formulated for use in a human and/or wherein the pancreatic islet cell is a human islet cell, and/or wherein the pancreatic islet cell is present within a subject, which in some embodiments is a human subject. In some embodiments of the presently disclosed methods, the composition comprises, consists essentially of, or consists of a sequence selected from the group consisting of SEQ ID NO: 62, or a sequence that differs from SEQ ID NO: 62 by 1, 2, 3, 4 or 5 amino acid modifications

EXAMPLES

The presently disclosed subject matter will be now be described more fully hereinafter with reference to the accompanying EXAMPLES, in which representative embodiments of the presently disclosed subject matter are shown. The presently disclosed subject matter can, however, be embodied in different forms and should not be construed as limited to the embodiments set forth herein. Rather, these embodiments are provided so that this disclosure will be thorough and complete, and will fully convey the scope of the presently disclosed subject matter to those skilled in the art.

Example 1

Figure 3:
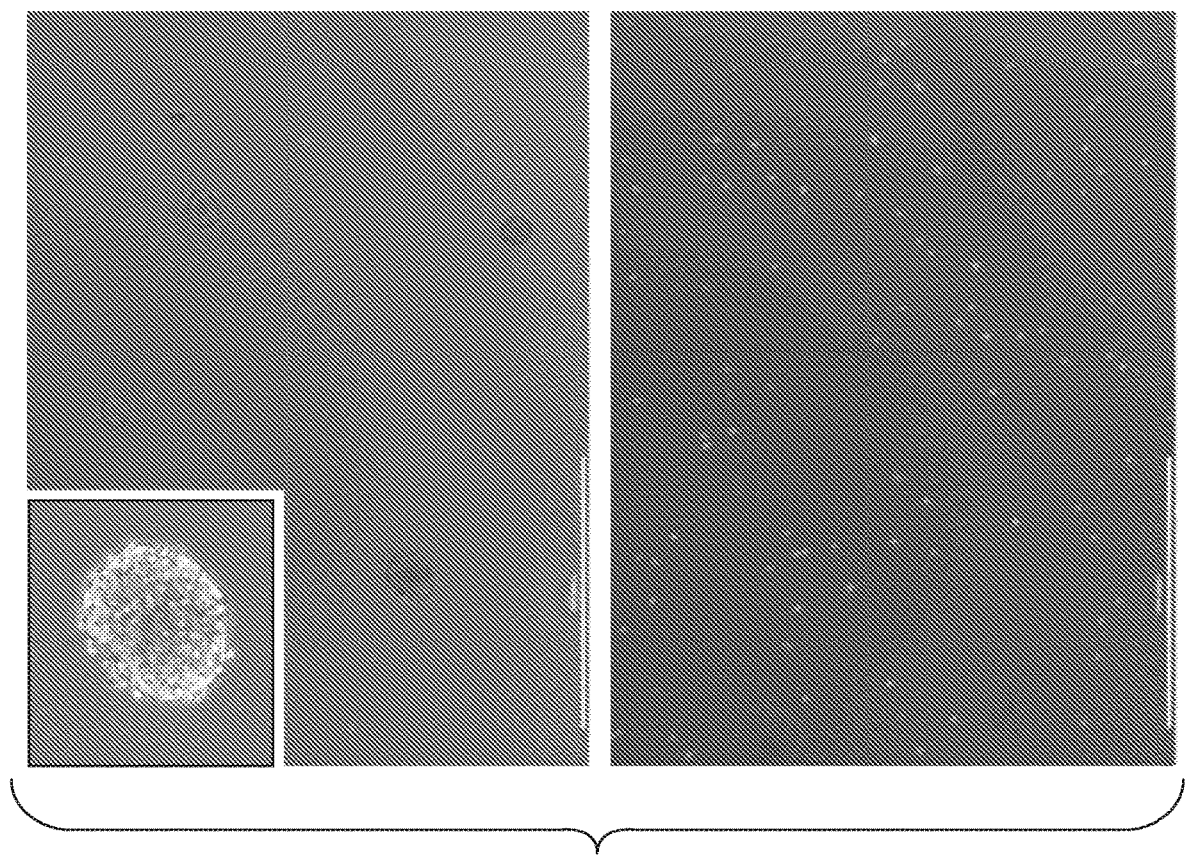
FIG. 3 is a micrograph of isolated mouse pancreatic islets. The inset provides a higher magnification.

C57BL/6 islets (see FIG. 3) were cultured with 4 µM N-94 (N-94) peptide or control peptide C-95 for different time periods ranging from 1-15 days in DMEM at 37° C. Viability of islets was scored by propidium iodide-fluorescein diacetate staining. The results are presented in FIG. 1A.

Figure 1B:
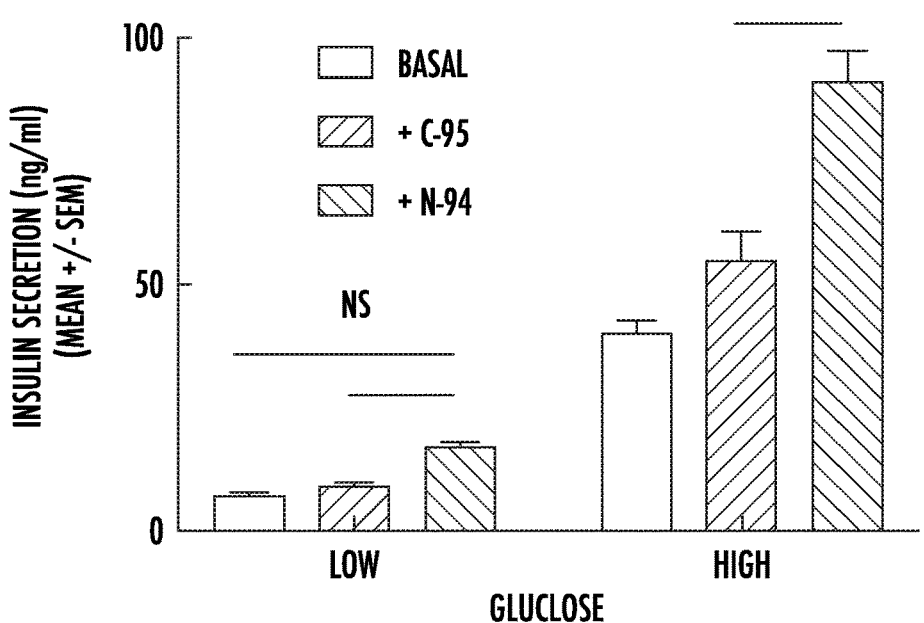

C57BL/6 islets were also incubated overnight with 4 µM N-94 peptide (SEQ ID NO: 1) or C-95 peptide or no additive following which Glucose-stimulated Insulin secretion (GSIS) assays were performed. The results are presented in FIG. 1B.

Human islet cells were similarly incubated with a N-94 peptide or C-95 peptide for varying periods of time following which GSIS assay and viability measurements were conducted. Insulin was measured using Insulin ELISA kit (Mercodia, Uppsala, Sweden).

Figure 2A:
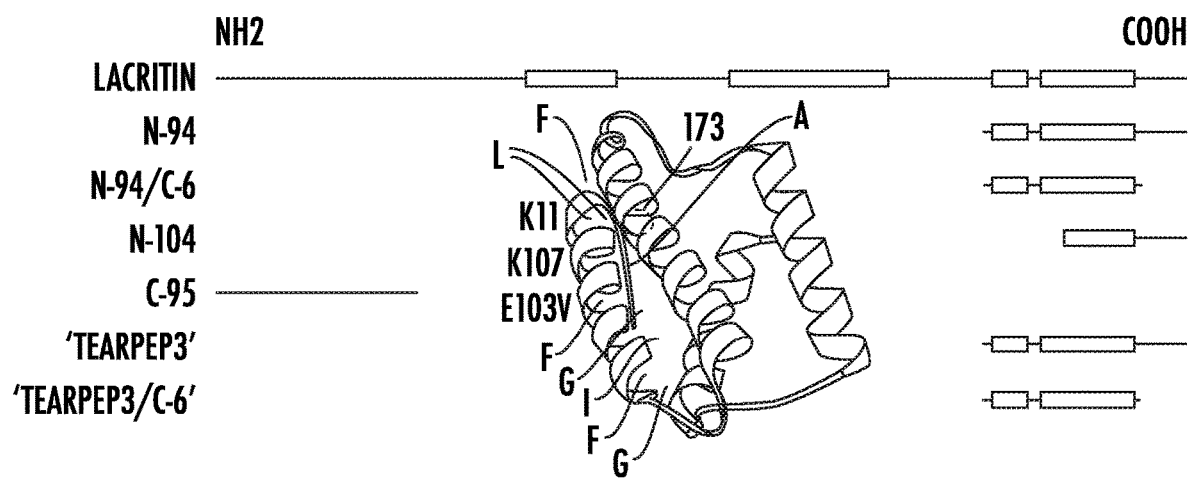
FIG. 2A depicts the structures of certain exemplary embodiments of the peptides of the presently disclosed subject matter, including lacritin (SEQ ID NO: 61) and several derivatives. See Table 2 for the sequences of these peptides.
Figure 2B:
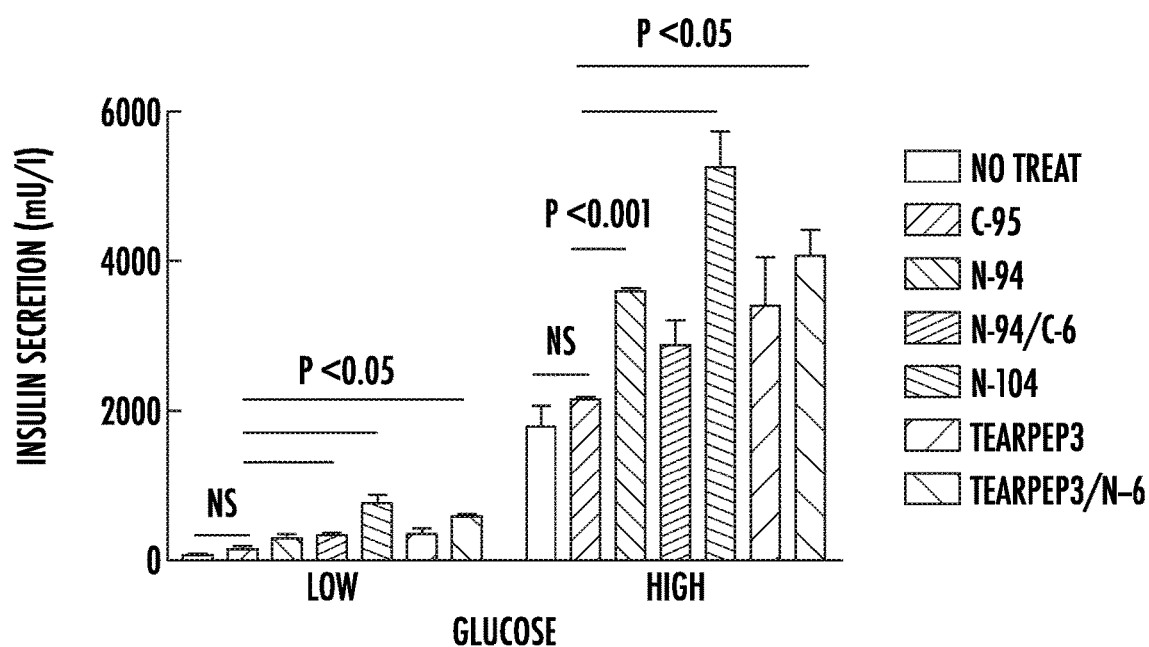
FIG. 2B is a bar graph showing the results of glucose-dependent insulin secretion assay 24 hours after treatment with 1 μM of the listed exemplary peptides. 100 human islets each were left untreated (white, leftmost bars), or were treated overnight with 1 μM C-95 peptide (second bars from the left), N-94 peptide (third bars from the left), N-94/C-6 peptide (SEQ ID NO: 62; fourth bars from the left), N-104 peptide (SEQ ID NO: 49; fifth bars from the left)), Tearpep3 peptide (SEQ ID NO: 21; second bars from the right), or Tearpep3/C-6 peptide (SEQ ID NO: 33; black, rightmost bars) for 24 hours, after which glucose-dependent insulin secretion was determined. Most active was N-104 followed by Tearpep3/C-6. NS: not significant.

Human islet cells were incubated overnight with 1 µM N-94 peptide (SEQ ID NO: 1), N-94/C6 peptide (SEQ ID NO: 62), N104 peptide, Tearpep3 peptide (SEQ ID NO: 21), Tearpep3/C6 peptide (SEQ ID NO: 33), C-95 peptide, or no treatment followed by GSIS assays (se FIG. 2A for the structures of, and Table 2 for the sequences of, these exemplary peptides). C57BL/6 islet cells were pretreated with 4 µM N-94 N-94 peptide or C-95 peptide or saline for 24 hours followed by minimal islet mass transplantation into syngeneic diabetic recipients. Tail vein blood glucoses were measured daily. The results are presented in FIG. 2B.

Islet cells cultured with N-94 peptide retained 61% viability at Day 15 compared to islet cells cultured with control peptide C-95 that demonstrated only 20% viability (p<0.001). N-94 peptide increased GSIS by nearly 2-fold (91±22 mg/L) compared to untreated (39.86±7.81 mg/L) or C-95 peptide-treated islet cells (54.9±18.14 mg/L). Viability of human islets that were incubated with N-94 peptide was 84% at Day 6 compared to 66% observed with C-95 peptide, and 58% with saline. However, maximal GSIS activity of human islets with N-94 peptide was only observed until Day 3.

Following incubation with different N-94 peptide analogs, comparison of their GSIS response indicated a near doubling with N-94 peptide when compared to C-95 peptide, while that of N104 peptide was nearly 3.5-fold more; and that of Tearpep3 peptide and Tearpep3/C6 peptide was >2.5-fold. Incubation of islets with N-94 peptide permanently returned transplanted mice to normoglycemia with glucoses below 200 mg/dL within 9 days posttransplant with treatment efficacy continuing after 40 days posttransplant. With C-95 peptide treatment, the glucose at Day 12 posttransplant was <250 mg/dL. Average blood glucoses measured between Days 22 to 43 was 142.9±17.6 mg/dL for N-94 peptide group compared to 275±34.8 mg/dL for the C-95 peptide group.

Example 2

35 C57BL/6 islets/per well were cultured with 4 µM of N-94 peptide analog N-94 or control C-95 peptide for 1, 2, 5, 7,10 or 15 days in DMEM at 37° C. Viability of islets was scored after staining with PI/FDA. Islets cultured with N-94 peptide retained 95±3, 89±15, 80±17.5 and 61±21% viability while islets cultured with C-95 peptide retained 95±3, 87±13, 40±28 and 20±19% viability at Day 1, 5, 10 and 15.

C57BL/6 islets were incubated overnight with 4 µM N-94 peptide or C-95 peptide or no additive. 50 islets/well were used to perform Glucose stimulated Insulin secretion (GSIS) assay. Islets that were untreated or treated with C-95 peptide or with N-94 peptide and stimulated with high glucose (28 mM) secreted 39.86±7.81, 54.9±18.14, and 91±22.16 ng/ml Insulin. N-94 peptide increased insulin secretion by 2-fold compared to untreated control. Viability of human islets incubated with N-94 peptide at Day 1, 3, 4, 6, and 9 was 95±4, 95±3, 94±4, 84±9, and 80±15% while with C-95 it was 94±4, 91±7, 88±8, 66±16, and 65±18%. With saline it was 94±4, 94±3, 88±8, 58±19, and ~53. While GSIS results were similar to the mouse results, maximum insulin secretion activity with N-94 peptide was only observed on Day 1 and 3.

50 human islets were incubated with N-94 peptide or C-95 peptide for 1, 3, 4, 6 and 9 days following which GSIS assay and viability measurement were conducted. Insulin was measured using Insulin ELISA kit (Mercodia). When comparing insulin secretion in response to 28 mM glucose, insulin secretion for N-94 peptide was nearly doubled compared to C-95 peptide, that of N104 peptide was nearly 3.5-fold more and that of Tearpep3 peptide and Tearpep3/C6 peptide >2.5-fold.

Human islets were incubated overnight with 1 µM N-94 peptide, N-94/C6 peptide, N104 peptide, Tearpep3 peptide, Tearpep3/C6 peptide, C-95 peptide, or no treatment and GSIS assay performed.

75 C57Bl/6 islets were transplanted into C57BL/6 recipients made diabetic by single STZ injection (220 mg/Kg). Islets were pretreated with 4 µM N-94 peptide or C-95 peptide or saline for 24 hours prior to transplantation into diabetic mice (n=2 mice/group). Tail vein blood glucoses were measured daily. Incubation of islets with N-94 peptide permanently returned transplanted mice to normoglycemia with glucoses below 200 mg/dL within 9 days posttransplant. With C-95 peptide treatment, the glucose at Day 12 posttransplant was <250 mg/dL. Mice transplanted with untreated islets remained diabetic.

Example 3

Figure 4:
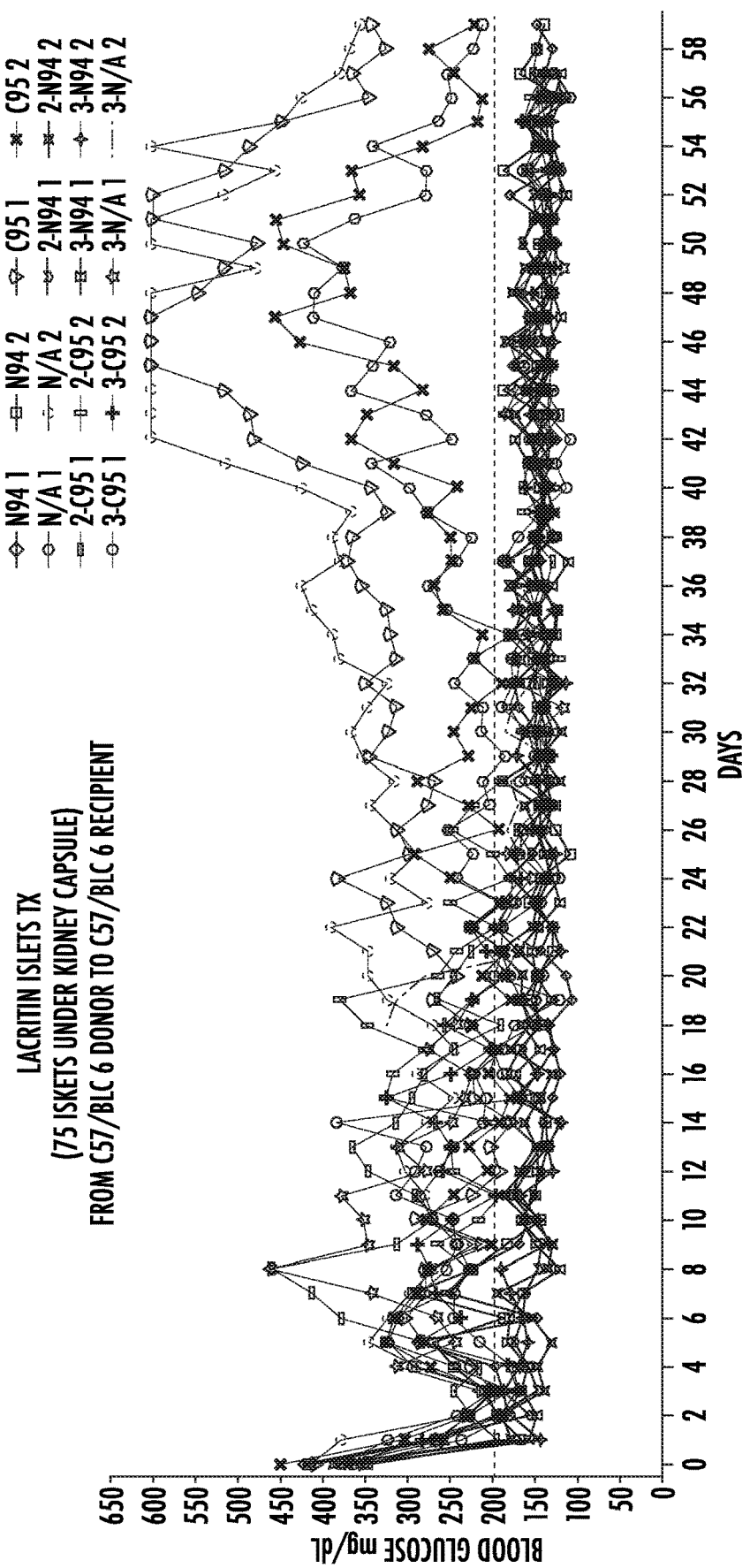
FIG. 4 is a graph of blood glucose levels of pancreatic islets treated with the indicated peptides and transplanted into diabetic mice observed for 60 days. Shown is a graph of blood glucose levels after minimal transplantation of 75 N-94 peptide-treated, C-95 peptide-treated, or saline-treated C57Bl/6 islets under the kidney capsule of C57BL/6 mice made diabetic before transplantation by single streptozotocin injection (220 mg/kg; two mice per group). Pretreatment was for 24 hours. Tail vein blood was collected daily for glucose analyses. Each line represents the progressive blood glucose level of a single diabetic mouse. Six mice each received N-94 peptide treated islets (black), six others received C-95 peptide treated islets (blue), and four received saline treated islets (orange). N-94 peptide permanently returned transplanted mice to normoglycemia with glucose below 200 mg/dL within 9 days post-transplantation with treatment efficacy continuing after 40 days post-transplantation. With C-95 peptide treatment, the glucose at Day 12 post-transplant was <250 mg/dL. Average blood glucoses measured between Days 22 to 43 were 142.9±17.6 mg/dL for the N-94 group compared to 275±34.8 mg/dL for the C-95 peptide group. The Figure shows that N-94 peptide pretreated pancreatic islets transplanted into diabetic mice rapidly restores normoglycemia.

FIG. 4 is a graph of blood glucose levels of pancreatic islets treated with the indicated peptides and transplanted into diabetic mice observed for 60 days. Shown is a graph of blood glucose levels after minimal transplantation of 75 N-94 peptide-treated, C-95 peptide-treated, or saline-treated C57Bl/6 islets under the kidney capsule of C57BL/6 mice made diabetic before transplantation by single streptozotocin injection (220 mg/kg; two mice per group). Pretreatment was for 24 hours. Tail vein blood was collected daily for glucose analyses. Each line represents the progressive blood glucose level of a single diabetic mouse. Six mice each received N-94 peptide treated islets (black), six others received C-95 peptide treated islets (blue), and four received saline treated islets (orange). N-94 peptide permanently returned transplanted mice to normoglycemia with glucose below 200 mg/dL within 9 days post-transplantation with treatment efficacy continuing after 40 days post-transplantation. With C-95 peptide treatment, the glucose at Day 12 post-transplant was <250 mg/dL. Average blood glucoses measured between Days 22 to 43 were 142.9±17.6 mg/dL for the N-94 group compared to 275±34.8 mg/dL for the C-95 peptide group. The Figure shows that N-94 peptide pretreated pancreatic islets transplanted into diabetic mice rapidly restores normoglycemia.

Example 4

Figure 5:
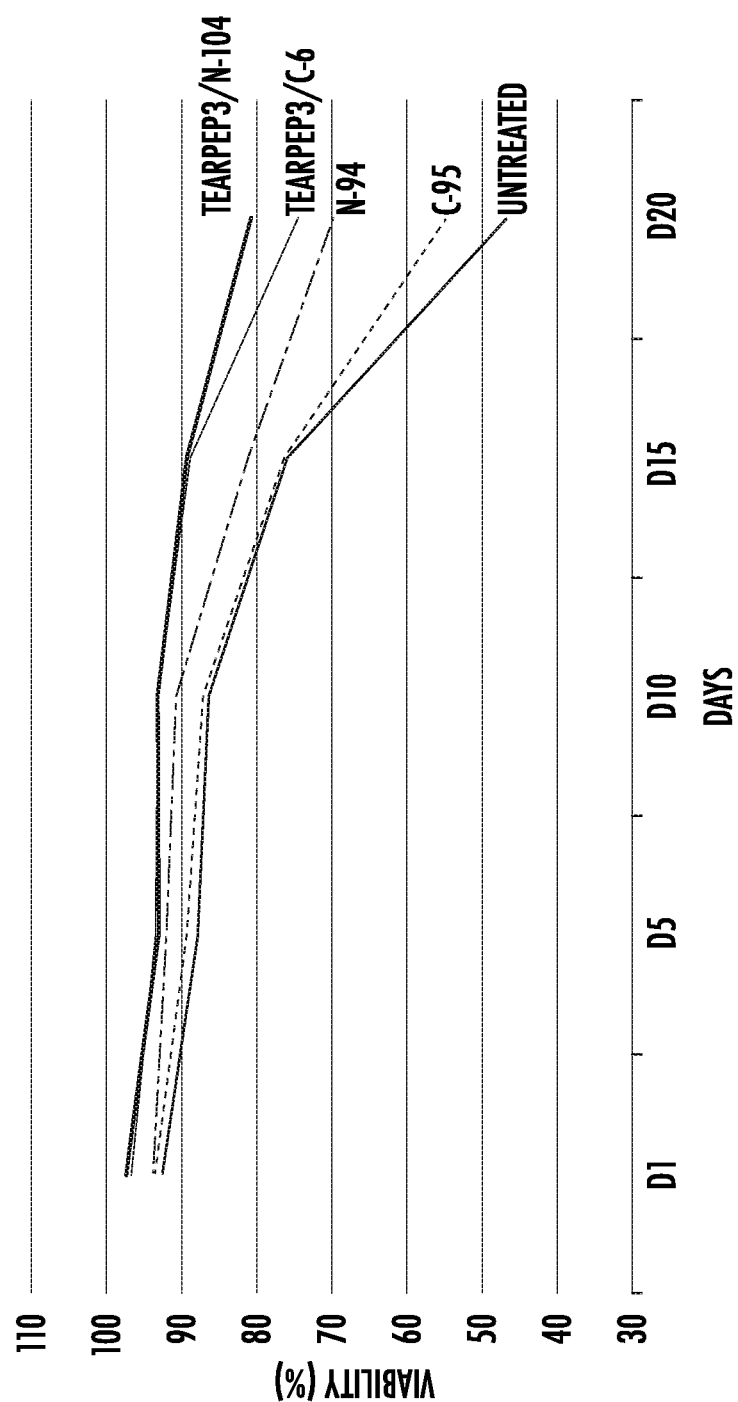
FIG. 5 is a plot of experiments showing that 4 μM Tearpep3/N-104 treated human islets displayed superior viability twenty days after isolation versus 4 μM Tearpep3/C-6 and lacritin N-94. Lacritin C-95 synthetic peptide (4 μM) derived from the inactive N-terminus of lacritin served as a negative control.

Human islets were treated with various peptides of the presently disclosed subject matter and viability was assessed at twenty days post-treatment. The results are presented in FIG. 5. 4 µM Tearpep3/N-104 peptide-treated human islets displayed superior viability twenty days after isolation versus 4 µM Tearpep3/C-6 peptide and lacritin N-94 peptide. Lacritin C-95 synthetic peptide (4 µM) derived from the inactive N-terminus of lacritin served as a negative control.

Example 5

Figure 6:
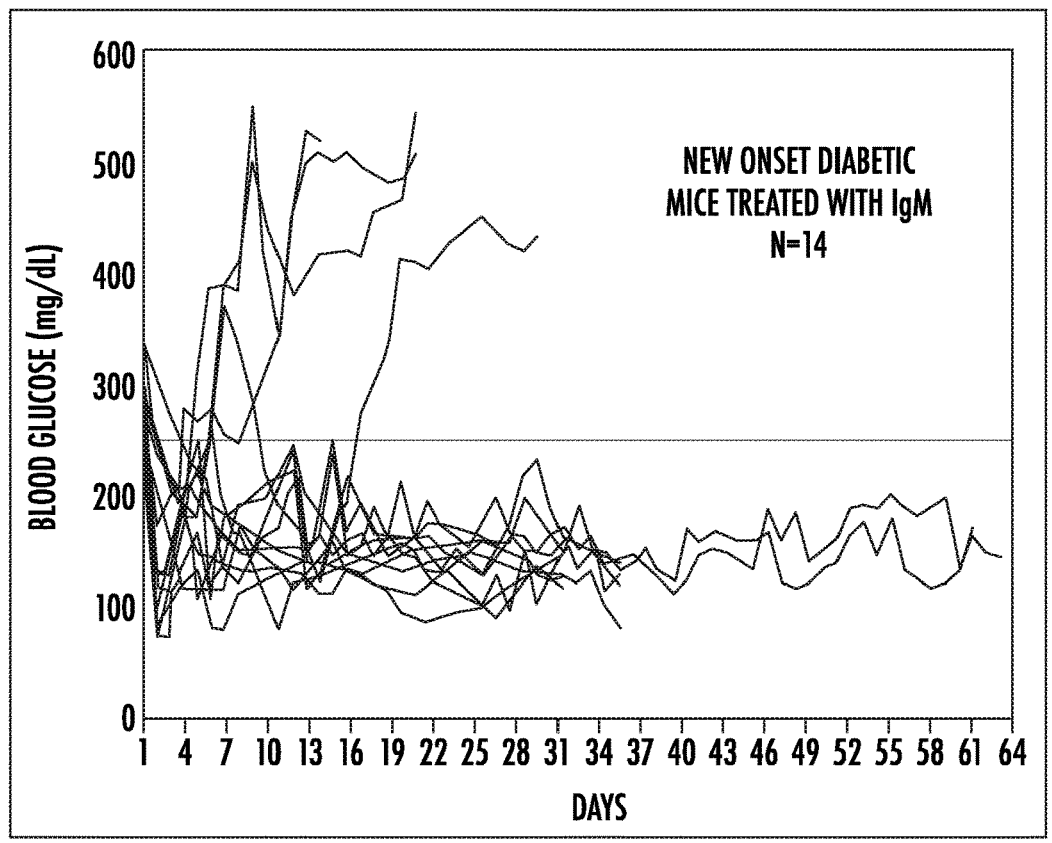
FIG. 6 is a graph of blood glucose levels of mice NOD mice treated with three doses of 200 μg each of IgM on Days 1, 3, and 5 beginning at the initial appearance of hyperglycemia (e.g., BG 180-340 mg/dL). Diabetes was reversed in 70% of NOD mice for the entire duration of the monitoring.

Blood glucose levels of mice NOD mice treated with three doses of 200 µg each of IgM on Days 1, 3, and 5 beginning at the initial appearance of hyperglycemia (e.g., BG 180-340 mg/dL) were tested. The results are presented in FIG. 6. Diabetes was reversed in 70% of NOD mice for the entire duration of the monitoring.

Example 6

Figure 7:
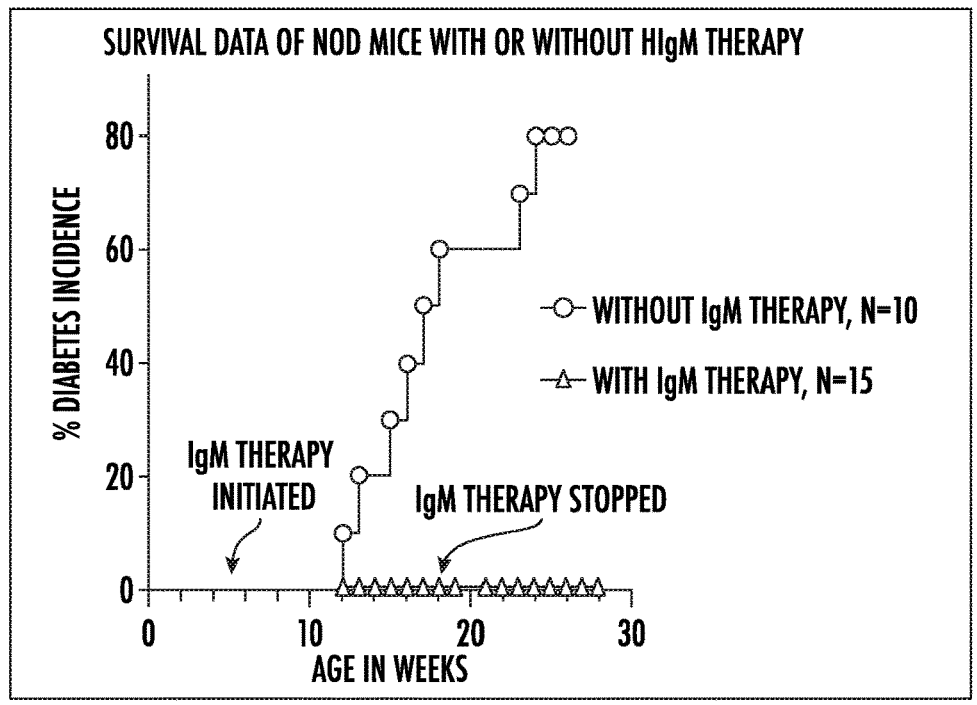
FIG. 7 is a plot showing that IgM therapy inhibits T1D onset. 80% NOD control mice receiving saline became diabetic by 18 to 20 weeks of age. Mice receiving IgM twice a week (~50 μg in 100 μl PBS) demonstrated significant protection from T1D when therapy was begun early (at 5 weeks of age) (p<0.0001). [BSA resulted in 70% T1D incidence whilst IgG administration resulted in 50% (n=10/group) disease incidence at 25 weeks of age]. Discontinuing therapy resulted in diabetes in only 9 of 33 mice at 22-weeks post-discontinuation, indicating the development of tolerance.

Blood glucose levels were tested in NOD mice treated with IgM. As shown in FIG. 7, IgM therapy inhibited T1D onset. 80% NOD control mice receiving saline became diabetic by 18 to 20 weeks of age. Mice receiving IgM twice a week (~50 µg in 100 µl PBS) demonstrated significant protection from T1D when therapy was begun early (at 5 weeks of age; p<0.0001). BSA resulted in 70% T1D incidence whilst IgG administration resulted in 50% (n=10/group) disease incidence at 25 weeks of age. Discontinuing therapy resulted in diabetes in only 9 of 33 mice at 22-weeks post-discontinuation, indicating the development of tolerance.

Figure 8:
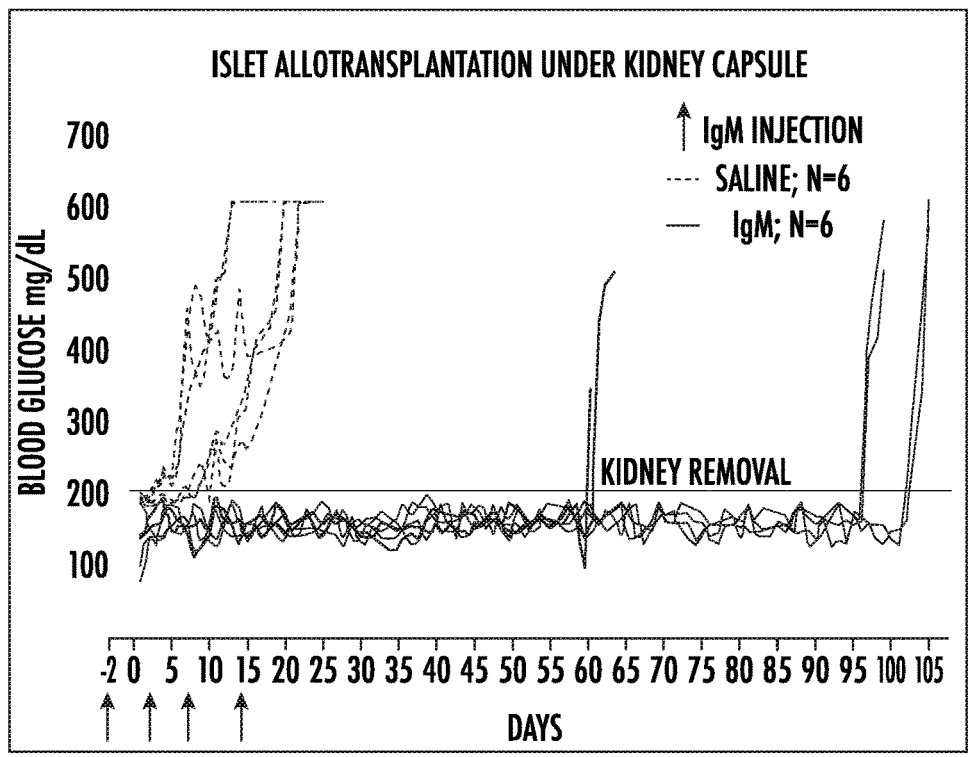
FIG. 8 is a graph showing that in the NOD mouse, IgM treatment reversed established disease in conjunction with islet transplantation.

IgM treatment was also tested with respect to whether it could reverse established disease in conjunction with islet transplantation. As shown in FIG. 8, IgM treatment in conjunction with islet transplantation reversed established disease.

Example 7

Whether the peptides of the presently disclosed subject matter could enhance viability of human sensory neurons stressed with inflammatory cytokines was tested. Sensory neurons were derived from Induced Pluripotent Stem Cells (iPSC). iPSCs were seeded into 12 well Matrigel-coated plates ($1.25\times10^5$ cells/well). Neural differentiation was initiated when cells were confluent using KSR medium. 100 nM of LDN-193189 and 10 mM of SB431542 were added to the culture from day 0 to 6, to inhibit SMAD signaling. On day 4, 25% of N2 medium was added to the culture, with 100% of N2 medium at day 10. Sensory neurons induction was initiated at day 2 (day 2-10), with the addition of 3 mM CHIR 99021, 10 mM SU5402, and 10 mM DAPT. From day 10 to day 21 neuron maturation was promoted with 25 ng/mL of β-NGF, BDNF, and GDNF. Cells were fed every day.

Figure 9A:
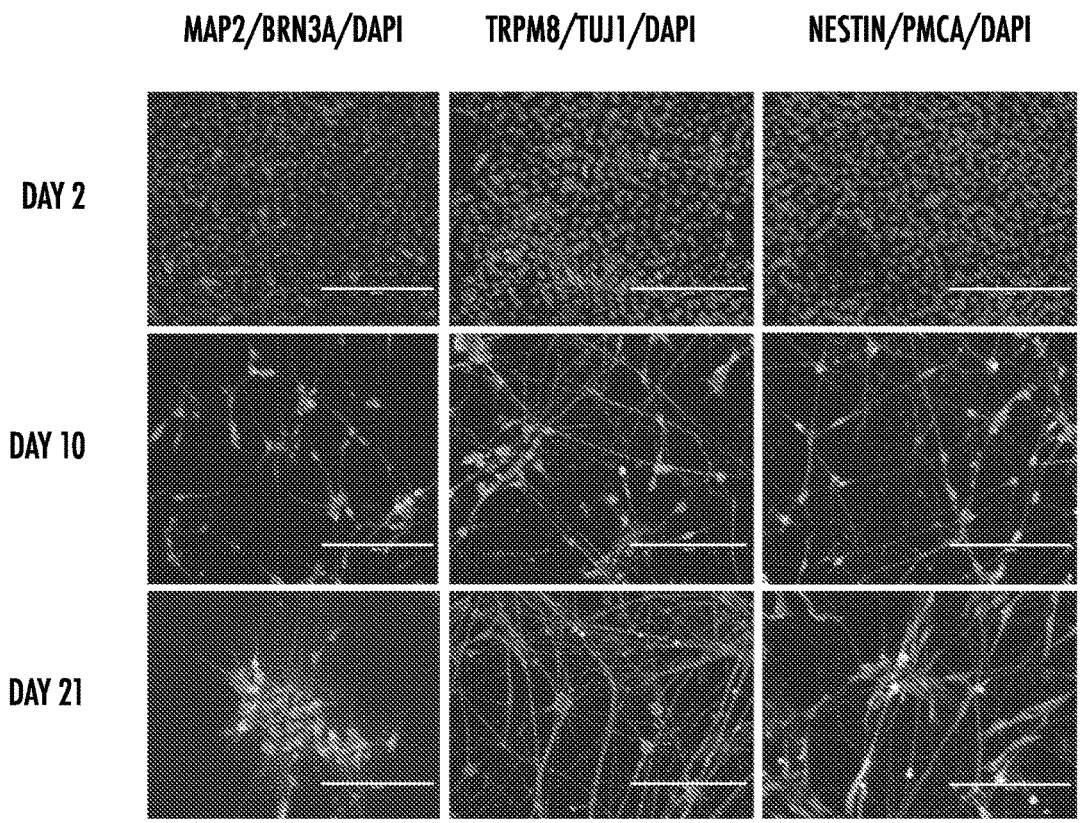
FIGS. 9A-9C depict the results of experiments showing that the N-94/C-6 peptide of the presently disclosed subject matter restored viability to human sensory neurons stressed with inflammatory cytokines.

To analyze markers for sensory neurons, immunofluorescence was performed on cells at day 0, day 10 and day 21. Cells were incubated overnight with primary antibodies for MAP2 (1:500, ABCAM), Brn3a (1:125, Merck), PMCA (1:500, ABCAM), Tuj1 (10 mg/mL, R&D Systems), Nestin (1:500, ABCAM), and TRPM8 (1:500, NovusBio). Secondary antibodies Alexa 568 (Thermo) and Alexa 488 (Thermo) were incubated for 2 hours at room temperature. DAPI (1:5000, Thermo) was incubated for 5 minutes at room temperature. Representative fluorescence micrographs are presented in FIG. 9A.

Figure 9B:
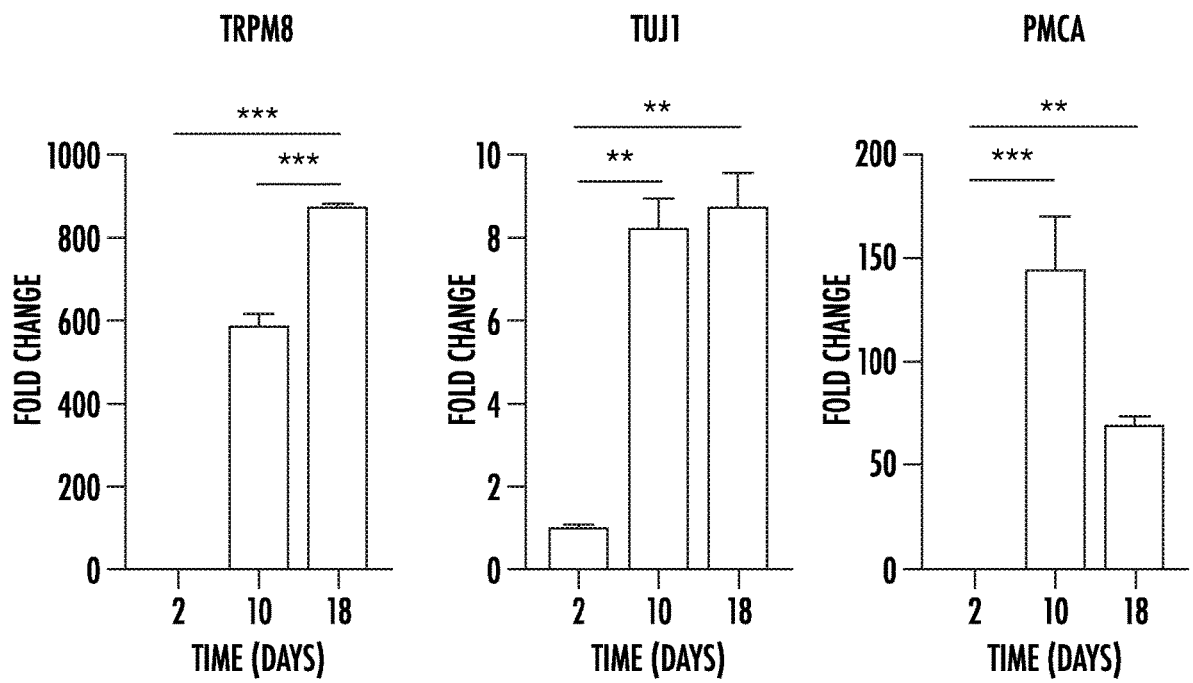

To analyze mRNA levels, total RNA was extracted on day 0, day 10 and day 18 and analyzed by qRT-PCR. The results are presented in FIG. 9B.

Figure 9C:
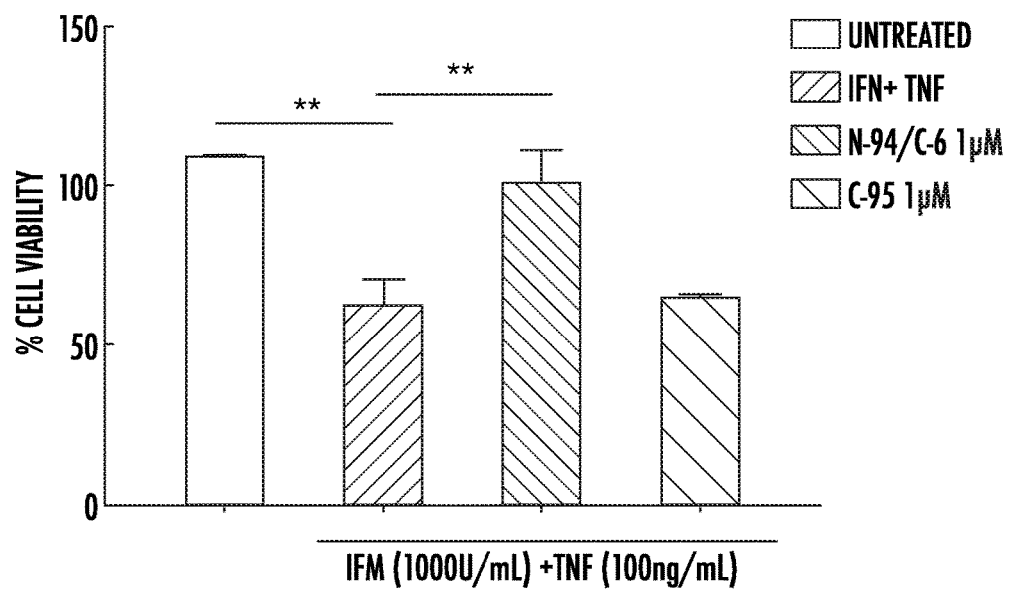

Sensory neurons (day 21) were incubated with IFN-g (1000 U/mL)+TNF-α (100 ng/mL) with or without 1 mM of the N-94/C-6 peptide or the negative control C-95 peptide for 72 hours in a 96-well plate. Alamar Blue reagent (10%) was added in each well. Fluorescence was measured after 6 hours (excitation at 545 nm/emission at 590 nm). The results are presented in FIG. 9C.

Discussion of the Examples

N-94 peptide and its analogs and derivatives promoted mouse and human islet viability, enhanced insulin secretion, and prevented islet graft rejection. Thus, the compositions disclosed herein have utility as interventional agents to promote islet survival such as but not limited to following transplantation as well as in the treatment of Type 1 diabetes. Interestingly, the peptides of the presently disclosed subject matter also restored viability to human neurons that were derived from induced pluripotent stem cells (IPSCs) that were stressed with interferon gamma and TNF. While not wishing to be bound by any particular theory of operation, the neuron benefit could be applicable to enhancement of viability of endogenous islets using the compositions and methods of the presently disclosed subject matter.

Type 1 diabetes (T1D) in particular remains a devastating, chronic autoimmune disease, the incidence of which continues to rise annually. Since T1D is rarely diagnosed before ~70-80% β-cell destruction has occurred, developing therapies that facilitate β-cell recovery following diagnosis of new onset diabetes remains an important goal. IgM therapy has been shown to play a key role in the maintenance of beta cell-specific tolerance and diabetes reversal, and that this effect is associated with its ability to eliminate both autoreactive B cells and inhibit insulin autoantibody production, attenuate inflammation, expand immunoregulatory regulatory T cells (Tregs), and increase islet cell. IgM administration, when initiated early, completely inhibits the onset of T1D (p<0.0001) in non-obese diabetic (NOD) mice. It reestablishes B cell homeostasis, regulates T cell activation, proliferation and chemotaxis, inhibits insulitis, promotes islet cell proliferation, and in conjunction with islet transplantation reverses diabetes in mice with established T1D. It has also been demonstrated that IgM administration alone reverses disease in ~70% of mice presenting with new-onset diabetes. It is possible that in the 30% of NOD mice that did progress to diabetes despite receiving IgM treatment, beta cell destruction was too far progressed at the time for intervention for IgM therapy to be effective and/or immunesuppression with IgM alone was not enough to reverse autoimmunity.

Thus, in some embodiments combining IgM treatment with another short term immunosuppressant and/or with an agent that promoted endogenous beta-cell regeneration was investigated herein.

REFERENCES

All references listed below, as well as all references cited in the instant disclosure, including but not limited to all patents, patent applications and publications thereof, scientific journal articles, and database entries (e.g., GENBANK® and UniProt biosequence database entries and all annotations available therein) are incorporated herein by reference in their entireties to the extent that they supplement, explain, provide a background for, or teach methodology, techniques, and/or compositions employed herein.

Altschul et al. (1993) Basic local alignment search tool. J Mol Biol. 215:403-410.

Bird et al. (1988) Single-chain antigen-binding proteins. Science. 242(4877):423-426.

Huston et al. (1993) Medical applications of single-chain antibodies. Int Rev Immunol. 10(2-3):195-217.

Karnati et al. (2013) Lacritin and the tear proteome as natural replacement therapy for dry eye. Exp Eye Res. 117:39-52.

Merrifield (1963) Solid phase peptide synthesis. I. The synthesis of a tetrapeptide. J Am Chem Soc. 85:2149-2154.

PCT International Patent Application Publication No. WO 2019/143767.

Riahi et al. (2018) Inhibition of mTORC1 by ER stress impairs neonatal β-cell expansion and predisposes to diabetes in the Akita mouse. eLife 2018; 7:e38472.

Stewart et al. (1984) *Solid Phase Peptide Synthesis*, $2^{nd}$ ed., Pierce Chemical Co., Rockford, Illinois, United States of America, pp. 11-12.

Tatum et al. (2017) Single-donor islet transplantation in type 1 diabetes: patient selection and special considerations. Diabetes Metab Syndr Obes. 10:73-78.

U.S. Patent Application Publication Nos. 2003/0017534, 2004/0086508, 2009/0191608, 2018/0298087, 2018/0312588, 2018/0346564, 2019/0381136, 2019/0151448.

U.S. Pat. Nos. 4,816,567; 5,482,856; 6,479,284; 6,677,436; 7,060,808; 7,304,033; 7,906,625; 8,398,980; 8,436,150; 8,796,439; 10,253,111; 10,393,755.

Wang et al. (2006) Restricted epithelial proliferation by lacritin via PKCalpha-dependent NFAT and mTOR pathways. J Cell Biol. 174(5):689-700.

Wang et al. (2013) Lacritin rescues stressed epithelia via rapid forkhead box 03 (FOXO3)-associated autophagy that restores metabolism. J. Biol Chem. 288(25):18146-18161.

Wang et al. (2015a) A high-throughput chemical screen reveals that harmine-mediated inhibition of DYRK1A increases human pancreatic beta cell replication. Nat Med. 21(4):383-388.

Xu et al. (2018) Inhibition of TBK1/IKKε Promotes Regeneration of Pancreatic β-cells. Sci Rep. 22; 8(1):15587.

Zhang et al. (2013) Targeting of heparanase-modified syndecan-1 by prosecretory mitogen lacritin requires conserved core GAGAL plus heparan and chondroitin sulfate as a novel hybrid binding site that enhances selectivity. J Biol Chem. 288:12090-12101.

While the presently disclosed subject matter has been disclosed with reference to specific embodiments, it is apparent that other embodiments and variations of the presently disclosed subject matter may be devised by others skilled in the art without departing from the true spirit and scope of the presently disclosed subject matter.

What is claimed is:

1. A method for regenerating glucose-stimulated insulin secretion, the method comprising contacting pancreatic islets in vitro, ex vivo, and/or in vivo with an effective amount of a peptide, or a pharmaceutically acceptable salt thereof, wherein the peptide or the pharmaceutically acceptable salt thereof comprises an amino acid sequence comprising any of SEQ ID NOs: 21-44, or any of SEQ ID NOs: 45-48 with a Q to N substitution.

2. The method of claim 1, wherein the peptide, or the pharmaceutically acceptable salt thereof is in a composition, wherein the composition is formulated for administration to a subject, and wherein the method comprises administering the composition to the subject.

3. The method of claim 1, wherein the peptide, or the pharmaceutically acceptable salt thereof, is formulated as a nanoparticle, a nanovesicle, a microparticle, a microvesicle, a liposome, or any combination thereof.

4. The method of claim 1, wherein the peptide or the pharmaceutically acceptable salt thereof, comprises at least one modification selected from the group consisting C-terminal amidation, N-terminal acylation, N-terminal acetylation, addition of an N- and/or a C-terminal cysteine, pegylation, and combinations thereof.

5. The method of claim 4, where the pegylation comprises addition of a PEG group to an N-terminal cysteine, a C-terminal cysteine, or both.

6. The method of claim 4, wherein the C-terminal amidation comprises a substituted amide, and/or wherein the N-terminal acylation comprises a substituted acyl group.

7. The method of claim 2, wherein the composition further comprises a pharmaceutically acceptable carrier, excipient, diluent, tonicity agent, viscosity building agent, and/or encapsulation.

8. The method of claim 2, wherein the peptide, or the pharmaceutically acceptable salt thereof, is present in a composition at a concentration of 1.0 nM to 100 µM.

9. The method of claim 2, wherein the composition further comprises tyloxapol.

10. The method of claim 2, wherein the subject has type 1 or type 2 diabetes.

11. The method of claim 10, further comprising administering to the subject one or more additional anti-diabetes therapies.

12. The method of claim 11, wherein the one or more additional anti-diabetes therapies are selected from the group consisting of an immune therapy; administration of a calcineurin inhibitor; administration of a glucagon-like peptide-1 (GLP-1) analog; and any combination thereof.

13. The method of claim 2, wherein the pancreatic islet cell is present within the subject, and the subject is a human.

14. The method of claim 1, wherein the peptide, or the pharmaceutically acceptable salt thereof, consists of the amino acid sequence of SEQ ID NO: 21, 22, 23, 24, 33, 34, 35, 36, 37, 38, 39, 40, 41, 42, 43, or 44.

15. The method of claim 2, wherein the peptide, or the pharmaceutically acceptable salt thereof, consists of the amino acid sequence of SEQ ID NO: 21, 22, 23, 24, 33, 34, 35, 36, 37, 38, 39, 40, 41, 42, 43, or 44.

16. The method of claim 10, wherein the peptide, or the pharmaceutically acceptable salt thereof, consists of the amino acid sequence of SEQ ID NO: 21, 22, 23, 24, 33, 34, 35, 36, 37, 38, 39, 40, 41, 42, 43, or 44.

17. The method of claim 1, wherein the peptide, or the pharmaceutically acceptable salt thereof, consists of the amino acid sequence of SEQ ID NO: 21.

18. The method of claim 1, wherein the peptide, or the pharmaceutically acceptable salt thereof, consists of the amino acid sequence of SEQ ID NO: 33.

19. The method of claim 1, wherein the peptide, or the pharmaceutically acceptable salt thereof, consists of the amino acid sequence of SEQ ID NO: 37.

20. The method of claim 1, wherein the peptide, or the pharmaceutically acceptable salt thereof, consists of the amino acid sequence of SEQ ID NO: 41.

21. The method of claim 2, wherein the peptide, or the pharmaceutically acceptable salt thereof, consists of the amino acid sequence of SEQ ID NO: 21.

22. The method of claim 2, wherein the peptide, or the pharmaceutically acceptable salt thereof, consists of the amino acid sequence of SEQ ID NO: 33.

23. The method of claim 2, wherein the peptide, or the pharmaceutically acceptable salt thereof, consists of the amino acid sequence of SEQ ID NO: 37.

24. The method of claim 2, wherein the peptide, or the pharmaceutically acceptable salt thereof, consists of the amino acid sequence of SEQ ID NO: 41.

25. The method of claim 10, wherein the peptide, or the pharmaceutically acceptable salt thereof, consists of the amino acid sequence of SEQ ID NO: 21.

26. The method of claim 10, wherein the peptide, or the pharmaceutically acceptable salt thereof, consists of the amino acid sequence of SEQ ID NO: 33.

27. The method of claim 10, wherein the peptide, or the pharmaceutically acceptable salt thereof, consists of the amino acid sequence of SEQ ID NO: 37.

28. The method of claim 10, wherein the peptide, or the pharmaceutically acceptable salt thereof, consists of the amino acid sequence of SEQ ID NO: 41.

* * * * *